US012742009B2

(12) United States Patent
Hu et al.

(10) Patent No.: US 12,742,009 B2
(45) Date of Patent: Sep. 22, 2026

(54) ANTIBODY, ANTIBODY-DRUG CONJUGATE THEREOF AND USE THEREOF

(71) Applicant: EVOPOINT BIOSCIENCES CO., LTD., Jiangsu (CN)

(72) Inventors: Yonghan Hu, Jiangsu (CN); Linfeng Xu, Jiangsu (CN); Zhenwei Wu, Jiangsu (CN); Ka Ruan, Jiangsu (CN); Wengui Wang, Jiangsu (CN)

(73) Assignee: EVOPOINT BIOSCIENCES CO., LTD. (CN)

(*) Notice: Subject to any disclaimer, the term of this patent is extended or adjusted under 35 U.S.C. 154(b) by 0 days.

(21) Appl. No.: 18/695,296

(22) PCT Filed: Sep. 27, 2022

(86) PCT No.: PCT/CN2022/121776

§ 371 (c)(1),
(2) Date: Mar. 25, 2024

(87) PCT Pub. No.: WO2023/046202

PCT Pub. Date: Mar. 30, 2023

(65) Prior Publication Data

US 2024/0409628 A1 Dec. 12, 2024

(30) Foreign Application Priority Data

Sep. 27, 2021 (CN) .......................... 202111139621.4
Aug. 1, 2022 (CN) .......................... 202210915323.8

(51) Int. Cl.

| | |
|---|---|
| ***C07K 16/00*** | (2006.01) |
| ***A61K 39/395*** | (2006.01) |
| ***A61K 47/68*** | (2017.01) |
| ***A61P 35/00*** | (2006.01) |
| ***C07K 16/28*** | (2006.01) |

(52) U.S. Cl.

CPC ........ *C07K 16/28* (2013.01); *A61K 47/68037* (2023.08); *A61K 47/6851* (2017.08); *A61P 35/00* (2018.01); *C07K 2317/24* (2013.01); *C07K 2317/33* (2013.01); *C07K 2317/732* (2013.01); *C07K 2317/92* (2013.01)

(58) Field of Classification Search

None

See application file for complete search history.

(56) References Cited

U.S. PATENT DOCUMENTS

| | | | | |
|---|---|---|---|---|
| 12,194,321 | B2 | 1/2025 | Jeffrey et al. | |
| 12,415,853 | B2 * | 9/2025 | Yang ...................... | C07K 16/28 |
| 2022/0233708 | A1 | 7/2022 | Bao et al. | |

FOREIGN PATENT DOCUMENTS

| | | | |
|---|---|---|---|
| CN | 111110862 | A | 5/2020 |
| CN | 111433188 | A | 7/2020 |
| CN | 111867630 | A | 10/2020 |
| CN | 111867639 | A | 10/2020 |
| CN | 112237634 | A | 1/2021 |
| EP | 3808376 | A1 | 4/2021 |
| WO | 2019195665 | A1 | 10/2019 |
| WO | 2020147321 | A1 | 7/2020 |
| WO | 2020228806 | A1 | 11/2020 |
| WO | 2022170971 | A1 | 8/2022 |

OTHER PUBLICATIONS

Vidarsson, Gestur et al., IgG subclasses and allotypes: from structure to effector functions, Oct. 20, 2014, doi: 10.3389/fimmu.2014.00520.
Kostova, Vesela et al., The Chemistry Behind ADCs , Pharmaceuticals 2021, 14, 442. https://doi.org/10.3390/ph14050442.
Ling, Xiang et al., A Novel Small Molecule FL118 That Selectively Inhibits Survivin, Mcl-1, XIAP and cIAP2 in a p53-Independent Manner, Shows Superior Antitumor Activity, PLoS ONE 7(9): e45571. doi:10.1371/journal.pone.0045571 (2012).
Noura Khaiwa et al., Camptothecin's journey from discovery to WHO Essential Medicine: Fifty years of promise, European Journal of Medicinal Chemistry 223 (2021) 113639.
Extended European Search Report for application No. 22872245.0, mailed Jul. 14, 2026.

* cited by examiner

*Primary Examiner* — Meera Natarajan
(74) *Attorney, Agent, or Firm* — Fox Rothschild LLP

(57) ABSTRACT

An antibody and an antibody-drug conjugate, which relate to an antibody and an antibody-drug conjugate (ADC) targeting Claudin 18.2 (CLDN18.2), as well as compositions containing the antibody and ADC molecules, and a therapeutic application thereof.

33 Claims, 13 Drawing Sheets

Specification includes a Sequence Listing.

| | HillSlope | EC50 |
|---|---|---|
| 25C7A5-HZ1 | 1.204 | 9.608 |
| 25C7A5-HZ1-B82 | 1.012 | 9.107 |
| 25C7A5-HZ2 | 0.9072 | 13.31 |
| 25C7A5-HZ2-B82 | 0.9894 | 8.257 |

| | 25C7A5-hz1 | 25C7A5-hz1-B81 | IMAB362 |
|---|---|---|---|
| HillSlope | 0.6313 | 0.6471 | 0.6696 |
| EC50 | 63.22 | 42.23 | 5978 |

| | 25C7A5-HZ1-B82 | 25C7A5-HZ2-B82 |
|---|---|---|
| EC50 | 41.26 | 35.53 |

| | IgG1-B81 | 25C7A5-hz1-B81 |
|---|---|---|
| HillSlope | -1.933 | -1.560 |
| EC50 | 27438 | 48.08 |

ADC candidate killing HEK293T-claudin18.1 cells

| | IgG1-B81 | 25C7A5-HZ1-B81 | 25C7A5-HZ1 |
|---|---|---|---|
| HillSlope | -5.407 | -1.283 | 0.2402 |
| EC50 | 37562 | 143.4 | 490530 |

ANTIBODY, ANTIBODY-DRUG CONJUGATE THEREOF AND USE THEREOF

CROSS-REFERENCE TO RELATED APPLICATIONS

The present application is a U.S. National Stage Application under 35 U.S.C. § 371 of International Application No. PCT/CN2022/121776 filed Sep. 27, 2022, which claims the benefit of priority to Chinese Patent Application No. 202111139621.4 filed Sep. 27, 2021, and Chinese Patent Application No. 202210915323.8 filed Aug. 1, 2022, the disclosures of all of which are hereby incorporated by reference in their entireties.

SEQUENCE LISTING

The sequence listing of the present application is submitted electronically as a computer readable sequence listing in XML format with a file name of "SeqList3-364131-00401.xml," a creation date of Oct. 17, 2025, and a size of 63,609 bytes. This sequence listing submitted is part of the specification and is hereby incorporated by reference in its entirety.

TECHNICAL FIELD

The present invention relates to an antibody and an antibody-drug conjugate, and particularly relates to an antibody and an antibody-drug conjugate (ADC) targeting Claudin18.2 (CLDN18.2), a composition comprising the antibody or ADC molecule, and a therapeutic application thereof.

BACKGROUND

Gastric cancer is the third leading cause of cancer death around the world, and the overall 5-year survival rate of patients with metastatic gastric cancer and esophagogastric junction adenocarcinoma (EGJA) is less than 20%. Despite numerous related studies, there is still an unmet need for gastric cancer treatment due to the large patient population. Especially among HER2-negative patients who lack an effective targeted therapeutic regimen, therapeutic options are relatively scarce, and patient survival is not optimistic.

Claudin18.2 is a member of the Claudin family of tight junction proteins, and mediates cell-to-cell tight junctions. Claudin18.2 is highly expressed in gastric cancer and pancreatic cancer, with limited expression only in gastric mucosal cells in normal tissues and no expression in other normal tissues, making it an ideal target for the development of ADC (antibody-drug conjugate) drugs.

Claudin18.2 belongs to the tetraspanins, comprising 2 extracellular loops and 1 intracellular loop, and the sequence thereof is very similar to that of its family member Claudin18.1, with a difference of 8 amino acids only in the first extracellular loop. Claudin18.1 is specifically expressed in the lungs, and therefore the development of an ADC drug that recognizes only Claudin18.2 but not Claudin18.1 is highly difficult and challenging.

In data made public at the 2016 ASCO meeting, Astellas' human-mouse chimeric antibody IMAB362 targeting Claudin18.2 plus chemotherapy regimen for the treatment of patients with locally advanced or metastatic gastric cancer achieved impressive results, extending the patients' progression-free survival and overall survival by nearly half. However, currently, there are still no monoclonal antibodies or ADC drugs targeting Claudin18.2 that have been approved for marketing. Thus, the development of an anti-Claudin18.2 antibody and ADC drug with differentiated and superior targeting properties and excellent in-vivo tumor-killing effects can provide a wider and better medication option for patients with gastric cancer.

SUMMARY

In a first aspect, the present invention provides an antibody-drug conjugate (ADC) having the following formula (I), or a pharmaceutically acceptable salt or solvate thereof:

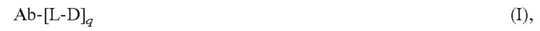

$$Ab\text{-}[L\text{-}D]_q \quad (I),$$

wherein

Ab represents an anti-Claudin18.2 antibody,

L represents a linker,

D represents a cytotoxic or cytostatic drug, e.g., a topoisomerase I inhibitor, and q=1-20, e.g., q=1-8, 2-8, 4-8, or 6-8, wherein Ab comprises three CDRs of a heavy chain variable region (VH) sequence of SEQ ID NO: 1 or 3 and three CDRs of a light chain variable region (VL) sequence of SEQ ID NO: 2, wherein preferably, the CDRs are defined according to Kabat or IMGT, or a combination thereof.

In a second aspect, the present invention provides a composition comprising the ADC or the pharmaceutically acceptable salt or solvate thereof of the present invention.

In a third aspect, the present invention provides use of the ADC or the pharmaceutically acceptable salt or solvate thereof and the composition thereof of the present invention in the treatment of a Claudin18.2-positive tumor.

In a fourth aspect, the present invention provides an anti-Claudin18.2 antibody, and a pharmaceutical composition thereof and use thereof.

BRIEF DESCRIPTION OF THE DRAWINGS

FIG. 1A shows the detection of an HEK293T-Claudin18.2 (human) stable cell line using a PE fluorescently labeled anti-human Claudin18.2 antibody; FIG. 1B shows the detection of an HEK293T-Claudin18.1 (human) stable cell line using an APC fluorescently labeled anti-human Claudin18.1 antibody. FIG. 1C shows the detection of an L929-Claudin18.2 (human) stable cell line using an APC fluorescently labeled anti-human Claudin18.2 antibody. FIG. 1D shows the detection of a CHO-Claudin18.2 (human) stable cell line using an APC fluorescently labeled anti-human Claudin18.2 antibody. FIG. 1E shows the detection of an HEK293T-Claudin18.2 (cynomolgus monkey) stable cell line using a PE fluorescently labeled anti-monkey Claudin18.2 antibody. FIG. 1F shows the detection of an HEK293T-Claudin18.2 (rat) stable cell line using an APC fluorescently labeled anti-rat Claudin18.2 antibody. FIG. 1G shows the detection of an HEK293T-Claudin18.2 (mouse) stable cell line using an APC fluorescently labeled anti-mouse Claudin18.2 antibody. FIG. 1H shows the detection of an NUGC4-Claudin18.2 (human) stable cell line using an APC fluorescently labeled anti-human Claudin18.2 antibody. FIG. 1I shows the detection of an NUGC4 tumor cell line using an APC fluorescently labeled anti-human Claudin18.2 antibody.

DETAILED DESCRIPTION

Definitions

Figure 1A:
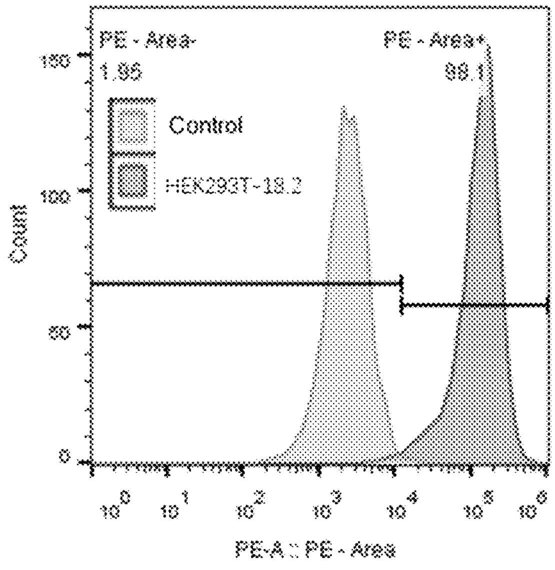
FIGS. 1A-1I show the detection of the positive rates of Claudin18.2 or Claudin18.1 expression in different cell lines of Example I-1 by FACS technique using fluorescently labeled antibodies. An isotype control antibody is used as a control.
Figure 1B:
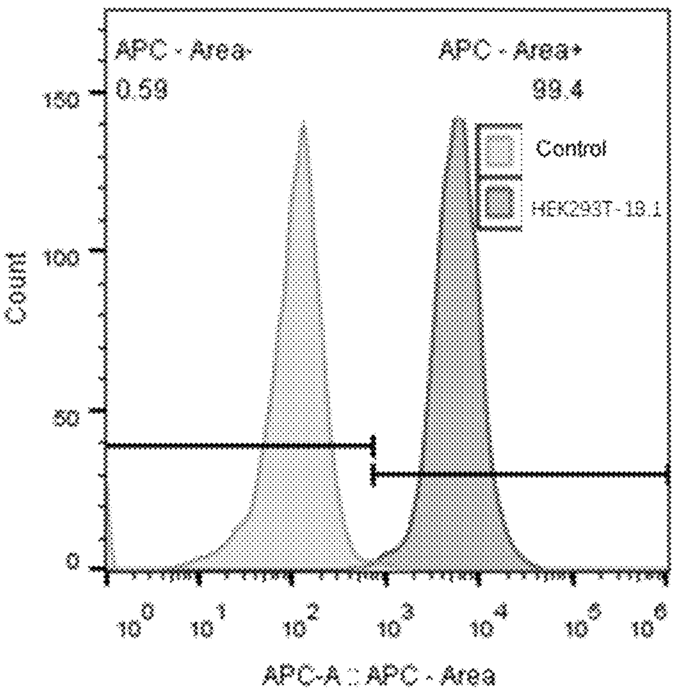
Figure 1C:
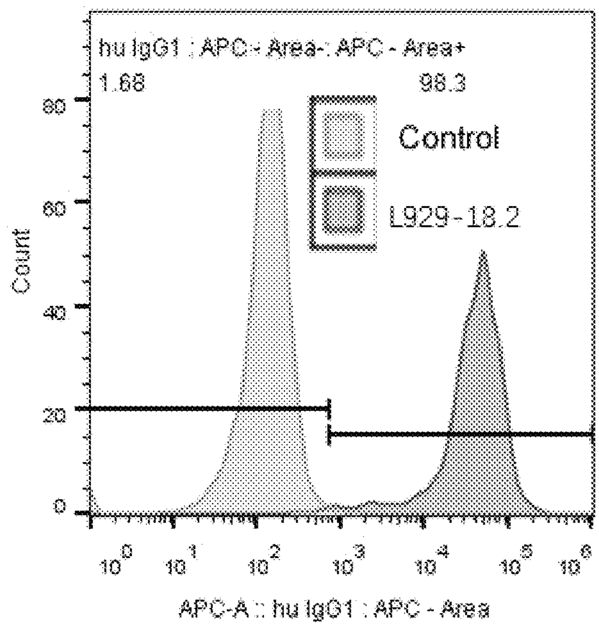
Figure 1D:
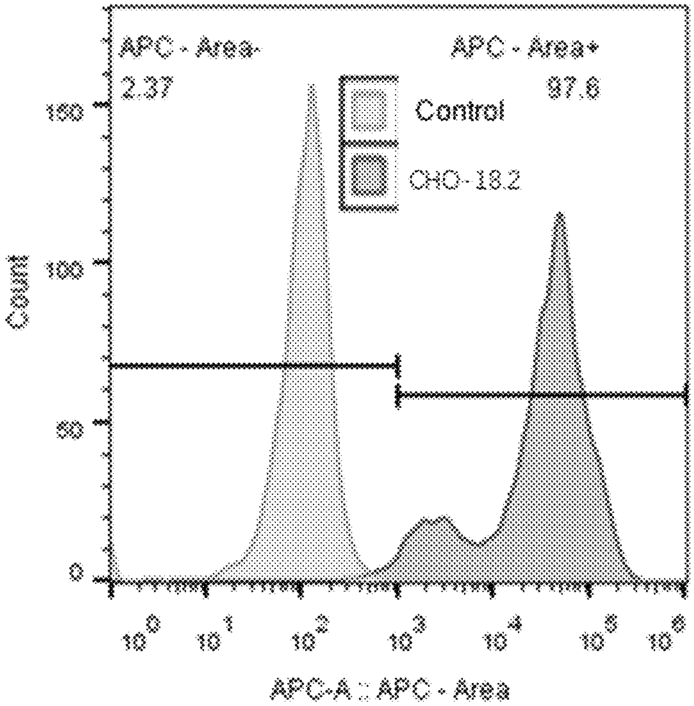
Figure 1E:
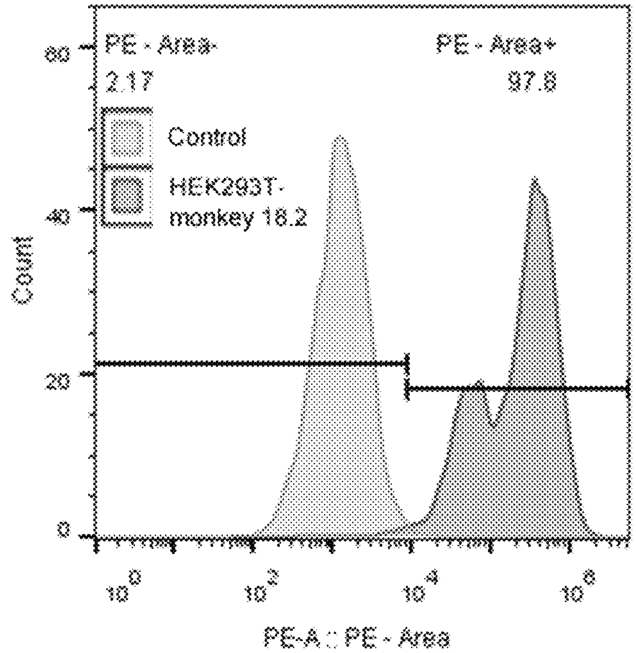
Figure 1F:
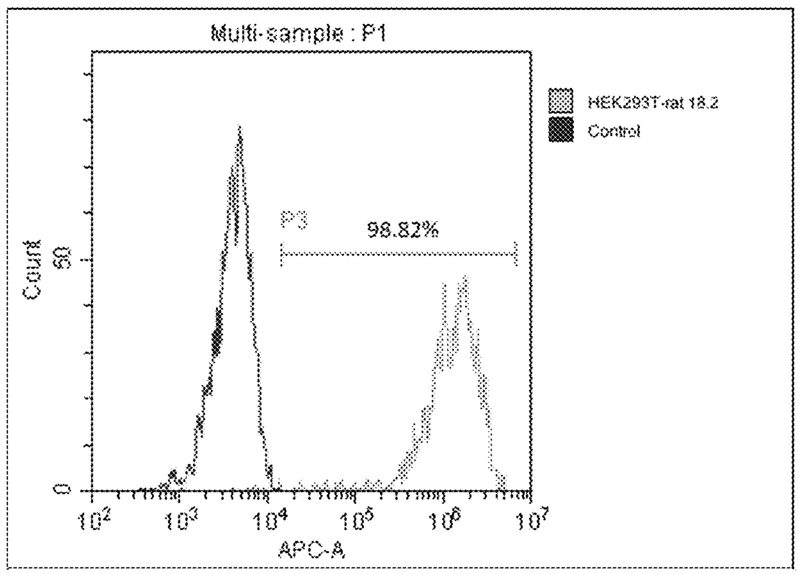
Figure 1G:
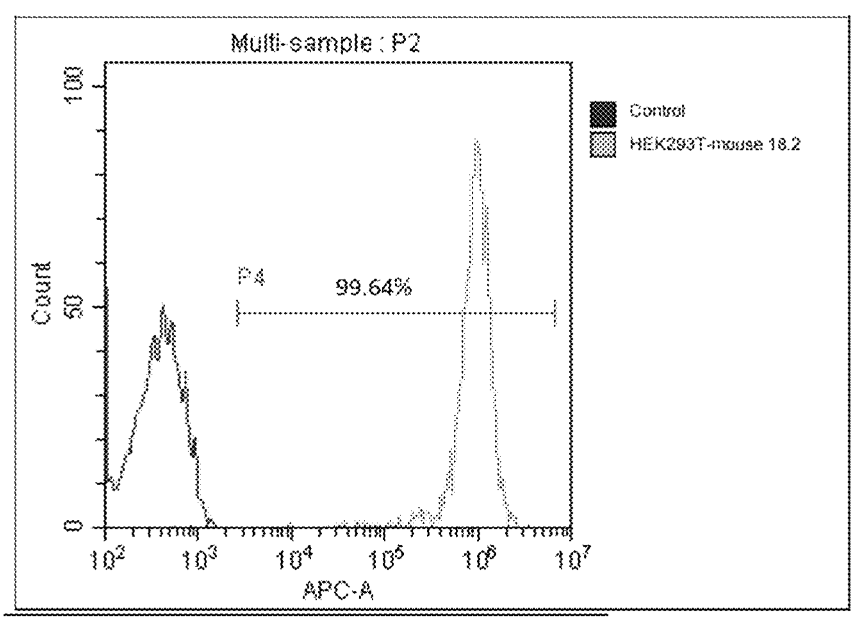
Figure 1H:
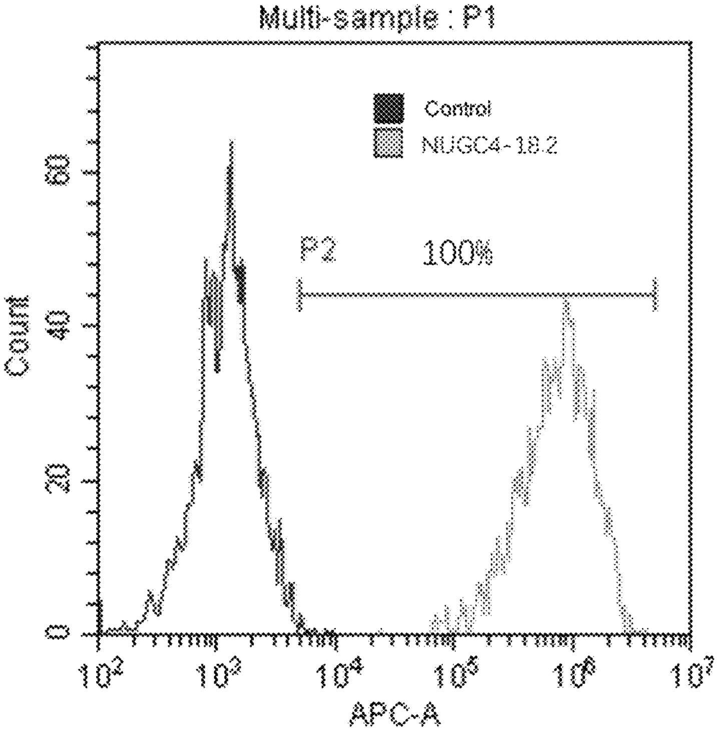
Figure 1I:
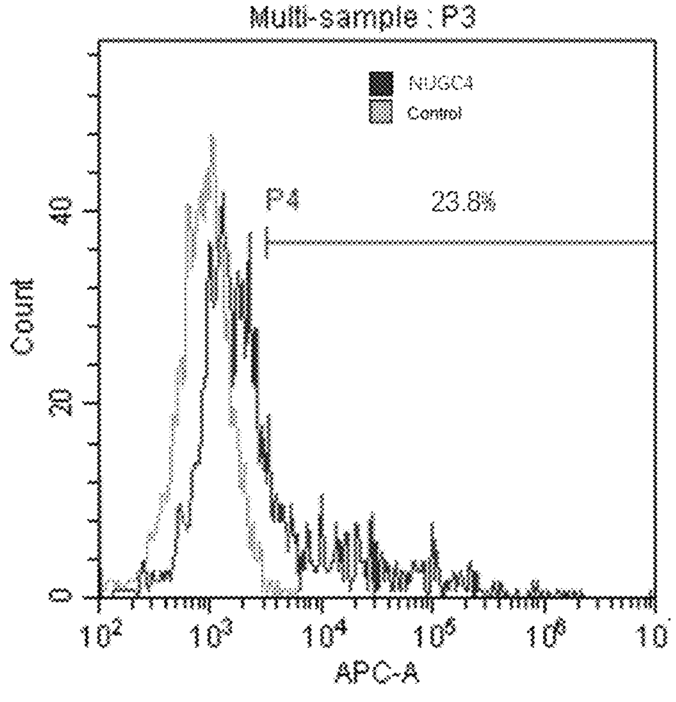

Unless otherwise defined, all technical and scientific terms used herein have the same meaning as those commonly understood by those of ordinary skill in the art. For the purposes of the present invention, the following terms are defined below.

When a tradename is used herein, the tradename includes the product formula, generic drug, and active pharmaceutical ingredient of the product with the tradename, unless otherwise clearly defined in the context.

The term "about" used in combination with a numerical value is intended to encompass the numerical values in a range from a lower limit less than the specified numerical value by 5% to an upper limit greater than the specified numerical value by 5%.

The term "and/or" should be understood to mean any one of the options or a combination of any two or more of the options.

As used herein, the term "comprise" or "include" is intended to mean that the elements, integers or steps are included, but not to the exclusion of any other elements, integers or steps. The term "comprise" or "include" used herein, unless indicated otherwise, also encompasses the situation where the entirety consists of the described elements, integers or steps. For example, when referring to an antibody variable region "comprising" a specific sequence, it is also intended to encompass an antibody variable region consisting of the specific sequence.

The terms "Claudin18" and "CLDN18" are used interchangeably herein to refer to the CLDN18 member of the Claudin family of tight junction proteins. CLDN18 is a transmembrane protein that spans the membrane four times, with both the N-terminus and C-terminus being located in the cytoplasm, and has extracellular loop 1 and extracellular loop 2, wherein the first extracellular loop near the N-terminus (i.e., extracellular loop 1) consists of an average of about 53 amino acids, and the second extracellular loop (i.e., extracellular loop 2) consists of about 30 amino acids. CLDN18 includes two splice variants, CLDN18.1 and CLDN18.2, which differ by 8 amino acids in extracellular loop 1. In normal tissues, the expression of CLDN1 is limited to the lungs, and the expression of CLDN2 is limited to the gastric mucosa.

Herein, the term "CLDN18.1" preferably relates to human CLDN18.1, e.g., human CLDN18.1 having the amino acid sequence of NCBI_057453.1. The term also encompasses Claudin18.1 from other species such as cynomolgus monkeys, mice, and rats, but unless otherwise specified, the term used herein refers to human CLDN18.1.

Herein, the term "CLDN18.2" preferably relates to human CLDN18.2, e.g., human CLDN18.2 having an amino acid sequence of NCBI_001002026.1. The term also encompasses Claudin18.2 from other species, e.g., cynomolgus monkey Claudin18.2 (e.g., the amino acid sequence of XP_015300615.1), mouse Claudin18.2 (e.g., the amino acid sequence of NP_001181850.1), and rat Claudin18.2 (e.g., the amino acid sequence of NP_001014118.1). Herein, unless otherwise specified, the term refers to human CLDN18.2.

Herein, the terms "CLDN18", "CLDN18.1", and "CLDN18.2" also encompass post-translationally modified variants and conformational variants, as well as mutants, in particular, naturally occurring variants, allelic variants, and species homologs.

Herein, the term "CLDN18.2-positive" cell refers to a cell that is positive for CLDN18.2 cell surface expression, such as a cancer cell, an engineered cancer cell, or an engineered non-tumor cell. The expression level of CLDN18.2 on the cell surface can be determined by any conventional method known in the art for determining the expression level of cell surface antigens, for example, an FACS detection method or an immunofluorescence staining method; and optionally, cells presenting positive for CLDN18.2 cell surface expression are identified by comparison with a predetermined reference value. Preferably, the measured value for the expression level of CLDN18.2 on positive cells is at least 2-fold higher than the predetermined reference value. The predetermined reference value may be determined by those skilled in the art in a conventional manner. In one embodiment, the predetermined reference value may be a value for the expression level of CLDN18.2 determined on normal cells other than gastric mucosa using the same detection method. In another embodiment, the predetermined reference value may be determined by comparing the intensity of fluorescent staining produced on cells by a specific CLDN18.2 antibody relative to an isotype control antibody using the FACS method as described in Example I-1 of the present application, for example, the predetermined reference value may be set to be at least 10-fold higher than the average fluorescence staining intensity of the isotype control antibody.

In some embodiments, preferably, CLDN18.2-positive cells express a sufficiently high level of CLDN18.2 on the cell surface, such that in a detection method such as immunofluorescence staining or FACS, they can be bound by a CLDN18.2-specific antibody and produce a detection signal that is higher than the predetermined reference value, and/or produce a signal that is significantly differentiated from that of non-cancerous normal cells other than gastric mucosa (e.g., at least 2-fold higher, or preferably at least 10-fold or 100-fold higher, or more).

Herein, the term "antibody" refers to a polypeptide comprising at least an immunoglobulin light chain variable region or heavy chain variable region that specifically recognizes and binds to an antigen. The term encompasses various antibody structures, including but not limited to, monoclonal antibodies, polyclonal antibodies, single-chain or multi-chain antibodies, monospecific or multispecific antibodies (e.g., bispecific antibodies), chimeric or humanized antibodies, full-length antibodies, and antibody fragments, as long as they exhibit the desired antigen-binding activity.

Herein, "whole antibody" (used interchangeably herein with "full-length antibody", "complete antibody", and "intact antibody") refers to an immunoglobulin molecule comprising at least two heavy (H) chains and two light (L) chains. Each heavy chain consists of a heavy chain variable region (abbreviated herein as VH) and heavy chain constant regions. Each light chain consists of a light chain variable region (abbreviated herein as VL) and a light chain constant region. The variable regions are domains in the heavy chains or light chains of antibodies that participate in binding of the antibodies to the antigens thereof. The constant regions are not directly involved in binding of the antibodies to the antigens, but exhibit a variety of effector functions. The light chains of antibodies can be categorized into one of two classes (known as kappa (κ) and lambda (λ)) based on the amino acid sequences of their constant regions. The heavy chains of antibodies can be divided into 5 major distinct classes based on the amino acid sequences of their constant regions: IgA, IgD, IgE, IgG, and IgM, and several of these classes can be further divided into subclasses, e.g., IgG1, IgG2, IgG3, IgG4, IgA1, and IgA2.

Herein, the terms "antibody fragment" and "antigen-binding fragment" of an antibody are used interchangeably to refer to a molecule that is not an intact antibody, which comprises the portion of the intact antibody for binding to the antigen to which the intact antibody binds. As understood by those skilled in the art, for antigen binding purposes, antibody fragments generally comprise amino acid residues from "complementarity determining regions" or "CDRs". Antibody fragments may be prepared by the recombinant DNA technology, or by enzymatic or chemical cleavage of intact antibodies. Examples of antibody fragments include, but are not limited to, Fab, scFab, disulfide-linked scFab, Fab', $F(ab')_2$, Fab'-SH, Fv, scFv, disulfide-linked scFv, diabody, triabody, tetrabody, and minibody. In some embodiments according to the present invention, the antibody fragment comprises a cysteine residue portion for forming an interchain disulfide bond between the light chain and the heavy chain, e.g., cysteine residues of the Fab region and/or the hinge region of the IgG1 antibody, to provide amino acid residue sites useful for sulfhydryl conjugation chemistry. In some other embodiments according to the present invention, the antibody fragment comprises cysteine residues introduced into the Fc region, to provide amino acid residue sites useful for sulfhydryl conjugation chemistry.

Herein, the term "immunoglobulin" refers to a protein having a structure of a naturally occurring antibody. For example, immunoglobulins of the IgG class are heterotetrameric proteins of about 150,000 daltons, consisting of two light chains and two heavy chains that are disulfide-bonded. From the N-terminus to the C-terminus, each immunoglobulin heavy chain has one heavy chain variable region (VH), also known as a heavy chain variable domain, followed by three heavy chain constant domains (CH1, CH2, and CH3). From the N-terminus to the C-terminus, each immunoglobulin light chain has one light chain variable region (VL), also known as a light chain variable domain, followed by one light chain constant domain (CL). Accordingly, reference herein to an antibody being an IgG antibody means that the antibody is a heterotetrameric protein with an IgG immunoglobulin structure. In an IgG antibody, the VH-CH1 of the heavy chain is generally paired with the VL-CL of the light chain to form a Fab fragment that specifically binds to an antigen. Thus, an IgG antibody essentially consists of two Fab molecules and two dimerized Fc regions connected by an immunoglobulin hinge region. IgG immunoglobulins can be divided into subclasses, e.g., γ1 (IgG1), γ2 (IgG2), $\gamma^3$ (IgG3), and γ4 (IgG4), based on the sequences of the heavy chain constant regions. The light chains of IgG immunoglobulins can also be divided into one of two classes, known as κ and λ, based on the amino acid sequences of their constant domains. In some embodiments, the antibody according to the present invention is an IgG antibody, e.g., an IgG1, IgG2, IgG3 or IgG4 antibody. In some other embodiments, the antibody according to the present invention is an IgGκ or IgGλ antibody, e.g., an IgG1κ or IgG1λ antibody.

Herein, the terms "complementarity determining region", "CDR" and "hypervariable region" are used interchangeably to refer to a region in an antibody variable domain which is highly variable in sequence, forms a structurally defined loop ("hypervariable loop") and/or contains antigen-contacting residues ("antigen-contacting sites"). The CDRs are primarily responsible for binding to antigenic epitopes. Herein, the CDRs of heavy and light chains of an antibody are numbered sequentially from the N-terminus, and are generally referred to as CDR1, CDR2, and CDR3. The CDRs located in the heavy chain variable domain of the antibody are referred to as HCDR1, HCDR2, and HCDR3, whereas the CDRs located in the light chain variable domain of the antibody are referred to as LCDR1, LCDR2, and LCDR3. In a given amino acid sequence of a light chain variable region or a heavy chain variable region, the CDR sequences may be determined using a variety of schemes well known in the art. For example, annotations of CDRs in a given light chain variable region or heavy chain variable region may be obtained at http://www.abysis.org/abysis/, including CDR sequences defined based on Kabat, AbM, Chothia, Contact, and IMGT. In addition, the CDRs may also be determined based on having the same Kabat numbering positions as the reference CDR sequences. Unless otherwise stated, residue positions of an antibody variable region (including heavy chain variable region residues and light chain variable region residues) are numbered according to the Kabat numbering system (Kabat et al., Sequences of Proteins of Immunological Interest, 5th Ed. Public Health Service, National Institutes of Health, Bethesda, Md. (1991)).

Herein, "variable region" or "variable domain" is a domain in the heavy chain or light chain of an antibody that participates in binding of the antibody to the antigen thereof. The heavy chain variable region (VH) and light chain variable region (VL) can be further subdivided into hypervariable regions (HVRs, also known as complementarity determining regions (CDRs)) with more conserved regions (i.e., framework regions (FRs)) inserted therebetween. Each VH or VL consists of three CDRs and four FRs, arranged from the N-terminus to the C-terminus in the following order: FR1, CDR1, FR2, CDR2, FR3, CDR3, FR4. In some aspects, one or more residues in one or both of the two variable regions (i.e., VH and/or VL) may be modified, for example, one or more CDRs and/or one or more framework regions are subjected to residue modifications, particularly conservative residue substitutions, to obtain antibody variants that still substantially retain at least one biological property (e.g., antigen-binding ability) of the antibody molecule prior to the modifications. In still other aspects, the variable regions of the antibody may be modified by CDR grafting. Since CDR sequences are responsible for most of the antibody-antigen interactions, recombinant antibody variants that simulate the properties of known antibodies can be constructed. In such antibody variants, CDR sequences from known antibodies are grafted onto the framework regions of different antibodies with different properties. Properties of the mutated and/or modified antibodies or ADCs comprising the same, such as target antigen-binding properties or other desired functional properties, such as the endocytosis, pharmacokinetics, and in vivo tumor-killing activity of the ADCs, can be assessed in in-vitro or in-vivo assays.

The term "chimeric antibody" refers to an antibody in which the variable region sequences are derived from one species and the constant region sequences are derived from another species, e.g., an antibody in which the variable region sequences are derived from a mouse antibody and the constant region sequences are derived from a human antibody.

Herein, the term "humanized antibody" refers to an antibody in which CDR sequences derived from another mammalian species, e.g., mouse germline, are grafted onto human framework sequences. Additional framework region modifications may be made within the human framework sequences and/or additional amino acid modifications may be made in the CDR sequences, e.g., to perform affinity maturation of the antibody. Herein, in some embodiments, the antibody of the present invention is a humanized antibody having framework region sequences "derived from" a specific human germline sequence. As used herein, "derived from" means that the amino acid sequence of the framework region of the antibody has at least 90%, more preferably at least 95%, even more preferably at least 96%, 97%, 98% or 99% identity to the amino acid sequence of the corresponding framework region encoded by the human germline immunoglobulin gene, and the antibody retains the antigen-binding activity, for example, it has equivalent (e.g., ±10%) CLDN18 binding affinity to 25C7A5-HZ1 or -HZ2, or to 2D3A11-HZ1 or -HZ2.

Herein, the term "isolated" antibody refers to an antibody that has been separated from a component of its natural environment. In some embodiments, the antibody is purified to a purity greater than 95% or 99%, which can be determined, for example, by electrophoresis (e.g., SDS-PAGE, isoelectric focusing (IEF), or capillary electrophoresis) or chromatography (e.g., ion exchange or reverse-phase HPLC).

The term "epitope" refers to the region of an antigen to which an antibody binds. An epitope can be formed from contiguous amino acids or from non-contiguous amino acids juxtaposed by tertiary folding of a protein. In the present invention, preferably, the antibody according to the present invention binds to a native epitope of human Claudin18.2, more preferably, to a native epitope of human Claudin18.2 expressed on the cell surface. Thus, in a preferred embodiment, the binding of the antibody of the present invention to a native epitope of human Claudin18.2 is detected by a cell-based assay.

Herein, the term "affinity" or "binding affinity" refers to the inherent binding affinity that reflects the interaction between members of a binding pair. The affinity can be measured by common methods known in the art. One specific method for measuring the affinity is the cell-based ELISA assay as described in the examples herein, and another specific method is the FACS assay as described in the examples herein. In one embodiment, in a cell-based assay, such as the one performed as described in Example I, an antibody is considered to have high affinity for Claudin18.2 if the antibody has a comparable (i.e., ±10%) or smaller EC50 value and/or a comparable (i.e., ±10%) or higher maximum binding signal value to the reference antibody IMAB362.

The term "specifically binds to" means that an antibody binds to a target antigen selectively or preferentially relative to a non-target antigen. Herein, in an antigen-binding assay, such as the FACS assay or cell-based ELISA as described in the examples, it is considered that an antibody "specifically binds to human Claudin18.2" if the antibody binds (particularly binds with high affinity) to human Claudin18.2 expressed on the cell surface, but does not bind or substantially does not bind to human Claudin18.1 expressed on the cell surface. The binding of the antibody to human Claudin18.2 or human Claudin18.1 expressed on the cell surface can be measured in a cell-based ELISA or FACS assay to determine the binding specificity of the antibody to Claudin18.2.

Herein, in a cell-based assay, when an antibody has no significant affinity for human Claudin18.1 and does not significantly bind to human Claudin18.1, in particular does not produce a detectable signal that is significantly different from the background, such characterization of the antibody is referred to as not binding or substantially not binding to human Claudin18.1 (herein, this is also referred to as having "no non-specific binding" to human Claudin18.1). Preferably, in the present invention, the non-specific binding of the antibody according to the present invention to Claudin18.1-expressing cells is determined by an FACS assay using a recombinant cell line with a Claudin18.1 expression positive rate of greater than 95% or greater than 98% (such as a recombinant HEK293T stable cell line), for example, as described in Example I. Depending on the particular assay chosen, those skilled in the art can select appropriate negative and/or positive controls. For example, an isotype control can be used to eliminate background staining due to non-specific binding of the antibody to the cells.

However, as understood by those skilled in the art, an antibody that specifically binds to human Claudin18.2 and has no non-specific binding to human Claudin18.1 can have cross-reactivity with Claudin18.2 proteins from other species. Herein, the term "cross-reactivity" refers to the ability of an antibody to bind to Claudin18.2 from different species. For example, in some embodiments, the antibody according to the present invention specific for human Claudin18.2 may also bind to Claudin18.2 from other species (e.g., cynomolgus monkey, mouse and/or rat Claudin18.2). Methods for determining cross-reactivity include the methods described in the examples and standard assays known in the art, e.g., flow cytometry or the cell-based ELISA technique. Species cross-reactivity of antibodies is advantageous in some cases. For example, when a target antibody has species cross-reactivity with preclinical laboratory animals, e.g., mice, rats, or primates, it will facilitate preclinical safety and efficacy evaluations of the target antibody and ADCs thereof prior to therapeutic or diagnostic use in humans.

Herein, the term "isotype" refers to the class of antibodies determined according to the heavy chain constant regions of the antibodies. For example, the antibodies according to the present invention may be IgA (e.g., IgA1 or IgA2), IgG1, IgG2 (e.g., IgG2a or IgG2b), IgG3, IgG4, IgE, IgM, and IgD antibodies, and have heavy chain constant regions of the immunoglobulin class. For example, the antibodies of the present invention may also be IgG1 antibodies having constant regions of human IgG1. Furthermore, the present invention contemplates not only antibodies having native sequence constant regions, but also antibodies comprising variant sequence constant regions.

The term "Fc region" is used herein to define the C-terminal region of an immunoglobulin heavy chain that comprises at least a part of the constant regions. The "Fc region" includes native sequence Fc regions and variant Fc regions.

Herein, the term "native sequence Fc region" encompasses naturally occurring Fc region sequences of various immunoglobulins, such as Fc region sequences of various Ig subclasses and allotypes thereof (Gestur Vidarsson et al., IgG subclasses and allotypes: from structure to effector functions, 20 Oct. 2014, doi: 10.3389/fimmu.2014.00520). In some embodiments, the heavy chain Fc region of human IgG has an amino acid sequence extending from Cys226 or from Pro230 to the carboxyl terminus of the heavy chain. However, the C-terminal lysine (Lys447) of the Fc region may or may not be present. In still other embodiments, the heavy chain Fc region of human IgG carries a hinge sequence or a part of the hinge sequence of a native immunoglobulin at the N-terminus, e.g., according to EU numbering, the sequence from E216 to T225 or the sequence from D221 to T225.

Herein, the term "variant sequence Fc region" refers to an Fc region polypeptide comprising modifications relative to the native sequence Fc region polypeptide. The modifications may be the additions, deletions or substitutions of amino acid residues. The substitutions may include substitutions of naturally occurring amino acids and non-naturally occurring amino acids. The purpose of the modifications may be to alter the binding of the Fc region to its receptor and the resulting effector functions.

Herein, the term "effector function" refers to biological activities attributed to an immunoglobulin Fc region that vary with immunoglobulin isotype. Examples of immunoglobulin effector functions include: C1q binding and complement-dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake in antigen-presenting cells, down regulation of cell surface receptors (such as B-cell receptors), and B-cell activation. Depending on the intended use of the antibody molecule, the effector functions of the target antibody may be altered relative to an antibody molecule having a wild-type Fc region, such as by reducing or eliminating ADCC activity or CDC activity.

Herein, the term "ADCC" refers to antibody-dependent cell-mediated cytotoxicity. ADCC is mediated in humans primarily by natural killer cells (NK cells). In ADCC, an antibody binds to an antigen displayed on the surface of a target cell, and FcγRIIIA on the surface of NK cells recognizes the Fc region of the antibody, so that the NK cells are activated to release perforin and granzyme, resulting in lysis and apoptosis of the target cell. ADCC activity of an antibody can be evaluated, for example, using the fluorescein reporter system described in Example I. In some cases, when the ADCC effector activity of an antibody is not desired, the ADCC activity of the antibody can be removed by modifying the Fc region of the antibody.

Herein, the term "CDC" refers to complement-dependent cytotoxicity. In CDC, the Fc region of an antibody binds to the complement molecule C1q to form a membrane attack complex, resulting in clearance of the target cell. IgM is the most potent isotype for complement activation. Both IgG1 and IgG3 are also very effective in directing CDC through the classical complement activation pathway. CDC activity of an antibody can be detected, for example, using the guinea pig serum killing experiment described in Example I. In some cases, when the CDC effector activity of an antibody is not desired, the CDC activity of the antibody can be removed by modifying the Fc region of the antibody.

Herein, the term "receptor-mediated endocytosis" refers to the process whereby a ligand/receptor complex is internalized and delivered into the cytosol or transferred to a suitable intracellular compartment, triggered by binding of the ligand to the corresponding receptor on the cell surface. The receptor-mediated endocytic activity of an antibody can be characterized by measuring the endocytosis rate, for example, by the method described in Example I. As shown in the examples, the antibody of the present invention can induce Claudin18.2 receptor-mediated endocytosis after binding to Claudin18.2 expressed on the cell surface, and the antibody of the present invention with such endocytosis property, after being conjugated with a drug (e.g., a small molecule toxic drug molecule) to form an ADC, can be effectively used as a means for delivering the anti-tumor drug into cancer cells.

Herein, "sequence identity" refers to the degree to which sequences are identical on a nucleotide-by-nucleotide or amino acid-by-amino acid basis over a comparison window. The "percent sequence identity" can be calculated by the following steps: comparing two optimally aligned sequences over a comparison window; determining the number of positions in which nucleic acid bases (e.g., A, T, C, G, and I) or amino acid residues (e.g., Ala, Pro, Ser, Thr, Gly, Val, Leu, Ile, Phe, Tyr, Trp, Lys, Arg, His, Asp, Glu, Asn, Gln, Cys, and Met) are the same in the two sequences to obtain the number of matched positions; dividing the number of matched positions by the total number of positions over the comparison window (i.e., the window size); and multiplying the result by 100 to obtain a percent sequence identity. Optimal alignment for determining the percent sequence identity may be achieved in a variety of ways known in the art, for example, using publicly available computer software such as BLAST, BLAST-2, ALIGN, or Megalign (DNASTAR) software. Those skilled in the art can determine suitable parameters for alignment of the sequences, including any algorithm necessary to yield optimal alignment within a full-length sequence range or target sequence region being compared.

Herein, with respect to antibody sequences, the percent amino acid sequence identity is determined by performing an optimal alignment of candidate antibody sequences with a given antibody sequence, and in a preferred embodiment, the optimal alignment is performed according to the Kabat numbering scheme. Herein, without specifying the comparison window (i.e., the target antibody region to be compared), it will be suitable for alignment over the full length of the given antibody sequence. In some embodiments, with respect to antibodies, the sequence identity may be achieved throughout the heavy chain variable region and/or the light chain variable region, or the percent sequence identity may be limited to the framework regions only, while the sequences of corresponding CDRs remain 100% identical.

Herein, the "reference antibody IMAB362" refers to an anti-Claudin18.2 antibody constructed using the amino acid sequences of the heavy and light chain variable regions from the 175D10 monoclonal antibody disclosed in patent CN 101312989 B. In the context of reference to comparison with a reference antibody IMAB362, the reference antibody IMAB362 will have the same antibody structure as the antibody to be compared in parts other than the variable regions, e.g., the same heavy and light chain constant region sequences when both have heavy and light chain constant region structures.

In the present application, the term "halogen" generally refers to fluorine, chlorine, bromine, or iodine, and it may be, for example, fluorine or chlorine.

The term "alkyl" as used herein refers to a linear or branched saturated hydrocarbyl group consisting of carbon atoms and hydrogen atoms. Specifically, the alkyl group has 1-10 carbon atoms, e.g., 1-8, 1-6, 1-5, 1-4, 1-3, or 1-2 carbon atoms. For example, as used herein, the term "$C_1$-$C_6$ alkyl" refers to a linear or branched saturated hydrocarbyl group having 1-6 carbon atoms, examples of which include, e.g., methyl, ethyl, propyl (including n-propyl and isopropyl), butyl (including n-butyl, isobutyl, sec-butyl, or tert-butyl), pentyl (including n-pentyl, isopentyl, and neopentyl), hexyl (including n-hexyl, 2-methylpentyl, 3-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, and 2-ethylbutyl), and the like.

The term "alkenyl" as used herein refers to a linear or branched unsaturated hydrocarbyl group consisting of carbon atoms and hydrogen atoms with at least one double bond. Specifically, the alkenyl group has 2-8, e.g., 2-6, 2-5, 2-4, or 2-3 carbon atoms. For example, as used herein, the term "$C_2$-$C_6$ alkenyl" refers to a linear or branched alkenyl group having 2-6 carbon atoms, e.g., vinyl, propenyl, allyl, 1-butenyl, 2-butenyl, 1,3-butadienyl, 1-pentenyl, 2-pentenyl, 3-pentenyl, 1,3-pentadienyl, 1,4-pentadienyl, 1-hexenyl, 2-hexenyl, 3-hexenyl, 1,4-hexadienyl, and the like.

The term "alkynyl" as used herein refers to a linear or branched unsaturated hydrocarbyl group consisting of carbon atoms and hydrogen atoms with at least one triple bond. Specifically, the alkynyl group has 2-8, e.g., 2-6, 2-5, 2-4, or 2-3 carbon atoms. For example, as used herein, the term "$C_2$-$C_6$ alkynyl" refers to a linear or branched alkynyl group having 2-6 carbon atoms, e.g., ethynyl, propynyl, propargyl, 1-butynyl, 2-butynyl, 1-pentynyl, 2-pentynyl, 3-pentynyl, 4-methyl-1-pentynyl, 1-hexynyl, 2-hexynyl, 3-hexynyl, 5-methyl-2-hexynyl, and the like.

The term "alkylene" as used herein refers to a divalent group derived from a linear or branched saturated alkane by the removal of two hydrogen atoms from the same carbon atom or two different carbon atoms. Specifically, the alkylene group has 1-10 carbon atoms, e.g., 1-6, 1-5, 1-4, 1-3, or 1-2 carbon atoms. For example, as used herein, the term "$C_1$-$C_6$ alkylene" refers to a linear or branched alkylene group having 1-6 carbon atoms, including but not limited to, methylene, ethylene, propylene, butylene, and the like.

The term "alkenylene" as used herein refers to a divalent group derived from a linear or branched unsaturated olefin comprising at least one double bond by the removal of two hydrogen atoms from the same carbon atom or two different carbon atoms. Specifically, the alkenylene group has 2-8, e.g., 2-6, 2-5, 2-4, or 2-3 carbon atoms. For example, as used herein, the term "$C_2$-$C_6$ alkenylene" refers to a linear or branched alkenylene group having 2-6 carbon atoms, e.g., ethenylene, propenylene, allylene, butenylene, pentenylene, and hexenylene.

The term "alkynylene" as used herein refers to a divalent group derived from a linear or branched unsaturated alkyne comprising at least one triple bond by removal of two hydrogen atoms from the same carbon atom or two different carbon atoms. Specifically, the alkynylene group has 2-8, e.g., 2-6, 2-5, 2-4, or 2-3 carbon atoms. For example, as used herein, the term "$C_2$-$C_6$ alkynylene" refers to a linear or branched alkynylene group having 2-6 carbon atoms, e.g., ethynylene, propynylene, propargylene, butynylene, pentynylene, and hexynylene.

The term "cycloalkyl" as used herein refers to a monocyclic, fused polycyclic, bridged polycyclic, or spirocyclic non-aromatic monovalent hydrocarbon ring structure having a specified number of ring atoms, which may be saturated or unsaturated, e.g., comprises 1 or more double bonds. The cycloalkyl group may comprise 3 or more, e.g., 3-18, 3-10, or 3-8 carbon atoms in the ring, and may be, e.g., $C_{3-10}$ cycloalkyl, $C_{3-8}$ cycloalkyl, $C_{3-6}$ cycloalkyl, or $C_{5-6}$ cycloalkyl. Examples of the cycloalkyl group include, but are not limited to, cyclopropyl, cyclobutyl, cyclopentyl, cyclohexyl, cycloheptyl, and the like.

The term "heterocycle" or "heterocyclyl" as used herein refers to a 5- to 20-membered (e.g., 5- to 14-membered, 5- to 8-membered, or 5- to 6-membered) aromatic or non-aromatic monocyclic, bicyclic, or polycyclic ring system having 1-4 heteroatom ring members independently selected from N, O, or S. One or more N, C, or S atoms in the heterocycle can be oxidized. Preferably, the heterocycle is a 5- to 10-membered ring system, either monocyclic or fused bicyclic. Representative examples include, but are not limited to, pyrrolidine, azetidine, piperidine, morpholine, tetrahydrofuran, tetrahydropyran, benzofuran, benzothiophene, indole, benzopyrazole, pyrrole, thiophene, furan, thiazole, imidazole, pyrazole, pyrimidine, pyridine, pyrazine, pyridazine, isothiazole, and isoxazole. It should be understood that this term encompasses heteroaryl as defined herein.

The term "aryl" refers to a monocyclic or polycyclic aromatic hydrocarbyl group having 6-20, e.g., 6-12, carbon atoms in the ring moiety. Preferably, the aryl group is ($C_6$-$C_{10}$) aryl. Non-limiting examples include phenyl, biphenyl, naphthyl, or tetrahydronaphthyl, each of which may be optionally substituted with 1-4 substituents, e.g., alkyl, trifluoromethyl, cycloalkyl, halogen, hydroxy, alkoxy, acyl, alkyl-C(O)—O—, aryl-O—, heteroaryl-O—, amino, sulfhydryl, alkyl-S—, aryl-S—, nitro, cyano, carboxyl, alkyl-O—C(O)—, carbamoyl, alkyl-S(O)—, sulfonyl, sulfonamido, heterocyclyl, and the like.

The term "heteroaryl" refers to a 5- to 20-membered (e.g., 5- to 14-membered, 5- to 8-membered, 5- to 6-membered) aromatic monocyclic or polycyclic ring system containing 1-4 heteroatoms selected from N, O, or S, which may be substituted or unsubstituted. Preferably, the heteroaryl group is a 5- to 10-membered ring system, either monocyclic or fused bicyclic. Representative heteroaryl groups include 2- or 3-thienyl, 2- or 3-furanyl, 2- or 3-pyrrolyl, 2-, 4- or 5-imidazolyl, 3-, 4- or 5-pyrazolyl, 2-, 4- or 5-thiazolyl, 3-, 4- or 5-isothiazolyl, 2-, 4- or 5-oxazolyl, 3-, 4- or 5-isoxazolyl, 3- or 5-1,2,4-triazolyl, 4- or 5-1,2,3-triazolyl, tetrazolyl, 2-, 3- or 4-pyridyl, 3- or 4-pyridazinyl, 3-, 4- or 5-pyrazinyl, 2-pyrazinyl, and 2-, 4- or 5-pyrimidinyl.

The term "heteroalkyl" refers to a stable linear or branched hydrocarbon consisting of a specified number of carbon atoms and one to ten, preferably one to three, heteroatoms selected from O, N, Si, and S, either fully saturated or containing 1-3 units of unsaturation, wherein the nitrogen and sulfur atoms may optionally be oxidized and the nitrogen heteroatom may optionally be quaternized. The heteroatoms 0, N, Si, and S can be located at any internal position of the heteroalkyl group or at the position where the heteroalkyl group is linked to the rest of the molecule. Representative examples of the heteroalkyl group include —CH2-CH2-O—CH3, —CH2-CH2-NH—CH3, —CH2-CH2-N(CH3)-CH3, —CH2-S—CH2-CH3, —CH2-CH2-S(O)—CH3, —NH—CH2-CH2-NH—C(O)—CH2-CH3, —CH2-CH2-S(O)2-CH3, —CH═CH—O—CH3, —Si(CH3)3, —CH2-CH═N—O—CH3, and —CH═CH—N(CH3)-CH3. Up to two heteroatoms may be consecutive, e.g., —CH2-NH—OCH3 and —CH2-O—Si(CH3)3. In general, the $C_1$-$C_4$ heteroalkyl or heteroalkylene group has 1-4 carbon atoms and 1 or 2 heteroatoms and the $C_1$-$C_3$ heteroalkyl or heteroalkylene group has 1-3 carbon atoms and 1 or 2 heteroatoms. In some aspects, the heteroalkyl and heteroalkylene groups are saturated.

Unless otherwise indicated, the term "substituted" as used herein in the definition of each group means that the corresponding group may be substituted with, for example, but not limited to, the following groups: alkyl, alkenyl, alkynyl, cycloalkyl, aryl, heteroaryl, heterocyclyl, halogen, cyano, nitro, azido, carboxyl, hydroxy, sulfhydryl, amino, mono- or dialkylamino, mono- or dicycloalkylamino, mono- or diarylamino, mono- or diheteroylamino, mono- or diheteroarylamino, alkyl- or cycloalkyl- or heterocyclyl- or heteroaryl- or aryl-oxy, alkyl- or cycloalkyl- or heterocyclyl- or heteroaryl- or aryl-thio, alkyl- or cycloalkyl- or heterocyclyl- or heteroaryl- or aryl-acyl, alkyl- or cycloalkyl- or heterocyclyl- or heteroaryl- or aryl-acylamino, alkyl- or cycloalkyl- or heterocyclyl- or heteroaryl- or aryl-acyloxy, alkyl- or cycloalkyl- or heterocyclyl- or heteroaryl- or aryl-sulfonyl, alkyl- or cycloalkyl- or heterocyclyl- or heteroaryl- or aryl-sulfonyloxy, alkyl- or cycloalkyl- or heterocyclyl- or heteroaryl- or aryl-sulfonylamino, or the amino-formyl groups optionally substituted as described above, and respective groups thereof further substituted by the remaining optional substituents, wherein the respective groups are as defined herein. Examples of substituents include, but are not limited to, one or more groups independently selected from the following: halogen, OH, SH, CN, $NH_2$, $NHCH_3$, $N(CH_3)_2$, $NO_2$, $N_3$, $C(O)CH_3$, COOH, C(O)-amino, $OCOCH_3$, methyl, ethyl, propyl, isopropyl, butyl, isobutyl, sec-butyl, tert-butyl, cyclopropyl, methoxy, ethoxy, propoxy, oxo, trifluoromethyl, difluoromethyl, sulfonylamino, methylsulfonylamino, SO, $SO_2$, phenyl, piperidinyl, piperazinyl, and pyrimidinyl.

The term "substitution" or "substituted" as used herein means that one or more (e.g., 1, 2, 3, or 4) hydrogens on a specified atom are replaced with a designated group, provided that the normal valency of the specified atom under the present circumstances is not exceeded and a stable compound is formed, and the combination of a substituent and a variable is permitted only when such a combination forms a stable compound.

As used herein, the term "linker" refers to a bifunctional moiety that links a drug to an antibody in a drug-antibody conjugate. The linker of the present invention may have multiple components (e.g., in some embodiments, a linking group responsible for coupling to an antibody; a degradable peptide unit; and optionally a spacer group).

As used herein, the term "PEG unit" refers to an organic moiety comprising repeating ethylene-oxy subunits (PEG or PEG subunits), which may be polydisperse, monodisperse, or discrete (i.e., having a discrete number of ethylene-oxy subunits). Polydisperse PEG is a heterogeneous mixture of various sizes and molecular weights, whereas monodisperse PEG is generally purified from a heterogeneous mixture and thus has unique chain length and molecular weight. The PEG unit comprises discrete PEG, which is a compound synthesized in a stepwise manner rather than through a polymerization process. The discrete PEG provides a single molecule with a defined and specified chain length.

The term "pharmaceutically acceptable salt" refers to salts that retain the biological effects and properties of the ADCs of the present invention and are not biologically or otherwise undesired. The ADCs of the present invention may exist in their pharmaceutically acceptable salt forms, including acid addition salts and base addition salts. In the present invention, pharmaceutically acceptable non-toxic acid addition salts refer to salts formed by reaction of the ADCs of the present invention with organic or inorganic acids including, but not limited to, hydrochloric acid, sulfuric acid, hydrobromic acid, hydroiodic acid, phosphoric acid, nitric acid, perchloric acid, acetic acid, oxalic acid, maleic acid, fumaric acid, tartaric acid, benzenesulfonic acid, methanesulfonic acid, salicylic acid, succinic acid, citric acid, lactic acid, propionic acid, benzoic acid, p-toluenesulfonic acid, malic acid, and the like. Pharmaceutically acceptable non-toxic base addition salts refer to salts formed by the ADCs of the present invention with organic or inorganic bases including, but not limited to, alkali metal salts, e.g., lithium, sodium or potassium salts; alkaline earth metal salts, e.g., calcium or magnesium salts; organic base salts, e.g., ammonium salts, formed with N group-containing organic bases.

The term "solvate" refers to an association compound formed by the ADC of the present invention with one or more solvent molecules. Solvents for forming solvates include, but are not limited to, water, methanol, ethanol, isopropanol, ethyl acetate, tetrahydrofuran, N,N-dimethylformamide, dimethylsulfoxide, and the like.

"Pharmaceutically acceptable" and "pharmaceutical" are used interchangeably herein, provided that there is no contradiction according to the context.

The term "drug-to-antibody ratio" or "DAR" refers to the ratio of the drug moiety (D) conjugated to the Ab moiety described herein to the Ab moiety in an ADC. In some embodiments described herein, DAR may be determined by q in formula I, for example, the DAR may be 1-20, e.g., 2-18, 4-16, 5-12, 6-10, 2-8, 3-8, 2-6, 4-6, 6-10, e.g., 2, 3, 4, 5, 6, 7, 8, 9, 10, 11, 12, 13, 14, or 15. DAR may also be calculated as the average DAR of the molecular population in the product, i.e., the overall ratio of the small molecule drug moiety (D) conjugated to the Ab moiety described herein to the Ab moiety in the product as measured by detection methods (e.g., by conventional methods such as mass spectrometry, ELISA assay, electrophoresis, and/or HPLC), and such DAR is referred to herein as average DAR. In some embodiments, the average DAR value of the conjugate of the present invention is 1-20, e.g., 2-18, 4-16, 5-12, 6-10, 2-8, 3-8, 2-6, 4-6, or 6-10, e.g., 1.0-8.0 or 2.0-6.0, e.g., 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0, and ranges with any two of these values as endpoints.

The term "drug" as used herein encompasses any substance that is effective in preventing or treating tumors, e.g., cancer, including chemotherapeutic agents, cytokines, angiogenesis inhibitors, cytotoxic agents, other antibodies, small molecule drugs, or immunomodulatory agents (e.g., immunosuppressive agents).

The term "cytotoxic agent" as used herein refers to a substance that inhibits or prevents cell functions and/or causes cell death or destruction. Examples of cytotoxic agents include, but are not limited to, camptothecin drugs, auristatin, aureomycin, maytansinoids, ricin, ricin A chain, combrestatin, duocarmycin, aplysiatoxin, doxorubicin, daunomycin, taxol, cisplatin, cc1065, ethidium bromide, mitomycin, etoposide, tenoposide, vincristine, vinblastine, colchicine, dihydroxy anthracin dione, actinomycin, diphtherin, pseudomonas exotoxin (PE) A, PE40, abrin, abrin A chain, modeccin A chain, α-sarcin, gelonin, mitogellin, retstrictocin, phenomycin, enomycin, curicin, crotin, calicheamicin, *Sapaonaria officinalis* inhibitors and glucocorticoids and other therapeutic agents, and radioisotopes, e.g., At211, I131, I125, Y90, Re186, Re188, Sm153, Bi212 or 213, P32, and radioisotopes of Lu, including Lu177.

The term "small molecule drug" refers to a low molecular weight organic compound capable of regulating biological processes. "Small molecule" is defined as a molecule with a molecular weight of less than 10 kD, generally less than 2 kD and preferably less than 1 kD. The small molecule includes, but is not limited to, inorganic molecules, organic molecules, organic molecules containing inorganic components, molecules containing radioactive atoms, synthetic molecules, peptide mimetics, and antibody mimetics. As therapeutic agents, small molecules penetrate cells better, are less susceptible to degradation and are less likely to induce an immune response compared with large molecules.

The term "pharmaceutical composition" refers to a composition that exists in a form allowing effective biological activity of the active ingredient contained therein, and does not contain additional ingredients having unacceptable toxicity to a subject to which the composition is administered.

The term "pharmaceutical auxiliary material" refers to diluents, adjuvants (e.g., Freund's adjuvants (complete and incomplete)), excipients, carriers, stabilizers, or the like, which are administered with the active substance.

The term "pharmaceutical combination" or "combination product" refers to a non-fixed combination product or a fixed combination product, including but not limited to a kit and a pharmaceutical composition. The term "non-fixed combination" means that the active ingredients (e.g., (i) the ADC molecule of the present invention or the antibody of the present invention, and (ii) an additional therapeutic agent) are administered, either simultaneously or sequentially (without specific time limitation or at identical or different time intervals), to a patient as separate entities, wherein such administration provides two or more prophylactically or therapeutically effective active agents in the patient. In some embodiments, the ADC molecule of the present invention or the antibody of the present invention and the additional therapeutic agent used in the pharmaceutical combination are administered at levels that do not exceed their levels when used alone. The term "fixed combination" means that two or more active agents are administered to a patient simultaneously as a single entity. The dose and/or time intervals of two or more active agents are preferably selected such that the combined use of the components can result in a therapeutic effect on the disease or disorder which is greater than that achieved by the use of either component alone. The ingredients may each take a separate formulation form and such separate formulation forms may be identical or different.

The term "combination therapy" refers to the administration of two or more therapeutic agents or modalities (e.g., radiotherapy or surgery) to treat the diseases described herein. Such administration includes co-administration of these therapeutic agents in a substantially simultaneous manner, for example, in a single capsule with a fixed proportion of active ingredients. Alternatively, such administration includes co-administration of the active ingredients in a variety of or separate containers (such as tablets, capsules, powder, and liquid). The powder and/or liquid can be reconstituted or diluted to a desired dose before administration. In addition, such administration also includes using each type of the therapeutic agents at approximately the same time or in a sequential manner at different times. In any case, the therapeutic regimen will provide the beneficial effect of the pharmaceutical combination in the treatment of disorders or symptoms described herein.

Herein, the terms "individual" and "subject" are used interchangeably to refer to a mammal. Mammals include, but are not limited to, domesticated animals (e.g., cows, sheep, cats, dogs, and horses), primates (e.g., human and non-human primates such as monkeys), rabbits, and rodents (e.g., mice and rats). In particular, the subject is a human.

The terms "tumor" and "cancer" are used interchangeably herein to refer to a physiological disease in mammals that is generally characterized by unregulated cell growth. In certain embodiments, cancers suitable for treatment with the antibody of the present invention include gastric cancer, pancreatic cancer, or esophagogastric junction adenocarcinoma, including metastatic forms of such cancers. This term also encompasses all neoplastic cell growth and proliferation, whether malignant or benign, and all pre-cancerous and cancerous cells and tissues.

The term "anti-tumor effect" refers to a biological effect that can be demonstrated by a variety of means, including but not limited to, for example, decrease in tumor volume, decrease in number of tumor cells, decrease in tumor cell proliferation, or decrease in tumor cell viability.

As used herein, "treatment" (or "treat" or "treating") refers to slowing, interrupting, arresting, alleviating, stopping, lowering, or reversing the progression or severity of an existing symptom, disorder, condition, or disease.

As used herein, "prevention" (or "prevent" or "preventing") includes the inhibition of the development or progression of symptoms of a disease or disorder, or a specific disease or disorder. In some embodiments, subjects with a family history of cancer are candidates for preventive regimens. Generally, in the context of cancer, the term "prevention" (or "prevent" or "preventing") refers to the administration of a drug prior to the onset of signs or symptoms of cancer, particularly in subjects at risk of cancer.

As used herein, the term "effective amount" refers to an amount or dose of the antibody-drug conjugate or the composition or combination thereof of the present invention that generates expected effects in a patient in need of treatment or prevention after administration to the patient in a single dose or multiple doses.

As used herein, the term "therapeutically effective amount" refers to an amount effective to achieve the desired therapeutic result at the required dosage and for the required period of time. The therapeutically effective amount is also such an amount that any toxic or adverse effect of the antibody-drug conjugate or the composition or combination thereof of the present invention is inferior to the therapeutically beneficial effect. The "therapeutically effective amount" preferably achieves an inhibition in a measurable parameter (e.g., tumor volume) of at least about 30%, even more preferably at least about 40%, 45%, 50%, 55%, 60%, 65%, 70%, 75%, 80%, 85%, 90%, or even 100% relative to an untreated individual.

As used herein, the term "prophylactically effective amount" refers to an amount effective to achieve the desired prophylactic result at the required dosage and for the required period of time. Generally, since a prophylactic dose is administered in a subject before or at an earlier stage of a disease, the prophylactically effective amount will be less than the therapeutically effective amount.

In the present invention, the term "CLDN18.2-positive" tumor refers to a tumor in which at least a part of cancer cells in the tumor organ or tissue are positive for CLDN18.2 cell surface expression. In some embodiments, the proportion of CLDN18.2-positive cancer cells in the cancer tissue or cancer cell population is at least 10% or 20%, preferably at least 30%, 40%, 50%, 60%, 70%, 75% or 80%. In still other embodiments, at least 40% or at least 50%, preferably 60%, 70%, 80% or 90% of the cancer cells in the tumor tissue or organ are positive for CLDN18.2 surface expression. In some embodiments, a cancer subject treated according to the method of the present invention has an increased level of CLDN18.2 cell surface expression in the diseased tissue or organ, e.g., by at least 10%, particularly by at least 20%, at least 50%, at least 100%, at least 200% or more, as compared to the corresponding tissue or organ in a healthy subject. In one embodiment, the CLDN18.2-positive tumor is selected from: gastric cancer, esophageal cancer, pancreatic cancer, lung cancer (e.g., non-small cell lung cancer (NSCLC)), ovarian cancer, colon cancer, liver cancer, head and neck cancer, and gallbladder cancer, and metastases thereof, particularly metastasis of gastric cancer. In one embodiment, the cancer is adenocarcinoma, particularly advanced adenocarcinoma. Particularly preferred cancer diseases are adenocarcinomas of the stomach, esophagus, pancreatic duct, bile duct, lung and ovary. In some embodiments, the cancer treated according to the present invention is HER-negative. In yet another embodiment, the CLDN18.2-positive tumor is a digestive system cancer or a cancer metastasis thereof. In one embodiment, the cancer is selected from gastric cancer, esophageal cancer (particularly lower esophageal cancer), esophagogastric junction adenocarcinoma, and gastroesophageal cancer. In a preferred embodiment, the cancer is, for example, a CLAUDIN 18.2-positive and HER2-negative gastric cancer. In another preferred embodiment, the cancer is gastroesophageal cancer, such as metastatic, refractory or recurrent advanced gastroesophageal cancer, and in yet another embodiment, the cancer is metastatic gastric cancer or esophagogastric junction adenocarcinoma (EGJA).

Aspects of the present invention will be described in further detail in the following subsections.

ADC Moiety of the Present Invention

I. Antibody-Drug Conjugate

In one aspect, the present invention provides an antibody-drug conjugate (ADC) having the following formula (I), or a pharmaceutically acceptable salt or solvate thereof:

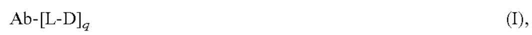

$$\text{Ab-[L-D]}_q \quad \text{(I),}$$

wherein

Ab represents an anti-Claudin18.2 antibody,

L represents a linker,

D represents a cytotoxic or cytostatic drug, e.g., a topoisomerase I inhibitor, and q represents an integer or decimal of 1-20, e.g., q=1-10, 1-8, 2-8, 4-8, or 6-8.

Components of the ADCs of the present invention and the ADCs of the present invention consisting of the components are separately described in detail below. It will be understood by those skilled in the art that any combination of any of the technical features of these components is within the contemplation of the present invention, unless otherwise expressly stated to the contrary. Furthermore, it will be understood by those skilled in the art that the ADCs of the present invention may comprise any such combination of features, unless otherwise expressly stated to the contrary.

Ab Unit of Antibody

The present inventors have made intensive studies to develop and provide a humanized anti-Claudin18.2 monoclonal antibody with excellent properties. As shown in the examples, the antibody of the present invention not only exhibits high binding affinity and high specificity for cells expressing human Claudin18.2 on the surface (particularly cells with low surface expression abundance), but also has advantageous properties such as Claudin18.2 antigen-mediated endocytic activity, stability, and/or pharmacokinetic properties, thus being suitable as a molecular component to be conjugated with a cytotoxic drug to form an antibody-drug conjugate. As shown in the examples, the ADC formed from the antibody of the present invention exhibits potent in-vivo tumor killing effects while having good drug tolerability.

Thus, in some aspects, the present invention provides an antibody-drug conjugate (ADC) comprising the antibody of the present invention that specifically binds to Claudin18.2 as an Ab unit of the conjugate of formula I of the present invention.

In some embodiments, Ab in formula (I) of the present invention comprises three CDRs of a heavy chain variable region (VH) sequence of SEQ ID NO: 1 or 3 and three CDRs of a light chain variable region (VL) sequence of SEQ ID NO: 2, wherein preferably, the CDRs are defined according to Kabat or IMGT, or a combination thereof.

In some embodiments, Ab in formula (I) of the present invention comprises 3 heavy chain complementarity determining regions (HCDRs) and 3 light chain complementarity determining regions (LCDRs), wherein (i) according to the IMGT scheme, the HCDR1 comprises or consists of an amino acid sequence of SEQ ID NO: 6, the HCDR2 comprises or consists of an amino acid sequence of SEQ ID NO: 7, the HCDR3 comprises or consists of an amino acid sequence of SEQ ID NO: 8, the LCDR1 comprises or consists of an amino acid sequence of SEQ ID NO: 9, the LCDR2 comprises or consists of an amino acid sequence of EAS, and the LCDR3 comprises or consists of an amino acid sequence of SEQ ID NO: 11; or (ii) according to the Kabat scheme, the HCDR1 comprises or consists of an amino acid sequence of SEQ ID NO: 12, the HCDR2 comprises or consists of an amino acid sequence of SEQ ID NO: 13, the HCDR3 comprises or consists of an amino acid sequence of SEQ ID NO: 14, the LCDR1 comprises or consists of an amino acid sequence of SEQ ID NO: 15, the LCDR2 comprises or consists of an amino acid sequence of SEQ ID NO: 16, and the LCDR3 comprises or consists of an amino acid sequence of SEQ ID NO: 17.

In one embodiment, Ab in formula (I) of the present invention comprises heavy and light chain variable region sequences or variants thereof of any one of the exemplary antibodies 25C7A5-HZ1 and -HZ2 of the present invention; for example, it is an antibody having the same CDR sequences as one of the exemplary antibodies, and having the same or different framework region sequences.

In one embodiment, Ab in formula (I) of the present invention comprises a heavy chain variable region, wherein the heavy chain variable region comprises:

an amino acid sequence set forth in SEQ ID NO: 1 or an amino acid sequence having at least 80%, 85%, 90%, 95%, 96%, 97%, 98% or 99% sequence identity thereto; or an amino acid sequence set forth in SEQ ID NO: 3 or an amino acid sequence having at least 80%, 85%, 90%, 95%, 96%, 97%, 98% or 99% sequence identity thereto.

In one embodiment, Ab in formula (I) of the present invention comprises a light chain variable region, wherein the light chain variable region comprises:

an amino acid sequence set forth in SEQ ID NO: 2 or an amino acid sequence having at least 80%, 85%, 90%, 95%, 96%, 97%, 98% or 99% sequence identity thereto.

In some preferred embodiments, Ab in formula (I) of the present invention comprises a heavy chain variable region and a light chain variable region, wherein the heavy chain variable region comprises an amino acid sequence set forth in SEQ ID NO: 1 or 3 or an amino acid sequence having at least 95%, 96%, 97%, 98% or 99% sequence identity thereto, and the light chain variable region comprises an amino acid sequence set forth in SEQ ID NO: 2 or an amino acid sequence having at least 95%, 96%, 97%, 98% or 99% sequence identity thereto. Preferably, the sequences of the antibody are humanized. More preferably, the heavy chain variable region of the antibody has a framework region sequence derived from a human germline, and preferably has amino acid Q or E, preferably amino acid Q, at position H6 numbered according to the Kabat scheme in the heavy chain variable region.

In still other preferred embodiments, Ab in formula (I) of the present invention comprises a heavy chain variable region of SEQ ID NO: 1 and a light chain variable region of SEQ ID NO: 2.

In still other preferred embodiments, Ab in formula (I) of the present invention comprises a heavy chain variable region of SEQ ID NO: 3 and a light chain variable region of SEQ ID NO: 2.

In some embodiments, Ab in formula (I) of the present invention preferably further comprises a heavy chain constant region and/or a light chain constant region of the antibody.

Preferably, the heavy chain constant region is a heavy chain constant region derived from a human immunoglobulin. Preferably, the light chain constant region is a light chain constant region derived from a human immunoglobulin. In some aspects, the heavy chain constant region contained in Ab may be of any isotype or subtype, e.g., a heavy chain constant region of IgG1, IgG2, IgG3 or IgG4 isotype, preferably an IgG1, IgG2 or IgG4 heavy chain constant region, particularly a human IgG1 heavy chain constant region. In still other aspects, the light chain constant region contained in Ab may be a κ light chain constant region or a λ light chain constant region, particularly a human κ light chain constant region.

In some embodiments, Ab in formula (I) of the present invention comprises a human IgG1 heavy chain constant region. Preferably, the heavy chain constant region comprises an amino acid sequence of SEQ ID NO: 4, or an amino acid sequence comprising at least one, two or three but no more than 20, 10 or 5 amino acid alterations relative to the amino acid sequence of SEQ ID NO: 4, or a sequence having at least 95%-99% identity to the amino acid sequence of SEQ ID NO: 4.

In some embodiments, Ab in formula (I) of the present invention comprises a human κ light chain constant region. Preferably, the light chain constant region comprises an amino acid sequence of SEQ ID NO: 5, or an amino acid sequence comprising at least one, two or three but no more than 20, 10 or 5 amino acid alterations relative to the amino acid sequence of SEQ ID NO: 5, or a sequence having at least 95%-99% identity to the amino acid sequence of SEQ ID NO: 5.

In some embodiments, Ab in formula (I) of the present invention is a full-length antibody comprising a heavy chain constant region and a light chain constant region. In some embodiments, Ab in formula (I) of the present invention has a tetrameric structure formed by two light chains and two heavy chains. In still other embodiments, Ab in formula (I) of the present invention is an IgG antibody, particularly an IgG1 antibody. In a further embodiment, Ab in formula (I) of the present invention is a humanized antibody.

In some preferred embodiments, Ab in formula (I) of the present invention comprises a heavy chain and a light chain, wherein the heavy chain comprises or consists of an amino acid sequence set forth in SEQ ID NO: 18 or 19 or an amino acid sequence having at least 80%, 85%, 90%, 95%, 96%, 97%, 98% or 99% sequence identity thereto. In other preferred embodiments, Ab in formula (I) of the present invention comprises a heavy chain and a light chain, wherein the light chain comprises an amino acid sequence set forth in SEQ ID NO: 20 or an amino acid sequence having at least 80%, 85%, 90%, 95%, 96%, 97%, 98% or 99% sequence identity thereto.

In some more preferred embodiments, Ab in formula (I) of the present invention comprises a heavy chain and a light chain selected from:

(a) a heavy chain comprising an amino acid sequence of SEQ ID NO: 18, and a light chain comprising an amino acid sequence of SEQ ID NO: 20; and (b) a heavy chain comprising an amino acid sequence of SEQ ID NO: 19, and a light chain comprising an amino acid sequence of SEQ ID NO: 20.

Variants of any of the above antibodies are also contemplated by the present invention. The antibody variants of the present invention preferably retain at least 60%, 70%, 80%, 90%, or 100% of the biological activity (e.g., antigen-binding ability) of the antibody prior to alterations. More preferably, the alterations do not result in loss of binding ability of the antibody variants to an antigen, but optionally confer properties such as increased affinity for the antigen and different effector functions. It will be understood that the heavy or light chain variable regions or CDRs of the antibody may be altered independently or in combination. In addition, the Fc region of the antibody may also be altered. The alterations in the Fc region may be made alone or in combination with the alterations in the framework regions and/or CDRs described above. The Fc region may be altered, for example, to alter one or more functions of the antibody, such as serum half-life, complement fixation, Fc receptor binding, and/or antigen-dependent cytotoxicity. In addition, the antibody of the present invention may be chemically modified (e.g., linked to PEG), or its glycosylation pattern may be altered.

To form an ADC, the antibody according to the present invention may be conjugated to a toxin-linker using some natural conjugation sites on the antibody. Such natural conjugation sites include a sulfhydryl group of cysteine and an amino group of lysine. Typically, a more defined drug-to-antibody ratio (DAR) can be achieved by using disulfide bridges between the heavy and light chains of the antibody. Thus, in one embodiment, after reduction of the interchain disulfide bonds of the antibody, toxins are conjugated to the antibody of the present invention by sulfhydryl chemistry to form an ADC of formula (I). In addition, it is also contemplated to introduce artificial conjugation sites into the antibody to achieve more site-directed conjugation.

Drug D Unit

A drug D unit of the antibody-drug conjugate is also referred to herein as a payload of an ADC drug. The drug D that can be used in the ADC of the present invention is not particularly limited, and may be any drug that is toxic or inhibitory to cells or a prodrug thereof. Those skilled in the art can select a suitable drug molecule as the payload of the ADC based on the desired ADC drug action mechanism and cell killing effect.

In some embodiments, the drug D is a cytotoxic agent. A variety of cytotoxic agents suitable for use as payloads with different mechanisms have been reported in the art, including, but not limited to:

(1) microtubule inhibitors/disruptors: for example, but not limited to, auristatins (e.g., MMAE or MMAF), maytansine derivatives (e.g., DM2, DM4), tubulysins, cryptomycins, and anti-mitotic EG5 inhibitors (e.g., kinesin spindle protein (KSP) inhibitors);

(2) DNA damaging agents: for example, but not limited to, pyrrolobenzodiazepines (e.g., pyrrolo[2,1-c][1,4] benzodiazepine (PBD)), duocarmycins, indolinobenzodiazepine, duocarmycins, and calicheamicins;

(3) topoisomerase inhibitors: for example, but not limited to, camptothecins (e.g., exatecan and its derivative Dxd); and (4) other cytotoxic agents: apoptosis inducers (Bcl-xL inhibitor), thailanstatin and analogs thereof, amatoxin, nicotinamide phosphoribosyltransferase (NAMPT) inhibitors, and carmaphycin.

The drug D in the formula (I) of the present invention may be any compound selected from the above. In some embodiments, the drug D is an anti-tumor growth inhibitor selected from maytansine derivatives, calicheamicin derivatives, and auristatin derivatives. In one embodiment, the drug D is a tubulin inhibitor/stability disruptor, such as vinca alkaloids, vincristine, paclitaxel, and docetaxel. In one embodiment, the drug D is a DNA synthesis inhibitor, such as methotrexate, 5-fluorouracil, cytarabine, gemcitabine, mercaptopurine, pentostatin, fludarabine, and cladribine. In one embodiment, the drug D is a DNA topoisomerase inhibitor, such as a topoisomerase I inhibitor (e.g., camptothecins) and a topoisomerase II inhibitor (e.g., actinomycin D, adriamycin, mitoxantrone).

In some preferred embodiments, the drug D of the ADC according to the present invention is a topoisomerase I inhibitor. Atypical example of the topoisomerase I inhibitor is a camptothecin drug, for example, but not limited to, camptothecin (CPT), hydroxycamptothecin, 9-aminocamptothecin, exatecan, topotecan, belotecan, irinotecan, SN-38, and FL118, and derivatives thereof. See, e.g., Vesela Kostova et al, The Chemistry Behind ADCs, Pharmaceuticals 2021, 14, 442. https://doi.org/10.3390/ph14050442; and WO2019/195665, which are incorporated herein by reference.

In some embodiments of the present invention, the drug D of the ADC of the present invention is a camptothecin drug selected from:

camptothecin and derivatives thereof, e.g.,

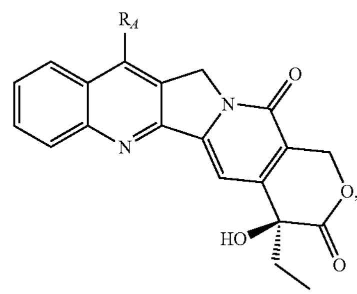

wherein $R_A$ is selected from, for example, hydrogen and alkyl optionally substituted with a substituent, wherein the substituent includes, but is not limited to, hydroxy and amino, wherein the amino moiety or the hydroxy moiety may be unsubstituted or substituted with, for example, alkyl, alkylacyl, or alkylsulfonyl; in one embodiment, the drug D is

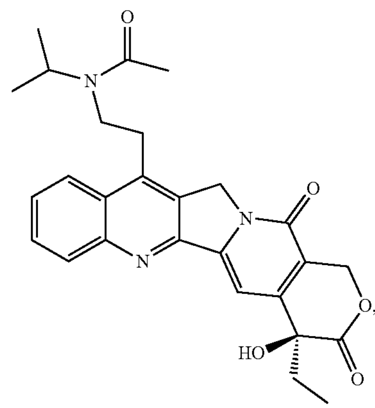

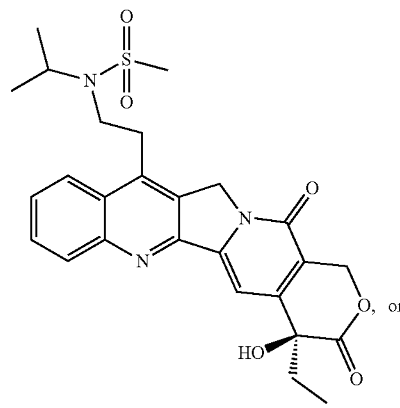

or

-continued

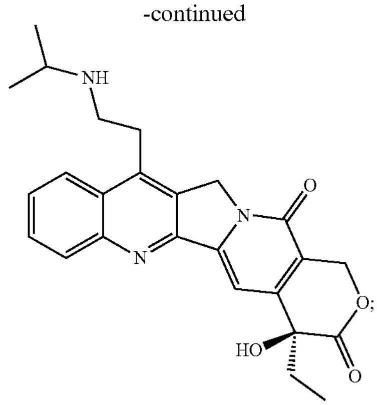

10,11-methylenedioxy CPT (also abbreviated as MDCPT or FL118) and derivatives thereof, e.g.,

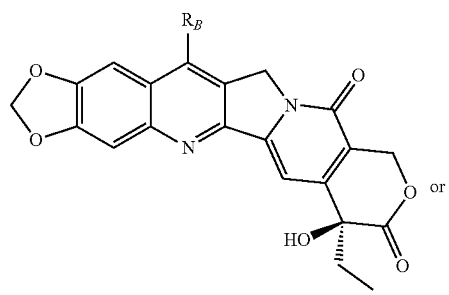

or

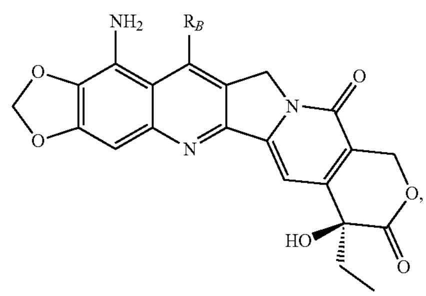

wherein $R_B$ is selected from, for example, hydrogen, cycloalkyl, phenyl, and alkyl optionally substituted with a substituent, wherein the substituent includes, but is not limited to, halogen, hydroxy, optionally substituted alkoxy, cycloalkyl, heterocycloalkyl, phenyl, and amino, wherein the amino moiety may be optionally substituted; in one embodiment, the drug D is

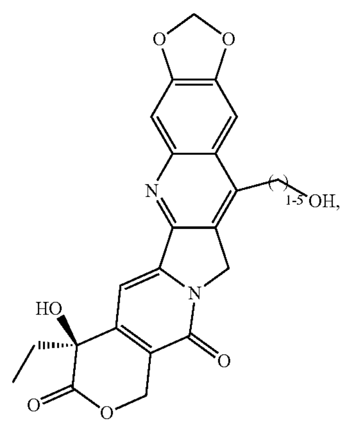

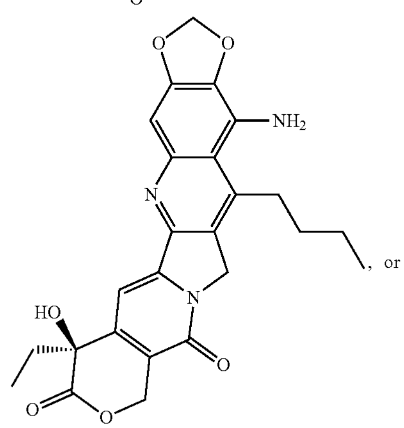

or

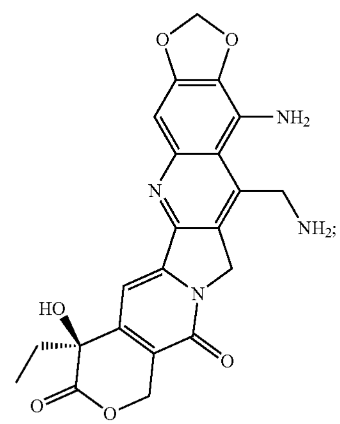

10-hydroxy CPT (also abbreviated as HCPT) and derivatives thereof, e.g.,

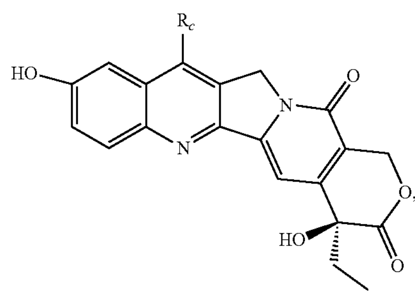

-continued

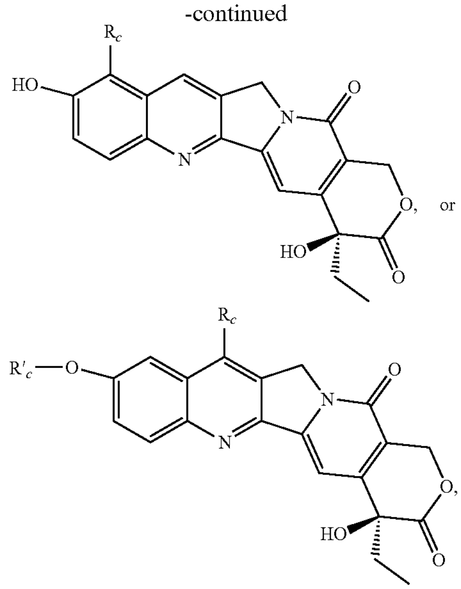

wherein $R_C$ is selected from, for example, optionally substituted alkyl and cycloalkyl; $R'_C$ is selected from, for example, H, alkylacyl, and optionally substituted heterocycloalkylacyl; in one embodiment, the drug D is 7-ethyl-10-hydroxy CPT (SN-38) or its prodrug irinotecan (CPT-11), or the drug D is topotecan.

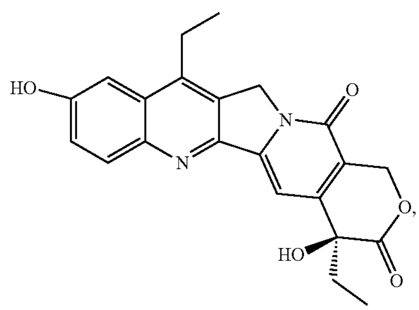

SN-38

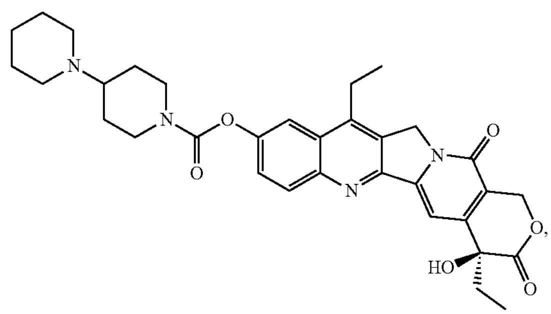

Irinotecan(CPT-11)

-continued

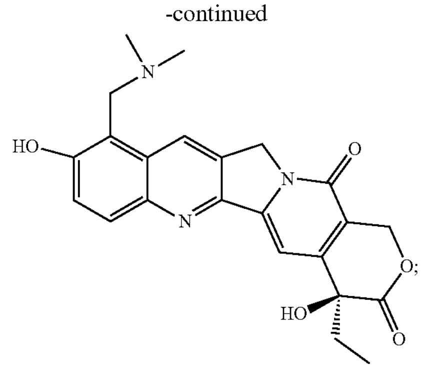

topotecan exatecan and derivatives thereof, e.g.,

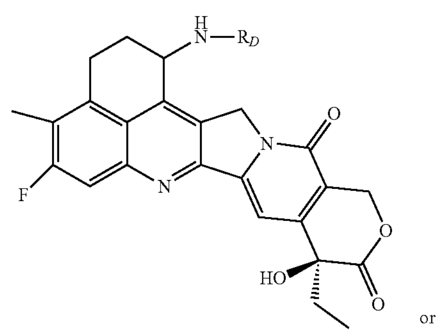

or

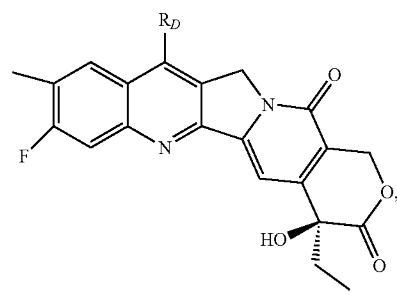

wherein $R_D$ is selected from, for example, H, alkyl optionally substituted with a substituent, and alkyl-C(=O)— optionally substituted with a substituent, wherein the substituent is, for example, —OH or substituted or unsubstituted amino; in one embodiment, the drug D is:

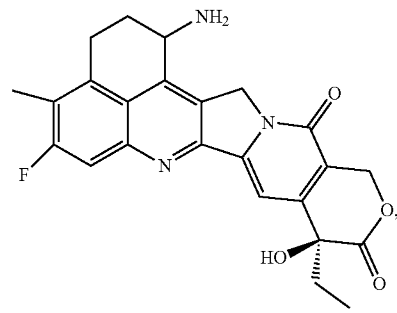

exatecan

-continued

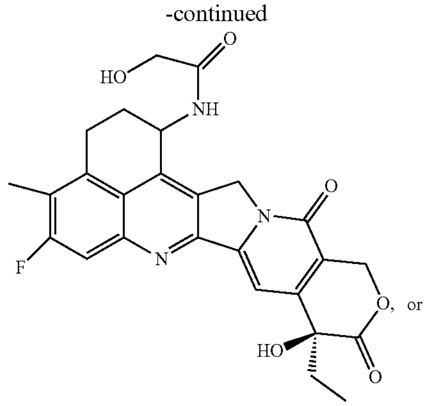

or

Dxd(1)

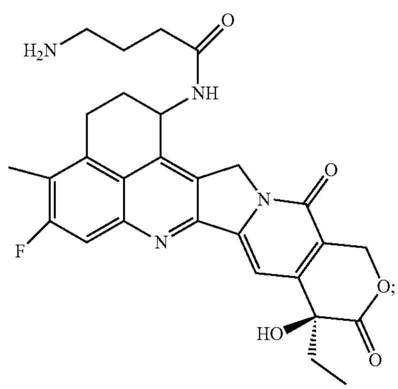

Dxd(2)

in another embodiment, the drug D is:

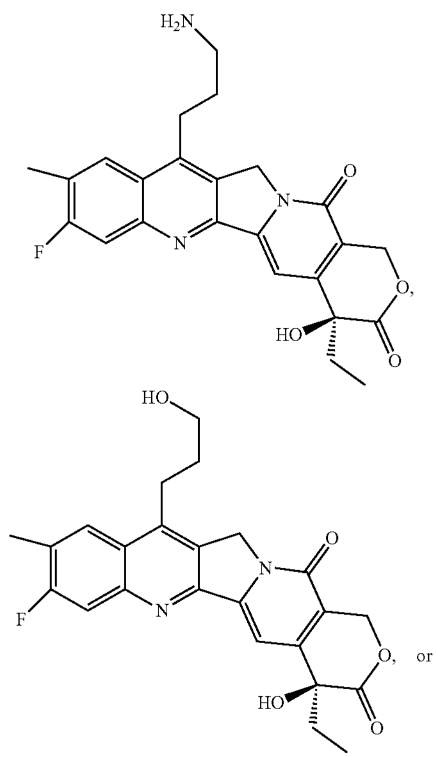

or

-continued

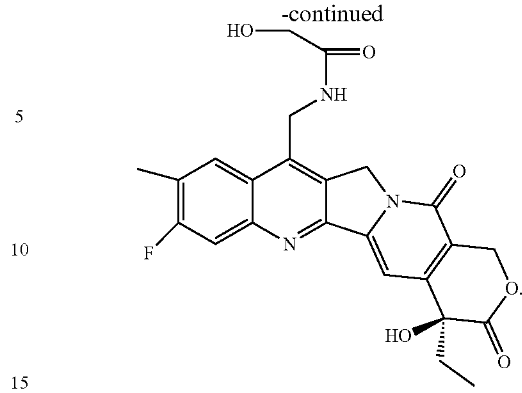

F118 ((20S)-10,11-methylenedioxy camptothecin) was obtained by high-throughput screening of compound libraries. FL118 has been demonstrated to have significantly higher in-vivo and in-vitro anti-cancer activity in many different cancer types as compared to other camptothecin derivatives. In addition to inhibiting topoisomerase I, FL118 can also selectively inhibit the gene promoter activity and endogenous expression of anti-apoptotic proteins such as survivin, XIAP, cIAP2, and Mcl-1. See Xiang Ling et al, A Novel Small Molecule FL118 That Selectively Inhibits Survivin, Mcl-1, XIAP and cIAP2 in a p53-Independent Manner, Shows Superior Antitumor Activity, PLoS ONE 7(9): e45571. doi:10.1371/journal.pone.0045571. Although the use of FL118 alone is severely hampered by its extremely poor water solubility and toxic side effects, as shown in the examples, the conjugate formed by combining the compound with the antibody and linker of the present invention not only effectively exerts the tumor killing effect of the compound, but also overcomes the drawbacks of the compound, and the formed conjugate has a low aggregation degree and good tolerance in animals.

Thus, in some preferred embodiments of the present invention, the drug D of the ADC of the present invention is an FL118 derivative, particularly position 7-substituted FL118.

In some embodiments, the drug D in formula (I) of the present invention is a camptothecin drug comprising the structure of formula D below:

(D)

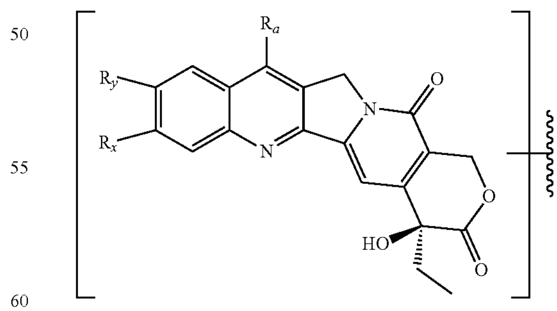

wherein $R_x$ and $R_y$ are each independently selected from H, halogen, —OH, and $C_1$-$C_6$ alkyl; or $R_x$ and $R_y$, together with the carbon atoms to which they are connected, form a 5- to 6-membered heterocycle having 1 or 2 atoms selected from N, S, and O;

$R_a$ is selected from H, halogen, —OH, optionally substituted $C_1$-$C_8$ alkyl or $C_3$-$C_8$ alkynyl or $C_3$-$C_8$ alkenyl, optionally substituted $C_1$-$C_8$ alkoxy, optionally substituted $C_3$-$C_8$ cycloalkyl, optionally substituted phenyl, optionally substituted heterocycloalkyl, and optionally substituted heteroaryl, wherein preferably, $R_a$ is selected from:

hydrogen;

$C_3$-$C_8$ cycloalkyl;

phenyl; and $C_1$-$C_8$ alkyl or $C_3$-$C_8$ alkynyl or $C_3$-$C_8$ alkenyl optionally substituted with a substituent selected from: halogen, hydroxy, $C_1$-$C_4$ alkoxy optionally substituted with $NH_2$, $NH(C_1$-$C_4$ alkyl) and $N(C_1$-$C_4$ $alkyl)_2$, $C_3$-$C_8$ cycloalkyl, heterocycloalkyl, phenyl, and $NR^1R^2$, wherein $R^1$ and $R^2$ are each independently selected from:

hydrogen;

$C_1$-$C_8$ alkyl optionally substituted with a substituent selected from: hydroxy, amino, amino substituted with one or two $C_1$-$C_4$ alkyl, amino substituted with one or two $C_1$-$C_4$ hydroxyalkyl, and amino substituted with ($C_1$-$C_4$ hydroxyalkyl) and ($C_1$-$C_4$ alkyl);

$C_1$-$C_4$ alkyl substituted with 1 or 2 $C_3$-$C_{10}$ cycloalkyl, $C_3$-$C_{10}$ heterocycloalkyl, phenyl or heteroaryl;

$C_3$-$C_{10}$ cycloalkyl;

$C_3$-$C_{10}$ heterocycloalkyl;

$C_2$-$C_6$ heteroalkyl;

heteroaryl;

optionally halogenated phenyl; and $C_1$-$C_8$ alkyl-C(=O)— optionally substituted with hydroxy or amino;

or, $R^1$ and $R^2$, in combination with the nitrogen atom to which they are connected, form a 5-, 6-, or 7-membered heterocycle having 0-3 substituents selected from halogen, $C_1$-$C_4$ alkyl, OH, $C_1$-$C_4$ alkoxy, $NH_2$, $NH(C_1$-$C_4$ alkyl), and $N(C_1$-$C_4$ $alkyl)_2$, wherein the cycloalkyl, heterocycloalkyl, phenyl and heteroaryl, at each occurrence, are each independently and optionally substituted with 0-3 substituents selected from: OH, $C_1$-$C_4$ alkyl, $C_1$-$C_4$ alkoxy, $NH_2$, $NH(C_1$-$C_4$ alkyl), and $N(C_1$-$C_4$ $alkyl)_2$.

In some preferred embodiments, $R_x$ and $R_y$ are each independently H. In other preferred embodiments, $R_x$ is F, and $R_y$ is methyl. In still other preferred embodiments, $R_x$ and $R_y$, together with the carbon atoms to which they are connected, form a 5-membered heterocycle containing two O atoms.

In some embodiments, the drug D in formula (I) of the present invention is a camptothecin drug comprising the structure of formula $D_a$ or formula $D_b$ below:

(Da)

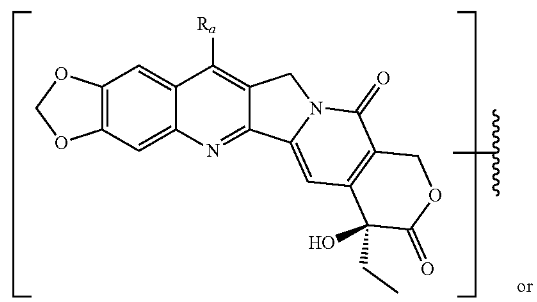

or

-continued (Db)

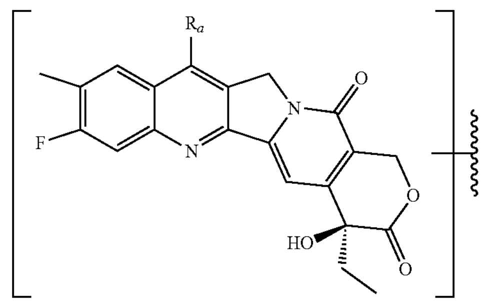

, particularly a camptothecin drug of formula ($D_a$), wherein $R_a$ is selected from:

hydrogen;

$C_3$-$C_8$ cycloalkyl;

phenyl; and $C_1$-$C_8$ alkyl, $C_3$-$C_8$ alkynyl or $C_3$-$C_8$ alkenyl optionally substituted with a substituent selected from: halogen, hydroxy, $C_1$-$C_4$ alkoxy optionally substituted with $NH_2$, $NH(C_1$-$C_4$ alkyl) and $N(C_1$-$C_4$ $alkyl)_2$, $C_3$-$C_8$ cycloalkyl, heterocycloalkyl, phenyl, and $NR^1R^2$, wherein $R^1$ and $R^2$ are each independently selected from:

hydrogen;

$C_1$-$C_8$ alkyl optionally substituted with a substituent selected from: hydroxy, amino, amino substituted with one or two $C_1$-$C_4$ alkyl, amino substituted with one or two $C_1$-$C_4$ hydroxyalkyl, and amino substituted with ($C_1$-$C_4$ hydroxyalkyl) and ($C_1$-$C_4$ alkyl);

$C_1$-$C_4$ alkyl substituted with 1 or 2 $C_3$-$C_{10}$ cycloalkyl, $C_3$-$C_{10}$ heterocycloalkyl, phenyl or heteroaryl;

$C_3$-$C_{10}$ cycloalkyl;

$C_3$-$C_{10}$ heterocycloalkyl;

$C_2$-$C_6$ heteroalkyl;

heteroaryl;

optionally halogenated phenyl; and $C_1$-$C_8$ alkyl-C(=O)— optionally substituted with hydroxy or amino;

or, $R^1$ and $R^2$, in combination with the nitrogen atom to which they are connected, form a 5-, 6-, or 7-membered heterocycle having 0-3 substituents selected from halogen, $C_1$-$C_4$ alkyl, OH, $C_1$-$C_4$ alkoxy, $NH_2$, $NH(C_1$-$C_4$ alkyl), and $N(C_1$-$C_4$ $alkyl)_2$, wherein the cycloalkyl, heterocycloalkyl, phenyl and heteroaryl, at each occurrence, are each independently and optionally substituted with 0-3 substituents selected from: OH, $C_1$-$C_4$ alkyl, $C_1$-$C_4$ alkoxy, $NH_2$, $NH(C_1$-$C_4$ alkyl), and $N(C_1$-$C_4$ $alkyl)_2$.

In some embodiments, $R_a$ is hydrogen.

In some embodiments, $R_a$ is $C_3$-$C_8$ cycloalkyl (e.g., cyclopropyl, cycloheptyl, and cyclopentyl).

In some embodiments, $R_a$ is phenyl. In other embodiments, $R_a$ is phenyl substituted with $NH_2$ or $NH(C_1$-$C_4$ alkyl).

In some embodiments, $R_a$ is $C_1$-$C_6$ alkyl, e.g., methyl, ethyl, propyl, 2-methylpropyl, butyl, isobutyl, 2,2-dimethylpropyl, 2,2-dimethyl-butyl, n-hexyl, n-pentyl, and 3-ethylpentyl.

In some embodiments, $R_a$ is $C_1$-$C_4$ alkyl optionally substituted with hydroxy or $C_1$-$C_4$ alkoxy, wherein the alkoxy is optionally further substituted with —$NH_2$, —$NH(C_1$-$C_4$ alkyl), and —$N(C_1$-$C_4$ alkyl$)_2$.

In some embodiments, $R_a$ is $C_2$-$C_4$ alkenyl or $C_2$-$C_4$ alkynyl optionally substituted with hydroxy or amino.

In some embodiments, $R_a$ is $C_1$-$C_4$ alkyl substituted with 5- to 6-membered heterocycloalkyl having 1 or 2 atoms selected from N, S, and O, wherein the heterocycloalkyl moiety is optionally further substituted with $C_1$-$C_4$ alkyl, and preferably, the heterocycloalkyl is piperazinyl or morpholinyl.

In some embodiments, $R_a$ is $C_1$-$C_4$ alkyl substituted with —$NR^1R^2$, particularly -methylene-$NR^1R^2$, wherein $R^1$ and $R^2$ are each independently selected from:

- hydrogen;
- —$C_1$-$C_4$ alkyl;
- —$C_1$-$C_4$ alkyl substituted with a substituent selected from:
  - —OH, —$NH_2$, —$NH(C_1$-$C_4$ alkyl), —$N(C_1$-$C_4$ alkyl$)_2$, -phenyl, -phenylene-$NH_2$, -phenylene-$C_1$-$C_4$ alkoxy, -diphenyl, —$C_3$-$C_{10}$ cycloalkyl, —$C_3$-$C_{10}$ cycloalkylene-$C_1$-$C_4$ alkyl, and —$C_3$-$C_{10}$ heterocycloalkyl, wherein the heterocycloalkyl has 1 or 2 heteroatoms selected from N, S, and O, and preferably, the heterocycloalkyl is piperidinyl;
- phenyl; halogenated phenyl;
- $C_3$-$C_{10}$ cycloalkyl;
- —C(=O)—$C_1$-$C_4$ alkyl-OH; and —C(=O)—$C_1$-$C_4$ alkyl-$NH_2$.

In some embodiments, $R_a$ is $C_1$-$C_4$ alkyl substituted with —$NR^1R^2$, particularly -methylene-$NR^1R^2$, wherein $R^1$ and $R^2$, in combination with the nitrogen atom to which they are connected, form a 5-, 6-, or 7-membered heterocycloalkyl ring. In some aspects, $R^1$ and $R^2$, in combination with the nitrogen atom to which they are connected, form a 6-membered ring. In some aspects, the 6-membered ring is morpholinyl or piperazinyl.

In some preferred embodiments, $R_a$ is selected from: —$C_1$-$C_4$ alkylene-OH, —$C_1$-$C_4$ alkylene-O—$C_1$-$C_4$ alkylene-$NH_2$, —$C_1$-$C_4$ alkylene-$NH_2$, —$C_1$-$C_4$ alkylene-$NH(C_1$-$C_4$ hydroxyalkyl), —$C_1$-$C_4$ alkylene-$N(C_1$-$C_4$ hydroxyalkyl$)_2$, —$C_1$-$C_4$ alkylene-$N(C_1$-$C_4$ aminoalkyl)($C_1$-$C_4$ hydroxyalkyl), —$C_1$-$C_4$ alkylene-$NH(C_1$-$C_4$ aminoalkyl), —$C_1$-$C_4$ alkylene-NH—C(=O)—$C_1$-$C_4$ alkylene-OH; —$C_1$-$C_4$ alkylene-NH—C(=O)—$C_1$-$C_4$ alkylene-$NH_2$, —$C_1$-$C_4$ alkylene-$N(C_1$-$C_4$ alkyl)(C(=O)—$C_1$-$C_4$ alkylene-OH); and —$C_1$-$C_4$ alkylene-$N(C_1$-$C_4$ alkyl)(C(=O)—$C_1$-$C_4$ alkylene-$NH_2$).

In some more preferred embodiments, $R_a$ is —$C_1$-$C_4$ alkylene-NH—C(=O)—$C_1$-$C_4$ alkylene-OH; or —$C_1$-$C_4$ alkylene-NH—C(=O)—$C_1$-$C_4$ alkylene-$NH_2$.

In some more preferred embodiments, $R_a$ is —$C_2$-$C_4$ alkenylene-$NH_2$ or —$C_2$-$C_4$ alkenylene-OH, e.g., —CH=CH—$CH_2$—$NH_2$ or —CH=CH—$CH_2$—OH.

In some more preferred embodiments, $R_a$ is —$C_1$-$C_4$ alkylene-OH, —$C_1$-$C_4$ alkylene-O—$C_1$-$C_4$ alkylene-$NH_2$, or —$C_1$-$C_4$ alkylene-$NH_2$.

In some more preferred embodiments, $R_a$ is —$C_1$-$C_4$ alkylene-OH. In some aspects, $R_a$ is hydroxymethyl. In some aspects, $R_a$ is hydroxyethyl. In some aspects, $R_a$ is hydroxypropyl.

In other more preferred embodiments, $R_a$ is —$C_1$-$C_4$ alkylene-$NH_2$. In some aspects, $R_a$ is aminomethyl. In some aspects, $R_a$ is aminoethyl. In some aspects, $R_a$ is aminopropyl.

Preferably, the drug D is linked to the linker L via a free hydroxy or amino group thereon for conjugation to the antibody. More preferably, the drug D of formula D or formula $D_a$ or $D_b$ is linked to the linker L via a hydroxy or amino group on $R_a$ for conjugation to the antibody.

Preferably, after being linked to the linker, $R_a$ has a structure selected from:

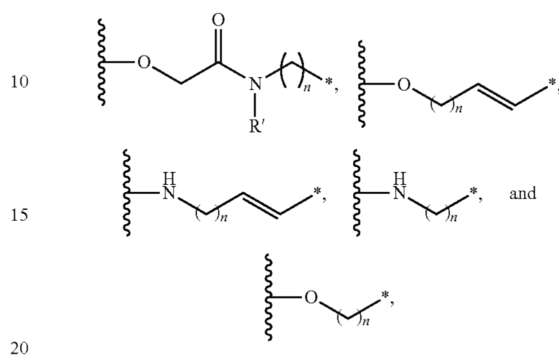

wherein n is an integer of 1-4, preferably n=2 or 3; R' is H or $C_1$-$C_4$ alkyl, preferably H; the left wavy line indicates the position of linkage to the linker L, and the right asterisk indicates the position of linkage to the camptothecin nucleus;

more preferably after being linked to the linker, $R_a$ has a structure selected from:

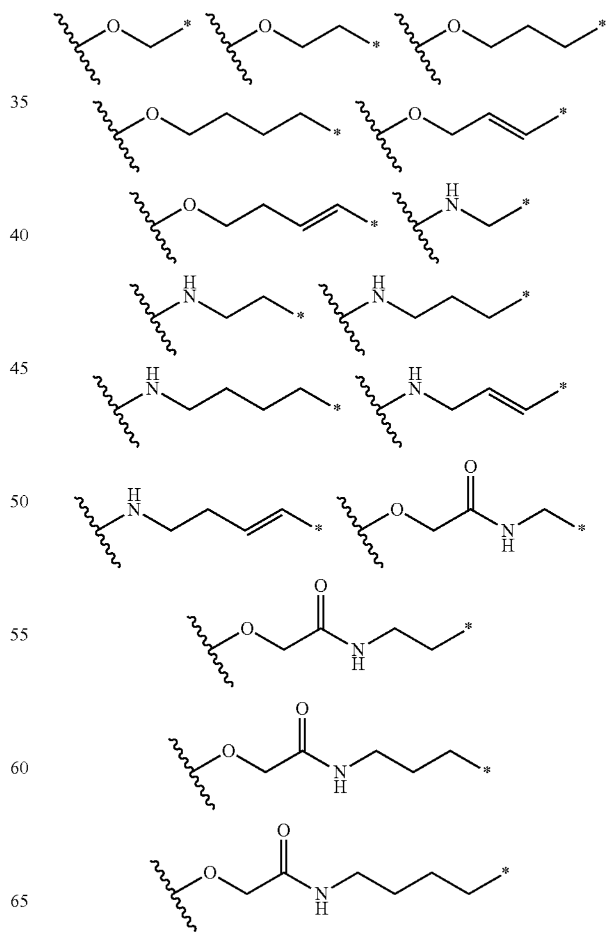

-continued

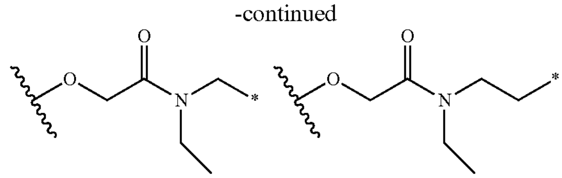

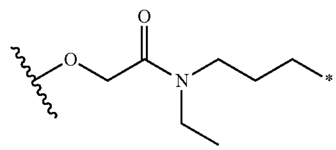

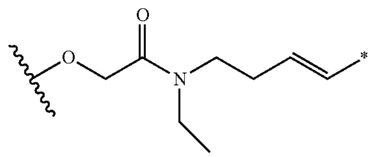

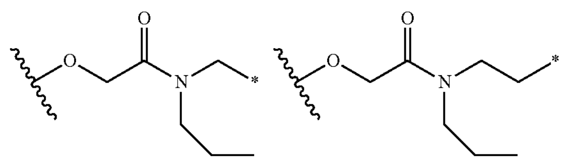

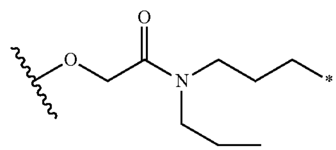

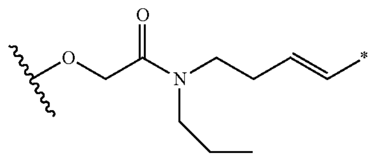

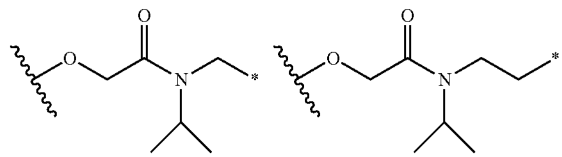

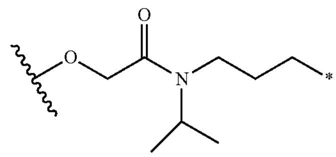

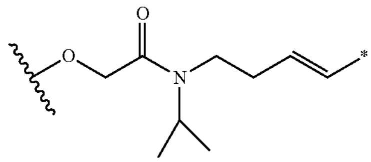

and most preferably, after being linked to the linker, $R_a$ has a structure selected from:

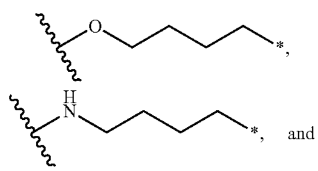

and

-continued

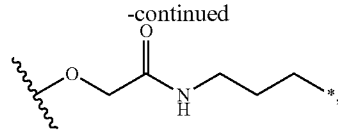

wherein the left wavy line indicates the position of linkage to the linker L, and the right asterisk indicates the position of linkage to the camptothecin nucleus.

In some preferred embodiments, the L-D unit in formula (I) of the present invention comprises the following structure:

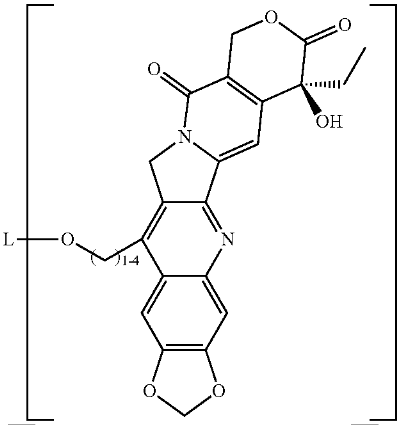

,

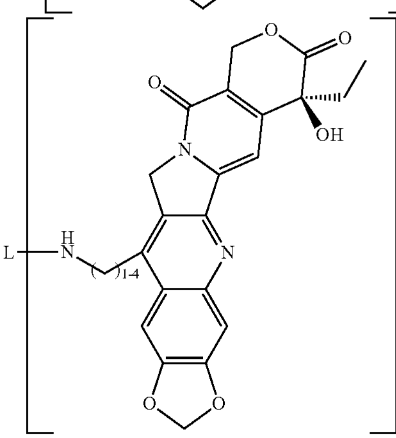

, or

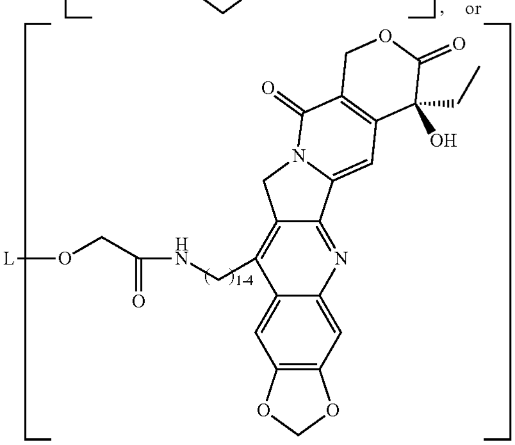

, and more preferably, the L-D unit in formula (I) comprises the following structure:

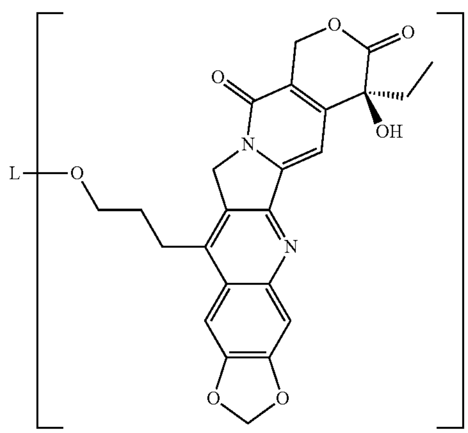

Linker L Unit

A linker L applicable to the present invention may be any linker capable of achieving conjugation of the antibody of the present invention to a drug. Suitably, the addition of the linker should ensure sufficient stability of the ADCs of the present invention in the circulatory system, while providing a rapid and effective release of active forms of the toxic drug at target sites (e.g., tumor cells or tumor environment).

In some embodiments, the linker in formula (I) of the present invention is a non-degradable linker. Examples of non-degradable linkers include, but are not limited to, N-succinimidyl-4-(N-maleimidomethyl)cyclohexane-1-carboxylate (SMCC). Typically, ADCs comprising such linkers must be internalized by the cells, and antibody moieties of the ADCs are degraded by intracellular lysosomal proteases, releasing active molecules of the drug.

In still other embodiments, the linker in formula (I) of the present invention is a degradable linker. Drug release from ADCs comprising such linkers is triggered by the property of cleavage sites in the linkers. Thus, the cleavage sites of such linkers can be designed based on the characteristics of the target treatment sites (e.g., tumor cell lysosomes and/or tumor environment). In most cases, the degradable linker may consist of a conjugation moiety, a degradable moiety, and optionally a spacer group moiety. The conjugation moiety is responsible for linking of the antibody to the linker-drug, and may be selected based on the desired antibody conjugation chemistry to be employed. Under an enzyme-based release mechanism, the degradable moiety will comprise peptides or peptide analogs that can be recognized by enzymes, e.g., oligopeptides or oligopeptide analogs, such as Val-Ala, Val-Cit, Phe-Lys, Gly-Phe-Leu-Gly (SEQ ID NO: 54), Ala-Leu-Ala-Leu (SEQ ID NO: 55), Gly-Gly-Phe-Gly (SEQ ID NO: 56), cyclobutyl-Ala, and cyclobutyl-Cit, which can be degraded by proteinases. In some cases, the properties of the ADC, e.g., stability of the ADC in blood circulation and/or efficacy of the ADC at a target site, may be improved by introducing modifications at peptide residue positions adjacent to the enzyme cleavage site in the linker. In some cases, if desired, a spacer group may also be introduced between the degradable moiety of the linker and the drug D so as to facilitate the release (particularly traceless release) of the active molecules of the drug from the rest of the conjugate, for example, a para-aminobenzyl carbamate (PABA) or aminomethyl (—$NHCH_2$—) spacer group which can be spontaneously eliminated in acidic media may be introduced. In addition, when the drug is highly hydrophobic, in some cases, it may be contemplated (but not necessary) to add, for example, a PEG unit to improve the properties of the ADC, for example, to reduce precipitation and aggregation. Linkers applicable to the present invention include, but are not limited to, those disclosed in WO2022/170971 (which is hereby incorporated by reference).

In some embodiments, the linker L in formula (I) of the present invention has a structure of formula (II) below:

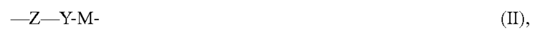

—Z—Y-M- (II), wherein

Z is a linking group linked to Ab,

Y is a peptide of 2-5 amino acids, preferably dipeptide, tripeptide or tetrapeptide, and M is absent or is a spacer group for linking to the drug D.

Z Linking Group

Typically, a sulfonyl group of cysteine of an antibody is present in the form of a disulfide bond. The disulfide bond of the antibody is opened, providing a free sulfhydryl group as a conjugation site. One approach to form an ADC by conjugation to the sulfhydryl group of the antibody is to subject the free sulfhydryl group on the antibody to a Michael addition reaction with a heterocyclic (e.g., maleimide) linker. Another approach is to subject a linker comprising a leaving group-substituted heteroaromatic ring to a nucleophilic substitution reaction with the free sulfhydryl group in the antibody molecule to obtain an antibody-drug conjugate. Both approaches are applicable to the ADCs of the present invention. Thus, the linker according to the present invention may in some aspects comprise a heterocyclic (e.g., maleimide) or heteroaromatic (e.g., pyrimidine) Z linking group, and in some cases, preferably comprise a heteroaromatic (e.g., pyrimidine) linking group, so as to provide a conjugate with greater stability in blood circulation.

In some embodiments, Z in formula (II) has the following structure:

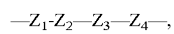

—$Z_1$-$Z_2$—$Z_3$—$Z_4$—, wherein $Z_1$ is a sulfur atom in Ab;

$Z_2$ is 5- to 10-membered heterocyclyl, preferably containing 1 or 2 heteroatoms selected from N, S, and O;

$Z_3$ is selected from a bond, —C(═O)—, —$C_1$-$C_{10}$ alkylene-C(═O)—, —$C_3$-$C_{10}$ alkynylene-C(═O)—, —$C_3$-$C_{10}$ alkenylene-C(═O)—, —$C_1$-$C_{10}$ heteroalkylene-C(═O)—, —$C_3$-$C_8$ cycloalkylene-C(═O)—, —O—$C_1$-$C_8$ alkylene-C(═O)—, -arylene-C(═O)—, —$C_1$-$C_{10}$ alkylene-arylene-C(═O)—, -arylene-$C_1$-$C_{10}$ alkylene-C(═O)—, —$C_1$-$C_{10}$ alkylene-$C_3$-$C_8$ cycloalkylene-C(═O)—, —$C_3$-$C_8$ cycloalkylene-$C_1$-$C_{10}$-alkylene-C(═O)—, —$C_3$-$C_8$-heterocyclylene-C(═O)—, —$C_1$-$C_{10}$ alkylene-$C_3$-$C_8$-heterocyclylene-C(═O)—, and —$C_3$-$C_8$ heterocyclylene-$C_1$-$C_{10}$ alkylene-C(═O)—; and $Z_4$ is a bond or a PEG unit represented by the following formula:

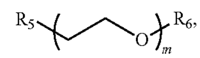

wherein $R_5$ is selected from $C_{1-4}$ alkylene, —NH—, and —NH—$C_{1-4}$ alkylene-heteroaryl-, wherein the heteroaryl is a 5- or 6-membered nitrogen-containing heteroaryl, preferably triazolyl; and $R_6$ is —C(═O)—, —$C_{1-4}$ alkylene, —$C_{1-4}$ alkylene-C(═O)—, —NH—C(═O)—

$(CH_2OCH_2)$—C(═O)—, or —$C_{1-4}$ alkylene-NH—C(═O)—$(CH_2OCH_2)$—C(═O)—, wherein m is an integer of 2-12, e.g., m=2, 4, 6, or 8.

In one embodiment, $Z_2$ is 5- to 10-membered heteroaryl. In one embodiment, $Z_2$ is selected from pyrimidine, thiazole, benzothiazole, oxazole, quinazoline, and pyrrolo[2,3d]pyrimidine optionally substituted with one or more substituents independently selected from hydrogen, halogen, nitro, $C_{1-6}$ alkyl, and $C_{1-6}$ haloalkyl. In some embodiments, $Z_2$ is a heteroaryl group selected from:

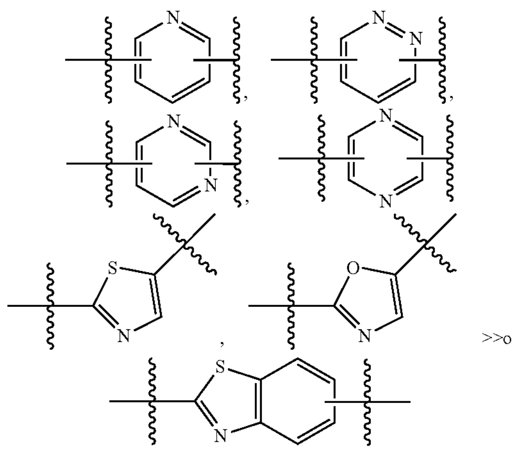

wherein $Z_2$ is linked to $Z_1$ via a carbon atom adjacent to the heteroatom. In a preferred embodiment, $Z_2$ is pyrimidinylene, preferably

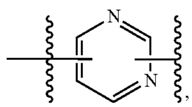

and more preferably

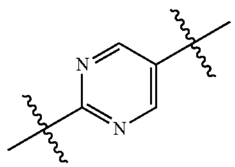

wherein the left wavy line indicates the position of linkage to $Z_1$, and the right wavy line indicates the position of linkage to $Z_3$.

In some embodiments, $Z_2$ is maleimido,

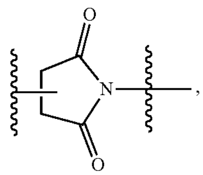

wherein the left wavy line indicates the position of linkage to $Z_1$, and the right wavy line indicates the position of linkage to $Z_3$.

In some embodiments, $Z_3$ is —$C_3$-$C_8$ heterocyclylene-C(═O)—, —$C_1$-$C_{10}$ alkylene-$C_3$-$C_8$ heterocyclylene-C(═O)—, and —$C_3$-$C_8$ heterocyclylene-$C_1$-$C_{10}$ alkylene-C(═O)—, wherein preferably, the heterocycle in the heterocyclylene is a heteroaromatic ring, such as triazole, pyrazole, thiazole, oxazole, isoxazole, or pyridazine.

In some embodiments, $Z_3$ is —$C_3$-$C_8$-heteroarylene-$C_1$-$C_{10}$ alkylene-C(═O)—, particularly,

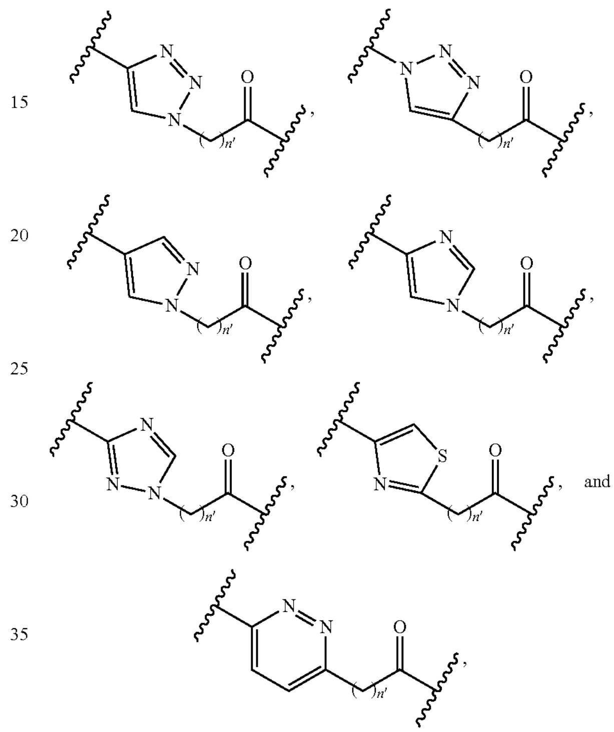

wherein n' is 1-6, preferably, $Z_3$ is

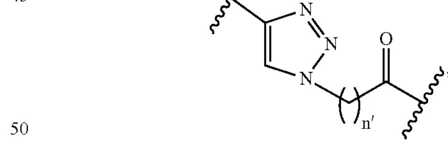

and more preferably

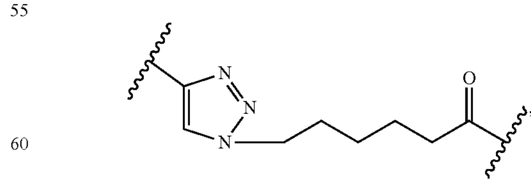

wherein the left wavy line indicates the position of linkage to $Z_2$, and the right wavy line indicates the position of linkage to $Z_4$, and preferably, $Z_2$ is pyrimidinylene.

In some embodiments, $Z_3$ is arylene- or heteroarylene-C(=O)—, particularly,

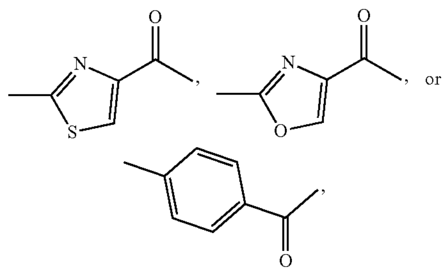

wherein $Z_3$ is linked to $Z_4$ via —C—(=O)—, and preferably, $Z_2$ is pyrimidinylene.

In other embodiments, $Z_3$ is —(C≡C)—$C_{1-5}$ alkylene-C(=O)—, —(CH=CH)—$C_{1-5}$ alkylene-C(=O)—, —$C_{1-6}$ alkylene-C(=O)—, or —$C_{3-8}$ cycloalkylene-C(=O)—, wherein $Z_3$ is linked to $Z_4$ via —C—(=O)—.

In some preferred embodiments, $Z_2$ is pyrimidinylene, and $Z_3$ is —C(=O)—.

In some preferred embodiments, $Z_2$ is pyrimidinylene, and $Z_3$ is —(C≡C)—$C_{1-5}$ alkylene-C(=O)— or —(CH=CH)—$C_{1-5}$ alkylene-C(=O)—, particularly —(C≡C)—$C_{1-5}$ alkylene-C(=O)—.

In some preferred embodiments, $Z_2$ is maleimido, and $Z_3$ is —$C_{1-6}$ alkylene-C(=O)— or —$C_{3-8}$ cycloalkylene-C(=O)—.

In some embodiments, $Z_4$ is a bond, and $Z_3$ is directly linked to Y in formula (II).

In some embodiments, $Z_4$ is a unit comprising 2-12 PEGs. In some embodiments, $Z_4$ is

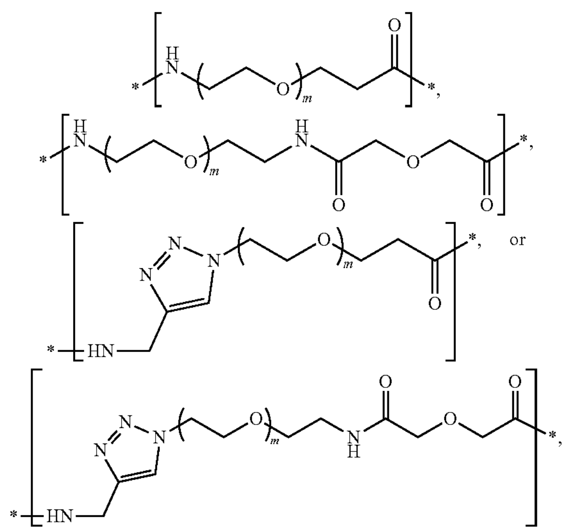

wherein m=1-8, e.g., 2, 3, 4, 5, 6, 7, or 8.

In some embodiments, $Z_4$ is selected from:

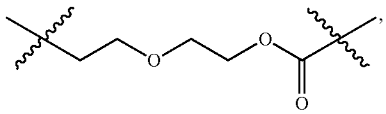

-continued

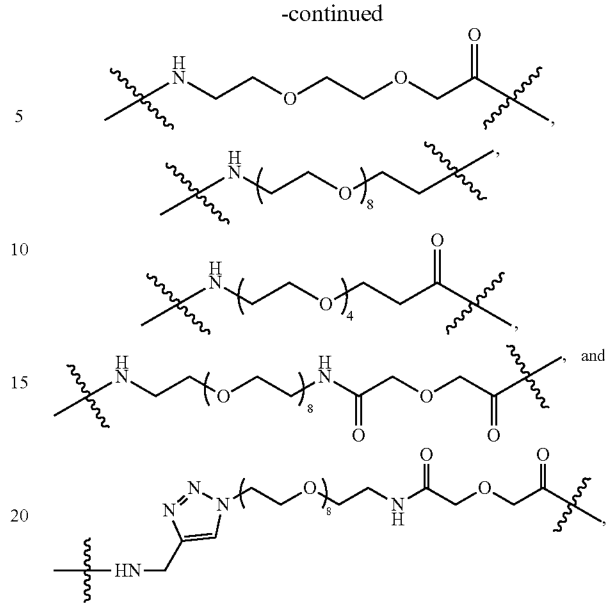

wherein the left wavy line indicates the position of linkage to $Z_3$, and the right wavy line indicates the position of linkage to Y in formula II.

In some embodiments, Z in formula (I) of the present invention has the following structure:

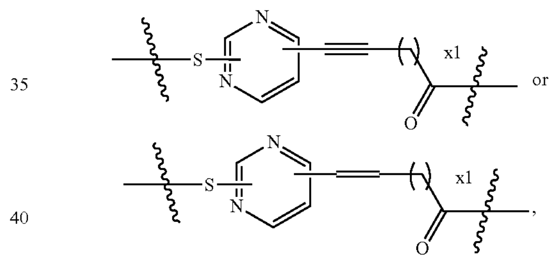

wherein $x_1$=1-8, e.g., $x_1$=3.

In some embodiments Z in formula (I) of the present invention has the following structure:

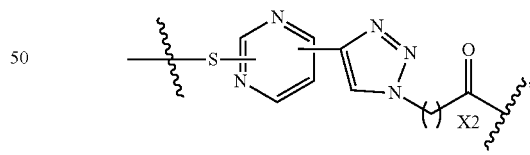

wherein $x_2$=1-6.

In some preferred embodiments, Z in formula (I) of the present invention has the following structure:

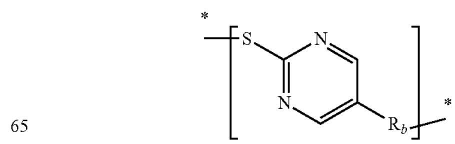

wherein S is a sulfur atom in Ab, and $R_b$ is unsubstituted or substituted —$C_{3-10}$ alkynyl-C(=O)— or —$C_{3-10}$ alkenyl-C(=O)—, preferably, $R_b$ is:

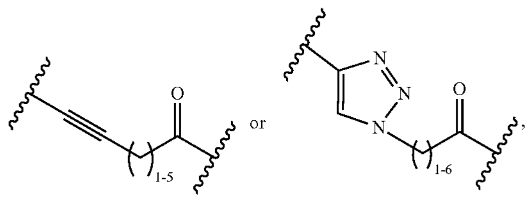

wherein the left wavy line indicates the position of linkage to pyrimidinyl, and the right wavy line indicates the position of linkage to Y;

more preferably, Z has the following structure:

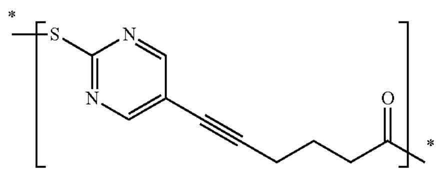

In some embodiments, Z in formula (I) of the present invention has the following structure:

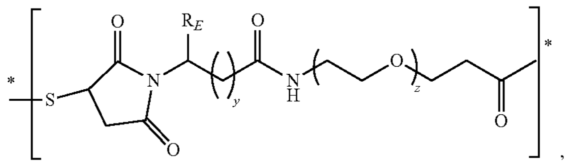

wherein $R_E$ is hydrogen, $C_{1-6}$ alkyl, $C_{1-6}$ aminoalkyl, $C_{1-6}$ haloalkyl, or $C_{1-6}$ hydroxyalkyl, and y=0-4, e.g., 0, 2, or 5, wherein the alkyl, amino and hydroxy moieties are optionally substituted; and in some embodiments, $R_E$ is optionally substituted aminoalkyl, e.g., substituted with —$C_{1-4}$ alkylene-$NH_2$, —$C_{1-4}$ alkylene $NHR_F$, and —$C_{1-4}$ alkylene $N(R_F)_2$, wherein each $R_F$ is independently selected from $C_{1-6}$ alkyl and $C_{1-6}$ haloalkyl; or the two $R_F$ groups, in combination with the nitrogen to which they are attached, form an azetidinyl, pyrrolidinyl or piperidinyl group.

In some embodiments, Z in formula (I) of the present invention has the following structure:

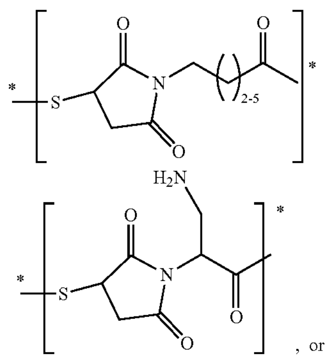

-continued

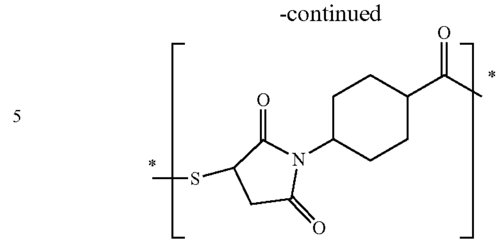

Peptide-Containing Y Unit

In some aspects, for the purpose of limiting or minimizing the non-targeted toxicity of ADCs while ensuring the release of toxin molecules at the target tumor site, it is advantageous to design antibody-drug conjugates so that they can be degraded by proteinases in tumor cells or in tumor environment (particularly enzymes with significantly higher activity in the tumor cells and/or in the tumor environment relative to blood) while targeting the tumor cells with high selectivity. For this purpose, oligopeptides or oligopeptide analogs that can be recognized and cleaved by such proteinases can be contained in linkers of such ADCs.

Thus, in one embodiment, Y unit that is part of a linker of the present invention is a peptide-containing degradable moiety such as a degradable peptide linker containing two or more (e.g., 2-12, such as 2, 3, 4, 5, or 6) contiguous or non-contiguous amino acids. Each amino acid in the peptide-containing unit may be independently selected from natural amino acids and non-natural amino acids, for example, selected from: alanine, arginine, aspartic acid, asparagine, histidine, glycine, glutamic acid, glutamine, phenylalanine, lysine, substituted lysine, leucine, serine, tyrosine, threonine, isoleucine, proline, tryptophan, valine, cysteine, methionine, selenocysteine, ornithine, 0-alanine, citrulline and derivatives thereof. In some embodiments, each amino acid is independently selected from alanine, arginine, aspartic acid, asparagine, histidine, glycine, glutamic acid, glutamine, phenylalanine, lysine, leucine, serine, tyrosine, threonine, isoleucine, proline, tryptophan, valine, cysteine, methionine and derivatives thereof. In some embodiments, each amino acid is independently selected from alanine, arginine, aspartic acid, asparagine, histidine, glycine, glutamic acid, glutamine, phenylalanine, lysine, leucine, serine, tyrosine, threonine, isoleucine, proline, tryptophan, valine, N-methylglycine, β-alanine and derivatives thereof. In some aspects, upon the internalization of the ADCs into the tumor cells, amide bonds in the Y unit will be recognized and degraded by enzymes in the lysosomes of the tumor cells to release the drug moiety D. In other aspects, the amide bonds in the Y unit can be recognized and degraded by enzymes in the tumor environment to release the drug moiety D. Linkers with such peptide-containing Y units will facilitate the release of the toxin molecules in the tumor cells and in the tumor environment by designing antibody-drug conjugates with a tumor-biased distribution.

In some embodiments, Y is a unit including the following selected from: Val-Cit, Phe-Lys, Val-Ala, Val-Lys-Gly, Ala-Ala-Ala, Val-Ala, Gly-Phe-Leu-Gly (SEQ ID NO: 54), Ala-Leu-Ala-Leu (SEQ ID NO: 55), Gly-Gly-Phe-Gly (SEQ ID NO: 56), cyclobutyl-Ala, and cyclobutyl-Cit. In some embodiments, Y is a unit comprising the following selected from: Val, Cit, Phe, Lys, D-Val, Leu, Gly, Ala, Asn, Cit-Val, Val-Ala, Lys-Val, Val-Lys(Ac), Phe-Lys, Phe-Lys(Ac), D-Val-Leu-Lys, Gly-Gly-Arg, and Ala-Ala-Asn.

In some preferred embodiments, Y is a dipeptide, tripeptide, tetrapeptide, or pentapeptide comprising a substituted lysine. In one embodiment, the substituted lysine is:

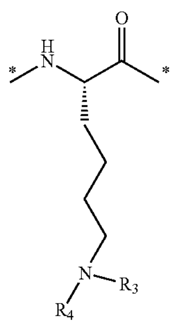

wherein $R_3$ and $R_4$ are each independently selected from: H, $C_{1-6}$ alkyl, —CO—$NH_2$, —CONH($C_{1-6}$ alkyl), and —CONH($C_{1-6}$ alkyl)$_2$, wherein the alkyl is optionally substituted with a group selected from: halogen, $C_{1-6}$ alkoxy, $C_{1-6}$ haloalkyl, $C_{3-6}$ cycloalkyl, 6- to 10-membered aryl, and 5- to 14-membered heteroaryl.

In some preferred embodiments, Y is a peptide having an amino acid sequence of the following formula from the N-terminus to the C-terminus:

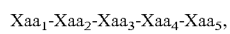

$Xaa_1$-$Xaa_2$-$Xaa_3$-$Xaa_4$-$Xaa_5$, wherein $Xaa_1$ is absent or is an amino acid selected from valine, glycine, alanine, and glutamic acid;

$Xaa_2$ is an amino acid selected from phenylalanine, leucine, alanine, and valine, preferably valine;

$Xaa_3$ is unsubstituted or substituted lysine;

$Xaa_4$ is an amino acid selected from leucine, glycine, and alanine;

$Xaa_5$ is absent or is an amino acid selected from glycine and alanine; and wherein the N-terminus of the amino acid sequence is linked to Z unit of the linker and the C-terminus is linked to M unit or directly to the drug D, preferably, $Xaa_3$ is lysine in which an ε-amino group is monosubstituted or disubstituted with $C_1$-$C_3$ alkyl, and more preferably, Y is a peptide selected from: Phe-Lys-Gly, Leu-lys-Gly, Gly-Val-Lys-Gly (SEQ ID NO: 57), Val-Lys-Gly-Gly (SEQ ID NO: 58), Val-Lys-Gly, Val-Lys-Ala, and Val-Lys-Leu, wherein the Lys residue is unsubstituted lysine or lysine monosubstituted or disubstituted with $C_1$-$C_3$ alkyl.

M Spacer Group

In some embodiments, the ADCs of the present invention have a spacer group (M) between the releasable peptide-containing unit (Y) and the drug (D). The spacer group may be a functional group that facilitates the linkage of the peptide-containing unit (Y) to the drug D, or can provide an additional structural component to further facilitate the release of the drug D from the rest of the conjugate (e.g., a self-immolative group such asp-aminobenzyl (PAB) component).

In some embodiments, the M spacer group linking the Y unit to the drug D unit may be selected from:

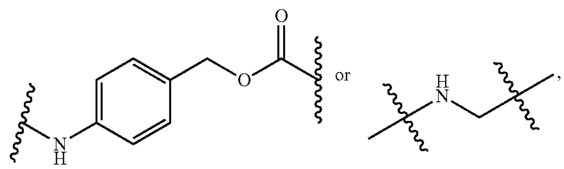

or , preferably

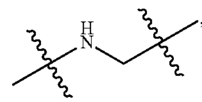 [SMILES: *CN*]

, wherein the left wavy line indicates the linkage to Y and the right wavy line indicates the linkage to the drug D unit.

In other embodiments, M is a covalent bond, and Y is directly linked to the drug D in formula I, such as through an amide bond.

In a preferred embodiment, a Y-M unit in the linker L comprises the following structure:

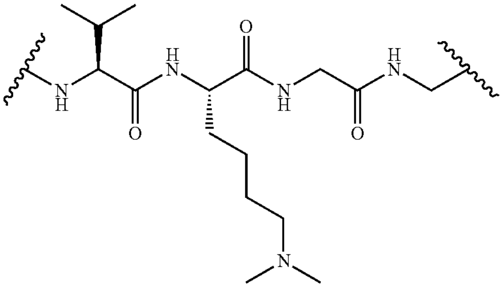

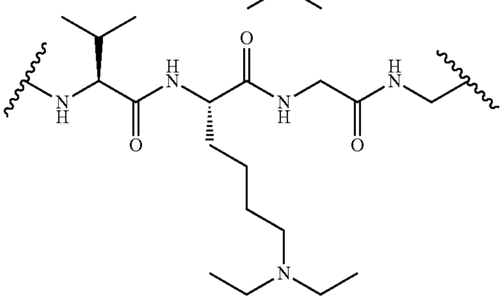

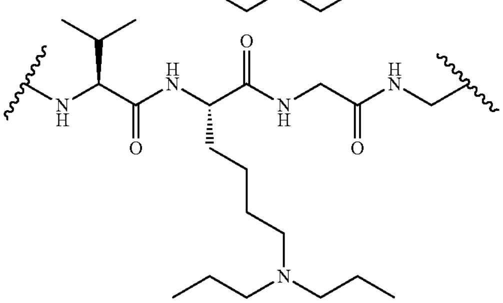

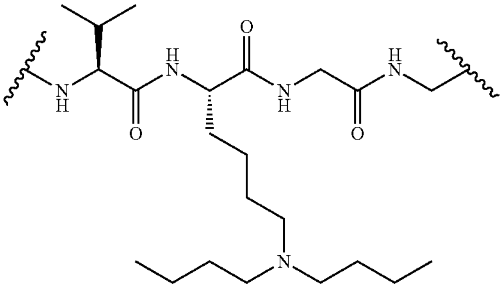

, and preferably, the Y-M unit is linked to the following Z unit:

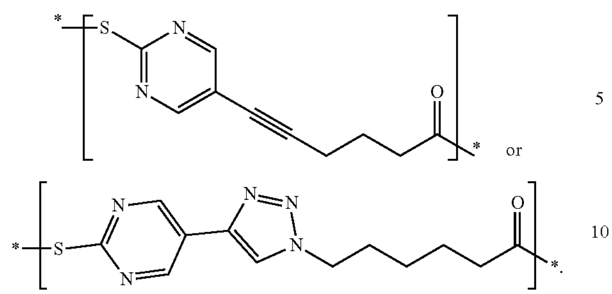

or

Exemplary Linker L

In some preferred embodiments, L in formula (I) of the present invention is a linker comprising the following structure:

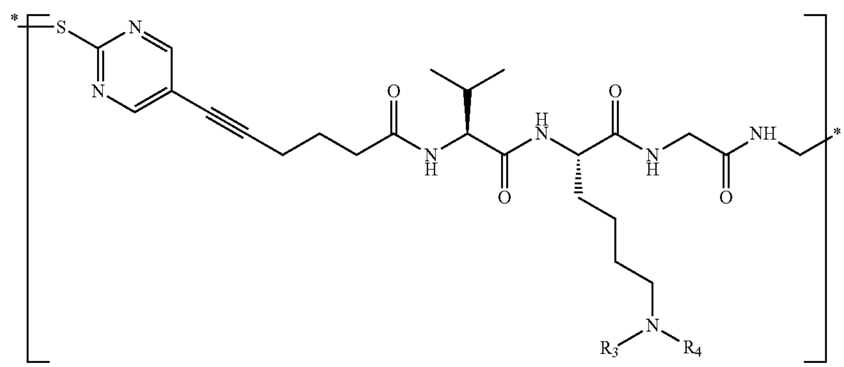

wherein $R_3$ and $R_4$ are each independently selected from methyl, ethyl, and propyl. In some more preferred embodiments, $R_3$ and $R_4$ are both methyl; or $R_3$ and $R_4$ are both ethyl; or $R_3$ and $R_4$ are both propyl.

In some embodiments, the L-D unit in formula I of the present invention is linked to the antibody by forming a thioether bond with a sulfhydryl group of a free cysteine of the light chain and/or heavy chain of Ab.

Exemplary ADC

In some embodiments, the present invention provides an ADC having the following structure, or a pharmaceutically acceptable salt or solvate thereof:

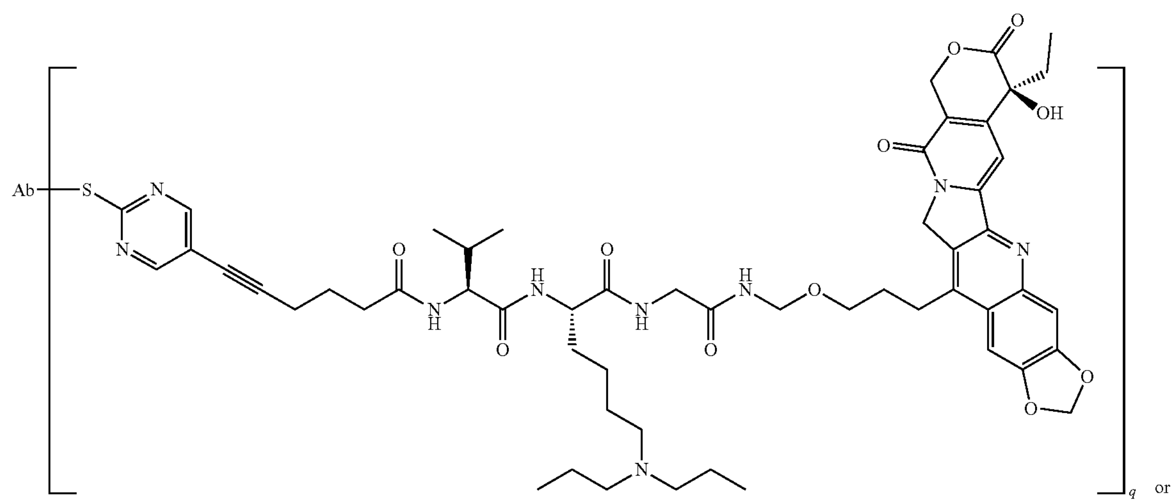

or

-continued

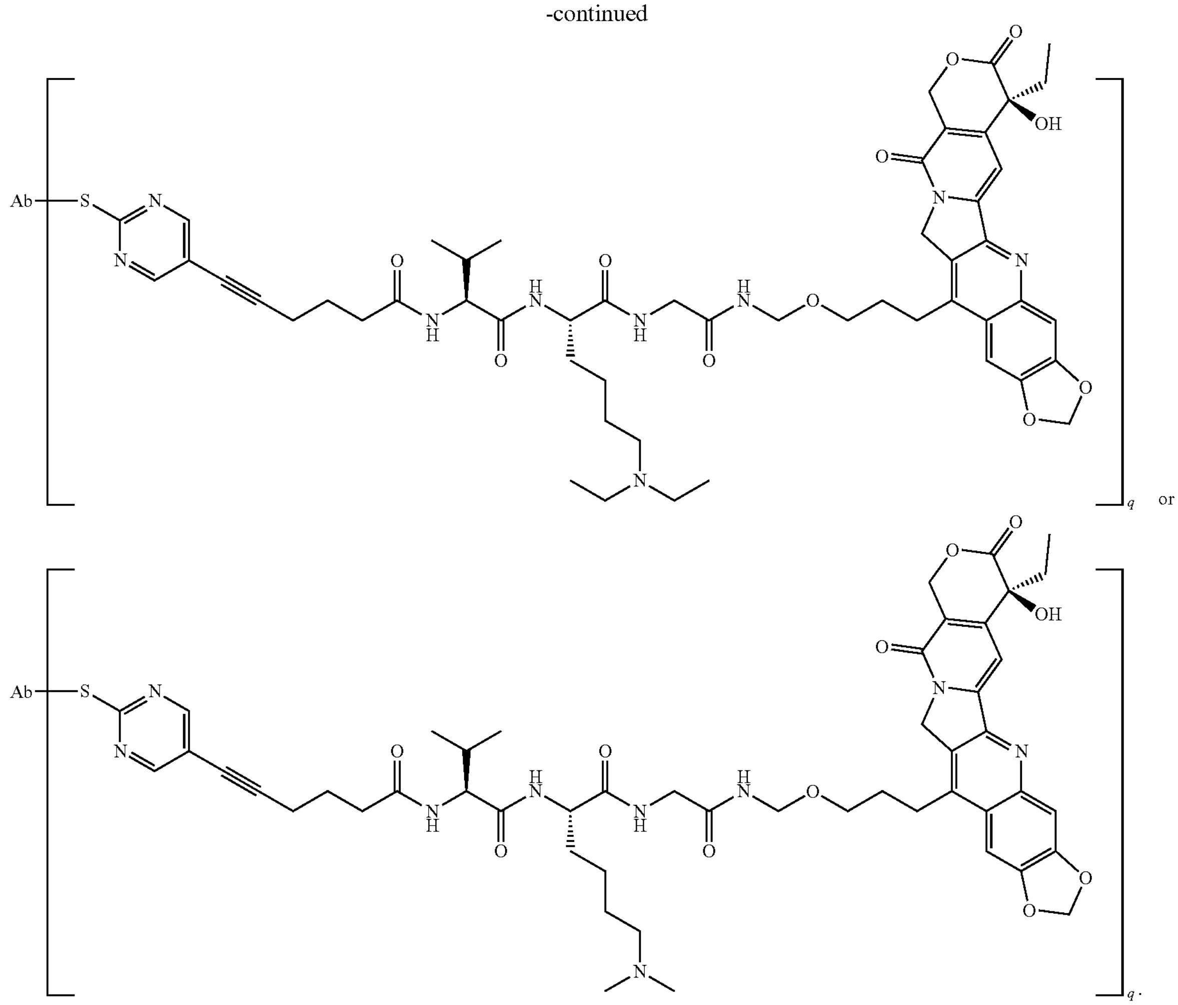

or wherein q represents an average DAR value of 1-20, such as an average DAR value of about 2, 4, 6, or 8.

In some embodiments, the ADC according to the present invention has at least one or more of the following advantages:

- significantly facilitating the distribution and enrichment of the ADC into the tumor environment relative to the distribution of the ADC in the blood circulation;
- effectively limiting the premature release of the payload in the plasma, and having a high blood circulation stability;
- providing the effective release of active forms of the toxic drug in the tumor environment;
- conferring an efficient in-vivo tumor-killing effect in an animal; and
- good tolerance in the animal.

In still other embodiments, the ADC according to the present invention can further have at least one or more of the following advantages:

- the addition of toxin-linkers not inducing the aggregation, and being capable of achieving a high drug loading with a DAR value up to 8; and
- acceptable PK properties.

II. Preparation of Antibody-Drug Conjugates

The generation of antibody-drug conjugates can be accomplished by any technique known to those skilled in the art. In some aspects, drug-linkers are conjugated to antibodies by reacting with amino acid residues of the antibodies. In some embodiments, drug D is conjugated to a cysteine residue of an antibody using a heteroaryl linker L with a leaving group to prepare the conjugate of formula I of the present invention. In some embodiments, an interchain disulfide bond of the antibody can be disrupted to expose the free sulfhydryl group for the conjugation to a heteroaryl linker-drug by controlling the conditions under which the antibody is treated with a reducing agent, such as tris(2-carboxyethyl)phosphine (TCEP). For IgG1 antibodies, up to four linking disulfide bonds can be reduced, thereby generating up to 8 reactive sulfhydryl groups for conjugation. Conjugates prepared by this method may comprise zero, one, two, three, four, five, six, seven, or eight drugs in each antibody molecule.

When the prepared conjugates are conjugate compositions having different drug conjugation sites and/or numbers, the drug loading of the conjugates is represented by the average DAR, which is the average number of drug molecules per antibody. The average number of drugs per antibody for the produced antibody-drug conjugate compositions can be characterized by conventional means, such as mass spectrometry, ELISA assay, and HPLC. In other embodiments, the quantitative distribution of the antibody-drug conjugates, denoted by q, can also be determined. The separation, purification and characterization of homogeneous antibody-drug conjugates, where q is a certain value, from antibody-drug conjugates with other drug loadings can be achieved by means such as reverse-phase HPLC or electrophoresis.

Thus, in one aspect of the present invention, q represents the number of drug-linker (L-D) moieties conjugated to one single antibody (Ab), and is preferably an integer from 1 to 16, 1 to 12, 1 to 10, or 1 to 8. In this case, individual ADCs can also be referred to as ADC compounds. In any embodiments of the present invention, there may be 1, 2, 3, 4, 5, 6, 7, 8, 9, 10, 11, 12, 13, 14, 15, or 16 drug-linker moieties conjugated to one single antibody on the ADC compounds according to the present invention.

In another aspect of the present invention, q represents the average DAR of the prepared conjugate compositions. In this case, q may be an integer or decimal ranging from 1 to about 16, from 1 to about 12, from 1 to about 10, or from 1 to about 8, from 2 to about 16, from 2 to about 12, from 2 to about 10, or from 2 to about 8. In some aspects, q represents an average DAR value of about 6. In some aspects, q represents an average DAR value of about 8.

III. Pharmaceutical Composition

In some embodiments, the present invention provides a composition comprising any of the ADCs or the pharmaceutically acceptable salts or solvates thereof described herein, wherein preferably, the composition is a pharmaceutical composition or a pharmaceutical formulation. In one embodiment, the composition further comprises a pharmaceutical auxiliary material. In one embodiment, the composition, e.g., the pharmaceutical composition, comprises a combination of the ADC or the pharmaceutically acceptable salt or solvate thereof of the present invention with one or more additional therapeutic agents.

The present invention further comprises a composition (including a pharmaceutical composition) comprising the ADC or the pharmaceutically acceptable salt or solvate thereof of the present invention. Such compositions can further comprise a suitable pharmaceutical auxiliary material, such as a pharmaceutical carrier and a pharmaceutical excipient known in the art, including buffers.

As used herein, the "pharmaceutical carrier" includes any and all solvents, dispersion media, isotonic agents and absorption delaying agents, and the like that are physiologically compatible.

For use and application of the pharmaceutical auxiliary materials, see Handbook of Pharmaceutical Excipients, 8th Ed., R. C. Rowe, P. J. Seskey and S. C. Owen, Pharmaceutical Press, London, Chicago.

The composition of the present invention may be in a variety of forms. Such forms include, for example, liquid, semi-solid and solid dosage forms, such as liquid solutions (e.g., injectable solutions and infusible solutions), pulvis or suspensions, liposomes, and suppositories. The preferred form depends on the intended mode of administration and therapeutic use.

The drug, preferably in the form of a lyophilized formulation or an aqueous solution, comprising the ADC described herein can be prepared by mixing the ADC or the pharmaceutically acceptable salt or solvate thereof of a desired purity of the present invention with one or more optional pharmaceutical auxiliary materials.

The pharmaceutical composition or formulation of the present invention can further comprise more than one active ingredient required by a specific indication treated, preferably those having complementarity activity without adversely affecting one another. For example, it may be desirable to also provide additional therapeutic agents, including chemotherapeutic agents, angiogenesis inhibitors, cytokines, cytotoxic agents, other antibodies, small molecule drugs, immunomodulators (e.g., immune checkpoint inhibitors or agonists), or the like. The active ingredients are suitably combined in an amount effective for an intended purpose.

A sustained release formulation can be prepared. Suitable examples of the sustained release formulation include a semi-permeable matrix of a solid hydrophobic polymer containing an antibody. The matrix is in the form of a shaped article, such as a film or a microcapsule.

IV. Pharmaceutical Combination and Kit

In some embodiments, the present invention further provides a pharmaceutical combination or pharmaceutical combination product, comprising the ADC or the pharmaceutically acceptable salt or solvate thereof of the present invention, and one or more additional therapeutic agents (e.g., therapeutic agents, including chemotherapeutic agents, angiogenesis inhibitors, cytokines, cytotoxic agents, other antibodies, small molecule drugs, immune modulators (e.g., immune checkpoint inhibitors or agonists), or the like).

Another object of the present invention is to provide a kit of parts comprising the pharmaceutical combination of the present invention; preferably, the kit is in the form of a pharmaceutical dose unit. Dose units may thus be provided according to the administration regimen or the interval between drug administrations.

In one embodiment, the kit of parts of the present invention comprises the following in the same package:

- a first container containing a pharmaceutical composition comprising the ADC or the pharmaceutically acceptable salt or solvate thereof of the present invention;
- a second container containing a pharmaceutical composition comprising an additional therapeutic agent.

V. Use and Method

In one aspect, the present invention provides a method for preventing or treating a tumor (e.g., cancer) in a subject, comprising administering to the subject an effective amount of the ADC or the pharmaceutically acceptable salt or solvate thereof, the pharmaceutical composition, the pharmaceutical combination, or the kit of the present invention.

CLDN18.2 is selectively expressed on the surface of cancer tissue cells from a variety of origins, thereby being a suitable target for the development of cancer immunotherapies. CLDN18.2 has been found to be highly selectively expressed in digestive system cancers such as pancreatic cancer, esophageal cancer, gastric cancer, and the like. Thus, in one aspect, the present invention provides use of the antibody of the present invention in the prevention and/or treatment of a CLAUDIN 18.2-positive tumor in a subject, comprising administering the antibody-drug conjugate of the present invention in a prophylactically and/or therapeutically effective amount. In some embodiments, the antibody-drug conjugate of the present invention may be administered as the sole active agent, or may be administered in combination with an additional therapy or therapeutic agent. The additional therapy and therapeutic agent include, for example, drugs that target antigens on the surface of tumor cells to destroy tumors by binding and/or blocking these molecules; and drugs that activate the immune system of the subject to spontaneously destroy the tumors.

In some embodiments, the tumor treated according to the present invention may be a cancer at an early, middle or advanced stage, or may be a metastatic cancer. In some embodiments, the tumor treated according to the present invention is a tumor that has previously undergone treatment but has developed immune escape.

In the method of the present invention, administration of the antibody-drug conjugate of the present invention may comprise: 1) a therapeutic measure that cures, slows, alleviates symptoms of the diagnosed pathological condition or disease, and/or stops progression of the diagnosed pathological condition or disease; or 2) a prophylactic or preventative measure that prevents and/or slows the progression of the pathological condition or disease. In some embodiments, in the method of the present invention, the individual will benefit from the therapeutic measure or the prophylactic measure and exhibit an alleviation or amelioration in the occurrence, recurrence or progression of the disease, disorder, condition, and/or symptom as compared to an individual not receiving the treatment. In some embodiments, the subject is receiving or has received an additional therapy, such as chemotherapy and/or radiotherapy, or other immunotherapies, prior to receiving a therapy according to the method of the present invention.

In a specific embodiment, the antibody-drug conjugate of the present invention is capable of killing CLDN18.2-positive tumor cells and/or inhibiting proliferation of CLDN18.2-positive tumor cells.

The antibody-drug conjugate of the present invention may be administered by any suitable route, including parenteral administration, intratumoral administration, and intranasal administration. Parenteral infusion includes intramuscular, intravenous, intra-arterial, intraperitoneal or subcutaneous administration. Administration may be performed by any suitable route, e.g., by injection, e.g., intravenous or subcutaneous injection, depending in part on whether the medication is for short-term or long-term. Various administration schedules are encompassed herein, including, but not limited to, single administration or multiple administrations at multiple time points, bolus injection, and pulse infusion.

In order to prevent or treat a disease, the appropriate dose of the antibody-drug conjugate of the present invention (when used alone or in combination with one or more additional therapeutic agents) will depend on the type of the disease to be treated, the particular type of the antibody-drug conjugate, the severity and progression of the disease, the purpose of the treatment, previous therapies, the patient's clinical history and response to the antibody-drug conjugate, and the discretion of an attending physician. The antibody-drug conjugate of the present invention may suitably be administered to a patient in a single treatment or over a series of treatments.

In some embodiments, the present invention further provides use of the antibody-drug conjugate of the present invention in the preparation of a medicament for use in the above therapeutic and prophylactic methods.

Antibody Moiety of the Present Invention

The present invention further provides a humanized anti-Claudin18.2 monoclonal antibody with various excellent properties, a nucleic acid encoding the antibody, a vector and host cell comprising the nucleic acid, as well as an immunoconjugate comprising the antibody, a multispecific antibody, a pharmaceutical composition, and use. The antibody of the present invention not only exhibits high binding affinity and high specificity for cells expressing human Claudin18.2 on the surface (particularly cells with low surface expression abundance), but also has advantageous properties such as ADCC and/or CDC activity, Claudin18.2 antigen-mediated endocytic activity, stability, and/or pharmacokinetic properties, thus being suitable for use in a cancer therapy, either alone or in combination with other anti-cancer drugs, and also being suitable as a molecular component for the formation of a novel anti-cancer molecule targeting cancer tissues, e.g., for conjugation with a cytotoxic drug to form an antibody-drug conjugate.

I. Antibody of the Present Invention

The present invention provides an antibody or an antigen-binding fragment thereof, particularly a humanized antibody or an antigen-binding fragment thereof, that specifically binds to Claudin18.2, preferably to a human Claudin18.2 protein (e.g., a human Claudin18.2 sequence of NM_001002026). In one embodiment, the anti-Claudin18.2 antibody or the antigen-binding fragment thereof according to the present invention comprises:

(i) HCDR1, 2 and 3 sequences of a heavy chain variable region set forth in SEQ ID NO: 1 or 3, and LCDR1, 2 and 3 sequences of a light chain variable region set forth in SEQ ID NO: 2; or (ii) HCDR1, 2 and 3 sequences of a heavy chain variable region set forth in SEQ ID NO: 21, and LCDR1, 2 and 3 sequences of a light chain variable region set forth in SEQ ID NO: 22; or (iii) HCDR1, 2 and 3 sequences of a heavy chain variable region set forth in SEQ ID NO: 23, and LCDR1, 2 and 3 sequences of a light chain variable region set forth in SEQ ID NO: 24; or (iv) HCDR1, 2 and 3 sequences of a heavy chain variable region set forth in SEQ ID NO: 38 or 40, and LCDR1, 2 and 3 sequences of a light chain variable region set forth in SEQ ID NO: 39; or (v) HCDR1, 2 and 3 sequences of a heavy chain variable region set forth in SEQ ID NO: 44, and LCDR1, 2 and 3 sequences of a light chain variable region set forth in SEQ ID NO: 45; or (vi) HCDR1, 2 and 3 sequences of a heavy chain variable region set forth in SEQ ID NO: 46, and LCDR1, 2 and 3 sequences of a light chain variable region set forth in SEQ ID NO: 47; or (vii) HCDR1, 2 and 3 sequences of a heavy chain variable region set forth in SEQ ID NO: 48, and LCDR1, 2 and 3 sequences of a light chain variable region set forth in SEQ ID NO: 49; or (viii) HCDR1, 2 and 3 sequences of a heavy chain variable region set forth in SEQ ID NO: 50, and LCDR1, 2 and 3 sequences of a light chain variable region set forth in SEQ ID NO: 51; or (ix) HCDR1, 2 and 3 sequences of a heavy chain variable region set forth in SEQ ID NO: 52, and LCDR1, 2 and 3 sequences of a light chain variable region set forth in SEQ ID NO: 53. Preferably, the CDRs are defined according to Kabat or IMGT, or a combination thereof.

In some embodiments, preferably, the present invention provides an antibody or an antigen-binding fragment thereof that binds to Claudin18.2, comprising 3 complementarity determining regions of a heavy chain variable region (HCDRs), and 3 complementarity determining regions of a light chain variable region (LCDRs), wherein (i) according to the Kabat scheme, the HCDR1 comprises or consists of an amino acid sequence of SEQ ID NO: 12, the HCDR2 comprises or consists of an amino acid sequence of SEQ ID NO: 13 or 25, the HCDR3 comprises or consists of an amino acid sequence of SEQ ID NO: 14, the LCDR1 comprises or consists of an amino acid sequence of SEQ ID NO: 15, the LCDR2 comprises or consists of an amino acid sequence of SEQ ID NO: 16, and the LCDR3 comprises or consists of an amino acid sequence of SEQ ID NO: 17; or (ii) according to the IMGT scheme, the HCDR1 comprises or consists of an amino acid sequence of SEQ ID NO: 6, the HCDR2 comprises or consists of an amino acid sequence of SEQ ID NO: 7, the HCDR3 comprises or consists of an amino acid sequence of SEQ ID NO: 8, the LCDR1 comprises or consists of an amino acid sequence of SEQ ID NO: 9, the LCDR2 comprises or consists of an amino acid sequence of EAS, and the LCDR3 comprises or consists of an amino acid sequence of SEQ ID NO: 11; or (iii) according to the Kabat scheme, the HCDR1 comprises or consists of an amino acid sequence of SEQ ID NO: 26, the HCDR2 comprises or consists of an amino acid sequence of SEQ ID NO: 27 or 37, the HCDR3 comprises or consists of an amino acid sequence of SEQ ID NO: 28, the LCDR1 comprises or consists of an amino acid sequence of SEQ ID NO: 32, the LCDR2 comprises or consists of an amino acid sequence of SEQ ID NO: 33, and the LCDR3 comprises or consists of an amino acid sequence of SEQ ID NO: 34; or (iv) according to the Kabat scheme, the HCDR1 comprises or consists of an amino acid sequence of SEQ ID NO: 29, the HCDR2 comprises or consists of an amino acid sequence of SEQ ID NO: 30, the HCDR3 comprises or consists of an amino acid sequence of SEQ ID NO: 31, the LCDR1 comprises or consists of an amino acid sequence of SEQ ID NO: 35, the LCDR2 comprises or consists of an amino acid sequence of WAS, and the LCDR3 comprises or consists of an amino acid sequence of SEQ ID NO: 34.

Antibodies comprising variants of one of the CDR sequence combinations in (i)-(iv) above are also contemplated by the present invention. Preferably, the variant comprises at least one but no more than 5, 4, 3, 2 or 1 amino acid alteration (preferably amino acid substitution, preferably conservative substitution) in total over the 6 CDRs, and preferably the heavy chain CDR3 remains unchanged.

In still other embodiments, the present invention provides an anti-Claudin18.2 antibody or an antigen-binding fragment thereof, comprising a heavy chain variable region and a light chain variable region selected from:

(i) a heavy chain variable region set forth in SEQ ID NO: 1 or 3 or an amino acid sequence having at least 80%, 85%, 90%, 95%, 96%, 97%, 98% or 99% identity thereto, and a light chain variable region set forth in SEQ ID NO: 2 or an amino acid sequence having at least 80%, 85%, 90%, 95%, 96%, 97%, 98% or 99% identity thereto; or (ii) a heavy chain variable region set forth in SEQ ID NO: 21 or an amino acid sequence having at least 80%, 85%, 90%, 95%, 96%, 97%, 98% or 99% identity thereto, and a light chain variable region set forth in SEQ ID NO: 22 or an amino acid sequence having at least 80%, 85%, 90%, 95%, 96%, 97%, 98% or 99% identity thereto; or (iii) a heavy chain variable region set forth in SEQ ID NO: 23 or an amino acid sequence having at least 80%, 85%, 90%, 95%, 96%, 97%, 98% or 99% identity thereto, and a light chain variable region set forth in SEQ ID NO: 24 or an amino acid sequence having at least 80%, 85%, 90%, 95%, 96%, 97%, 98% or 99% identity thereto; or (iv) a heavy chain variable region set forth in SEQ ID NO: 38 or 40 or an amino acid sequence having at least 80%, 85%, 90%, 95%, 96%, 97%, 98% or 99% identity thereto, and a light chain variable region set forth in SEQ ID NO: 39 or an amino acid sequence having at least 80%, 85%, 90%, 95%, 96%, 97%, 98% or 99% identity thereto; or (v) a heavy chain variable region set forth in SEQ ID NO: 44 or an amino acid sequence having at least 80%, 85%, 90%, 95%, 96%, 97%, 98% or 99% identity thereto, and a light chain variable region set forth in SEQ ID NO: 45 or an amino acid sequence having at least 80%, 85%, 90%, 95%, 96%, 97%, 98% or 99% identity thereto; or (vi) a heavy chain variable region set forth in SEQ ID NO: 46 or an amino acid sequence having at least 80%, 85%, 90%, 95%, 96%, 97%, 98% or 99% identity thereto, and a light chain variable region set forth in SEQ ID NO: 47 or an amino acid sequence having at least 80%, 85%, 90%, 95%, 96%, 97%, 98% or 99% identity thereto; or (vii) a heavy chain variable region set forth in SEQ ID NO: 48 or an amino acid sequence having at least 80%, 85%, 90%, 95%, 96%, 97%, 98% or 99% identity thereto, and a light chain variable region set forth in SEQ ID NO: 49 or an amino acid sequence having at least 80%, 85%, 90%, 95%, 96%, 97%, 98% or 99% identity thereto; or (viii) a heavy chain variable region set forth in SEQ ID NO: 50 or an amino acid sequence having at least 80%, 85%, 90%, 95%, 96%, 97%, 98% or 99% identity thereto, and a light chain variable region set forth in SEQ ID NO: 51 or an amino acid sequence having at least 80%, 85%, 90%, 95%, 96%, 97%, 98% or 99% identity thereto; or (ix) a heavy chain variable region set forth in SEQ ID NO: 52 or an amino acid sequence having at least 80%, 85%, 90%, 95%, 96%, 97%, 98% or 99% identity thereto, and a light chain variable region set forth in SEQ ID NO: 53 or an amino acid sequence having at least 80%, 85%, 90%, 95%, 96%, 97%, 98% or 99% identity thereto.

In one embodiment, preferably, the anti-Claudin18.2 antibody or the antigen-binding fragment thereof of the present invention comprises heavy and light chain variable region sequences or variants thereof of any one of the exemplary antibodies 25C7A5 and humanized antibodies thereof (HZ1 and HZ2) and 2D3A11 and humanized antibodies thereof (HZ1 and HZ2) of the present invention; for example, it is an antibody having the same CDR sequences as one of the exemplary antibodies, and having the same or different framework region sequences.

In some preferred embodiments, the anti-Claudin18.2 antibody or the antigen-binding fragment thereof comprises a heavy chain variable region and a light chain variable region, wherein the heavy chain variable region comprises an amino acid sequence set forth in SEQ ID NO: 21 or an amino acid sequence having at least 95%, 96%, 97%, 98% or 99% sequence identity thereto, and wherein the light chain variable region comprises an amino acid sequence set forth in SEQ ID NO: 22 or an amino acid sequence having at least 95%, 96%, 97%, 98% or 99% sequence identity thereto. Preferably, the antibody or the antigen-binding fragment comprises a heavy chain variable region of SEQ ID NO: 21 and a light chain variable region of SEQ ID NO: 22.

In still other preferred embodiments, the anti-Claudin18.2 antibody or the antigen-binding fragment thereof comprises a heavy chain variable region and a light chain variable region, wherein the heavy chain variable region comprises an amino acid sequence set forth in SEQ ID NO: 1 or 3 or an amino acid sequence having at least 95%, 96%, 97%, 98% or 99% sequence identity thereto, and wherein the light chain variable region comprises an amino acid sequence set forth in SEQ ID NO: 2 or an amino acid sequence having at least 95%, 96%, 97%, 98% or 99% sequence identity thereto. Preferably, the antibody is a humanized antibody. More preferably, the heavy chain variable region of the antibody has a framework region sequence derived from a human germline, and preferably has amino acid Q or E, preferably amino acid Q, at position H6 numbered according to the Kabat scheme in the heavy chain variable region.

In still other preferred embodiments, the antibody or the antigen-binding fragment comprises a heavy chain variable region of SEQ ID NO: 1 and a light chain variable region of SEQ ID NO: 2.

In still other preferred embodiments, the antibody or the antigen-binding fragment comprises a heavy chain variable region of SEQ ID NO: 3 and a light chain variable region of SEQ ID NO: 2.

In some preferred embodiments, the anti-Claudin18.2 antibody or the antigen-binding fragment thereof comprises a heavy chain variable region and a light chain variable region, wherein the heavy chain variable region comprises an amino acid sequence set forth in SEQ ID NO: 23 or an amino acid sequence having at least 95%, 96%, 97%, 98% or 99% sequence identity thereto, and wherein the light chain variable region comprises an amino acid sequence set forth in SEQ ID NO: 24 or an amino acid sequence having at least 95%, 96%, 97%, 98% or 99% sequence identity thereto. Preferably, the antibody or the antigen-binding fragment comprises a heavy chain variable region of SEQ ID NO: 23 and a light chain variable region of SEQ ID NO: 24.

In still other preferred embodiments, the anti-Claudin18.2 antibody or the antigen-binding fragment thereof comprises a heavy chain variable region and a light chain variable region, wherein the heavy chain variable region comprises an amino acid sequence set forth in SEQ ID NO: 38 or 40 or an amino acid sequence having at least 95%, 96%, 97%, 98% or 99% sequence identity thereto, and wherein the light chain variable region comprises an amino acid sequence set forth in SEQ ID NO: 39 or an amino acid sequence having at least 95%, 96%, 97%, 98% or 99% sequence identity thereto. Preferably, the antibody is a humanized antibody. More preferably, the heavy chain variable region of the antibody has a framework region sequence derived from a human germline, and preferably has amino acid Q or E, preferably amino acid Q, at position H6 numbered according to the Kabat scheme in the heavy chain variable region.

In still other preferred embodiments, the antibody or the antigen-binding fragment comprises a heavy chain variable region of SEQ ID NO: 38 and a light chain variable region of SEQ ID NO: 39.

In still other preferred embodiments, the antibody or the antigen-binding fragment comprises a heavy chain variable region of SEQ ID NO: 40 and a light chain variable region of SEQ ID NO: 39.

In some embodiments, the antibody of the present invention may comprise a heavy chain constant region and/or a light chain constant region. Preferably, the heavy chain constant region is a heavy chain constant region derived from a human immunoglobulin. Preferably, the light chain constant region is a light chain constant region derived from a human immunoglobulin.

The heavy chain constant region contained in the antibody of the present invention may be of any isotype or subtype, e.g., a heavy chain constant region of IgG1, IgG2, IgG3, or IgG4 isotype. Thus, in some embodiments, the present invention provides an anti-Claudin18.2 antibody, comprising an IgG1, IgG2, IgG3 or IgG4 heavy chain constant region, preferably an IgG1 heavy chain constant region, particularly a human IgG1 heavy chain constant region.

The light chain constant region contained in the antibody of the present invention may be a κ light chain constant region or a λ light chain constant region. Thus, in some embodiments, the present invention provides an anti-Claudin18.2 antibody, comprising a κ light chain constant region or a λ light chain constant region, and preferably the antibody of the present invention comprises a human κ light chain constant region.

In some embodiments, the antibody according to the present invention is an IgG1 antibody, particularly an IgG1κ or IgG1λ isotype. More preferably, the antibody according to the present invention is a human IgG1 κ antibody.

In some embodiments, the anti-Claudin18.2 antibody of the present invention comprises a human IgG1 heavy chain constant region. Preferably, the heavy chain constant region comprises an amino acid sequence of SEQ ID NO: 4, or an amino acid sequence comprising at least one, two or three but no more than 20, 10 or 5 amino acid alterations relative to the amino acid sequence of SEQ ID NO: 4, or a sequence having at least 95%-99% identity to the amino acid sequence of SEQ ID NO: 4.

In some embodiments, the anti-Claudin18.2 antibody of the present invention comprises a human κ light chain constant region. Preferably, the light chain constant region comprises an amino acid sequence of SEQ ID NO: 5, or an amino acid sequence comprising at least one, two or three but no more than 20, 10 or 5 amino acid alterations relative to the amino acid sequence of SEQ ID NO: 5, or a sequence having at least 95%-99% identity to the amino acid sequence of SEQ ID NO: 5.

In some preferred embodiments, the antibody of the present invention comprises a heavy chain sequence and a light chain sequence selected from:

(a) a heavy chain sequence comprising an amino acid sequence of SEQ ID NO: 18, and a light chain sequence comprising an amino acid sequence of SEQ ID NO: 20;

(b) a heavy chain sequence comprising an amino acid sequence of SEQ ID NO: 19, and a light chain sequence comprising an amino acid sequence of SEQ ID NO: 20;

(c) a heavy chain sequence comprising an amino acid sequence of SEQ ID NO: 41, and a light chain sequence comprising an amino acid sequence of SEQ ID NO: 43; and (d) a heavy chain sequence comprising an amino acid sequence selected from SEQ ID NO: 42, and a light chain sequence comprising an amino acid sequence of SEQ ID NO: 43. The present invention further provides a variant of an antibody comprising any one of (a)-(d) above, wherein the variant has an amino acid alteration in the heavy chain sequence and/or the light chain sequence. Preferably, the variant comprises an amino acid sequence comprising at least one, two or three but no more than 20, 10 or 5 amino acid alterations, or an amino acid sequence having at least 80%, 85%, 90%, 92%, 95%, 97%, 98%, 99% or more identity to the corresponding antibody, in the heavy chain sequence or the light chain sequence or both. Preferably, the amino acid alterations do not occur in the CDRs, and more preferably, the amino acid alterations do not occur in the variable regions.

The present invention further provides variants of any of the antibodies described herein, particularly variants of any one of the exemplary antibodies 25C7A5 and humanized antibodies thereof (HZ1 and HZ2) and 2D3A11 and humanized antibodies thereof (HZ1 and HZ2) of the present invention. The antibody variants of the present invention preferably retain at least 60%, 70%, 80%, 90%, or 100% of the biological activity (e.g., antigen-binding ability) of the antibody prior to alterations. More preferably, the alterations do not result in loss of binding ability of the antibody variants to an antigen, but optionally confer properties such as increased affinity for the antigen and different effector functions. It will be understood that the heavy or light chain variable regions or CDRs of the antibody may be altered independently or in combination. In addition, the Fc region of the antibody may also be altered. The alterations in the Fc region may be made alone or in combination with the alterations in the framework regions and/or CDRs described above. The Fc region may be altered, for example, to alter one or more functions of the antibody, such as serum half-life, complement fixation, Fc receptor binding, and/or antigen-dependent cytotoxicity. In addition, the antibody of the present invention may be chemically modified (e.g., linked to PEG), or its glycosylation pattern may be altered.

In some embodiments, the antibody of the present invention is preferably a monospecific antibody. However, in some embodiments, the antibody of the present invention may also be a multispecific antibody comprising a first binding specificity for Claudin18.2 and a binding specificity for another antigen, e.g., a second and/or third binding specificity for another antigen expressed on the surface of a tumor cell.

In some embodiments, the anti-Claudin18.2 antibody or the antigen-binding fragment thereof of the present invention has one or more of the following properties:

(i) binding with high affinity to human Claudin18.2 expressed on the cell surface, but not binding or substantially not binding to human Claudin18.1;
(ii) having cross-reactivity with cynomolgus monkey, mouse or rat Claudin18.2;
(iii) killing cells expressing Claudin18.2 on the surface, particularly tumor cells such as gastric cancer cells;
(iv) having ADCC activity;
(v) having CDC activity; and
(vi) having Claudin18.2 receptor-mediated endocytic activity.

In some embodiments, the antibody of the present invention has high binding affinity and high binding specificity for Claudin18.2. Herein, preferably, the binding affinity and binding specificity of the antibody of the present invention for Claudin18.2 and/or for Claudin18.1 are determined by an FACS assay or a cell-based ELSA assay (e.g. the assay described in Example I-7). In one embodiment, in a cell-based assay, the binding affinity of the antibody of the present invention for Claudin18.1 is at least 10-fold, 100-fold, $10^3$-fold, $10^4$-fold, $10^5$-fold, or $10^6$-fold lower relative to the binding affinity of the antibody for Claudin 18.2. In one embodiment, preferably, the antibody of the present invention does not bind or substantially does not bind to Claudin18.1-expressing cells.

In one embodiment, in a cell-based assay, for example, in a cell-based ELISA assay performed using a recombinant cell line with a human Claudin18.2 expression positive rate of greater than 95% or greater than 98%, the antibody of the present invention exhibits high binding affinity for human Claudin 18.2, and has an $EC_{50}$ value of less than 300 ng/mL, particularly less than about 100 ng/mL, e.g., about 1 ng/mL to 50 ng/mL and preferably less than about 20 ng/mL. Preferably, the assay is performed according to the cell-based ELISA assay described in Example I-7. Preferably, the assay is performed using a recombinant HEK-293T cell line stably expressing human Claudin18.2.

In yet another embodiment, in a cell-based assay, the antibody of the present invention has comparable or greater binding affinity for human Claudin 18.2 relative to the reference antibody IMAB362. In some embodiments, compared to the reference antibody IMAB362, the antibody of the present invention exhibits comparable cell binding affinity on cells with a high human Claudin 18.2 expression positive rate (e.g., a positive rate of greater than 95%) on the surface; in other embodiments, the antibody of the present invention exhibits stronger cell binding affinity on cells with a moderate-to-low (e.g., less than 50%, such as about 2%-30%) human Claudin 18.2 expression positive rate on the surface. In the assay, a mammalian cell line recombinantly expressing human Claudin18.2, such as HEK29 or L929 or NUGC4 cells, or a tumor cell line endogenously expressing human Claudin18.2, such as NUGC4 cells, can also be used. Preferably, the assay is performed using a cell-based ELISA assay as described in Example I-7, or using an FACS assay as described in Example I-8. Preferably, compared to the reference antibody IMAB362, the antibody of the present invention exhibits stronger cell binding activity to cells with a lower average level of Claudin18.2 cell surface expression, such as NUGC4 cells endogenously expressing human Claudin18.2.

In one embodiment, in a cell-based assay, the antibody of the present invention exhibits no specific binding to Claudin 18.1. This binding property of the antibody to Claudin18.1-expressing cells can be determined in an FACS assay, optionally relative to a negative and/or positive control. Preferably, in the assay, the percentage of positive cell staining of the antibody and/or the fluorescence staining intensity value of the cells are determined. In one embodiment, using a recombinant cell line with a human Claudin18.1 expression positive rate of greater than 95% or greater than 98%, the positive cell rate of the antibody of the present invention is less than 3% (more preferably less than 2%, still more preferably less than 1%, even more preferably less than 0.7%), and preferably, the median and/or average fluorescence signal intensity produced by the antibody of the present invention is comparable (e.g., ±20%, or preferably ±10%) to the median/average signal produced by an isotype control antibody. Preferably, the assay is performed according to the FACS assay described in Example I-10. Preferably, the assay is performed using a recombinant HEK-293T cell line stably expressing human Claudin18.1.

In one embodiment, the antibody of the present invention has ADCC activity. The ADCC activity of the antibody of the present invention can be assayed as described in Example I-11. Preferably, in the assay, the antibody of the present invention exhibits an $EC_{50}$ value of less than about 100 ng/mL, e.g., 80-50 ng/mL, or more preferably less than about 50 ng/mL.

In still other embodiments, the antibody of the present invention has CDC activity. The CDC activity of the antibody of the present invention can be assayed as described in Example I-12. Preferably, in the assay, the antibody of the present invention exhibits CDC activity of less than about 5 g/mL, e.g., about 1-4 g/mL.

In still other embodiments, the antibody of the present invention has endocytic activity after binding to the receptor Claudin18.2 on the cell membrane surface. The endocytic activity of the antibody of the present invention can be assayed as described in Example I-13. Preferably, in the endocytic activity evaluation assay, the antibody of the present invention has an endocytosis rate of, for example, at least 10%, e.g., 10%-25%, preferably at least 20%, after 4 h at 37° C.

In yet another embodiment, the anti-Claudin18.2 antibody or the antigen-binding fragment thereof of the present invention further has one or more of the following properties: (vii) a good stability; and (viii) favorable pharmacokinetic properties.

In one embodiment, the stability of the antibody of the present invention can be assayed as described in Example I-14. Preferably, in an accelerated stability assay, the antibody, after being left to stand at 37° C. for 3-14 days, has an SEC-HPLC purity of not less than 95%, preferably not less than 97%, and/or a non-reduced CE-SDS purity of not less than 90%, preferably not less than 93%, and/or a reduced CE-SDS purity of not less than 90%, preferably not less than 95%.

More preferably, in a repeated freeze-thaw assay, the antibody has an SEC-HPLC purity of not less than 95%, preferably not less than 97%, after 4 or 8 repeated freeze-thaw cycles at −80° C.

In another embodiment, the pharmacokinetic properties of the antibody of the present invention can be assayed as described in Example I-15.

II. Polynucleotide, Vector, and Host

In yet another aspect, the present invention provides a nucleic acid encoding any of the above anti-Claudin18.2 antibodies or fragments thereof. Further provided are a vector comprising the nucleic acid, and a host cell comprising the nucleic acid or the vector.

In one embodiment, the present invention provides one or more vectors comprising the nucleic acid of the present invention, including cloning vectors and expression vectors. In one embodiment, the vector is an expression vector, such as a eukaryotic expression vector. The vector that can be used in the present invention includes, but is not limited to, a virus, a plasmid, a cosmid, a λ phage or a yeast artificial chromosome (YAC).

In one embodiment, the present invention provides a host cell comprising the vector of the present invention. The suitable host cell for cloning or expressing the vector encoding the antibody includes a prokaryotic or eukaryotic cell. For example, the antibody can be produced in bacteria, particularly when glycosylation and Fc effector functions are not required. After expression in bacteria, such as *E. coli*, the antibody can be isolated from the bacterial cell paste in the soluble fraction and can be further purified. In yet another embodiment, the host cell is a eukaryotic cell. In another embodiment, the host cell is selected from a yeast cell, a mammalian cell, and other cells suitable for preparing an antibody or an antigen-binding fragment thereof. Examples of useful mammalian host cell lines include: monkey kidney CV1 line (COS-7) transformed with SV40; human embryonic kidney line (293HEK or 293 cells); Chinese hamster ovary (CHO) cells, including $DHFR^-$ CHO cells; and myeloma cell lines such as Y0, NS0 and Sp2/0.

III. Preparation of Antibodies

In yet another aspect, the present invention provides a method for preparing the anti-Claudin18.2 antibody of the present invention. In one embodiment, the method of the present invention comprises culturing a host cell comprising a nucleic acid encoding the antibody of the present invention under conditions suitable for expressing the antibody, and optionally recovering the antibody from the host cell (or the host cell culture medium). For recombinant production of the anti-Claudin18.2 antibody, an isolated or artificially synthesized or recombinantly synthesized nucleic acid encoding the antibody (e.g., the antibody described above) can be inserted into one or more vectors for further cloning and/or expression in the host cell. Using conventional procedures, such nucleic acids can be readily isolated and sequenced, e.g., isolated from hybridoma cells by using oligonucleotide probes that are capable of specifically binding to genes encoding the heavy and light chains of the antibody.

IV. Immunoconjugate

In yet another aspect, the present invention provides an immunoconjugate produced by conjugating the antibody of the present invention to a heterologous molecule. In one embodiment, in the immunoconjugate, the antibody (or the antigen-binding fragment thereof) of the present invention is conjugated to a therapeutic agent or a diagnostic agent or a detectable agent. In some embodiments, the antibody of the present invention can be conjugated to the heterologous molecule in the form of a full-length antibody or an antibody fragment. In the conjugates, linkers can be used to covalently link different entities of the conjugates. Suitable linkers include chemical linkers or peptide linkers. Advantageously, the linkers are "cleavable linkers" that facilitate the release of the polypeptides following delivery to a target site. For example, acid-labile linkers, peptidase-sensitive linkers, photolabile linkers, dimethyl linkers or disulfide-containing linkers can be used.

In embodiments of conjugation to a therapeutic agent, the therapeutic agent suitable for the conjugate includes, but is not limited to, a cytotoxin (e.g., a cytostatic agent or a cytotoxic agent), a drug, or a radioisotope. In embodiments of conjugation to a diagnostic agent or a detectable agent, such conjugates can be used as part of a clinical testing method (e.g., to determine the efficacy of a specific therapy) for monitoring or predicting the onset, development, progression, and/or severity of a disease or disorder. Such diagnosis and detection can be achieved by conjugating the antibody to the detectable agent, which includes, but is not limited to, a variety of enzymes, such as horseradish peroxidase; prosthetic groups, such as streptavidin/biotin and avidin/biotin; fluorescent substances; luminescent substances; radioactive substances; and positron-emitting metals and non-radioactive paramagnetic metal ions used in various positron emission tomography techniques.

V. Pharmaceutical Composition and Pharmaceutical Formulation

The present invention further comprises a composition (including a pharmaceutical composition or a pharmaceutical formulation) comprising the anti-Claudin18.2 antibody or the immunoconjugate thereof, and a composition comprising a polynucleotide encoding the anti-Claudin18.2 antibody or the immunoconjugate thereof. Such compositions can further optionally comprise a suitable pharmaceutical auxiliary material, such as a pharmaceutical carrier and a pharmaceutical excipient known in the art, including buffers. For use and application of the excipients, see Handbook of Pharmaceutical Excipients, 5th Ed., R. C. Rowe, P. J. Seskey and S. C. Owen, Pharmaceutical Press, London, Chicago. In some embodiments, the pharmaceutical formulation comprising the present invention can be prepared by mixing the anti-Claudin18.2 antibody or the immunoconjugate of the present invention of a desired purity with one or more optional pharmaceutical auxiliary materials (Remington's Pharmaceutical Sciences, 16th Ed., Osol, A. eds. (1980)).

In the pharmaceutical composition and the pharmaceutical formulation of the present invention, the antibody of the present invention can be the sole active agent, or can be combined with an additional therapeutic agent. The therapeutic agent that can be combined with the antibody of the present invention includes, but is not limited to, therapeutic agents having beneficial therapeutic efficacy for the disease and/or disorder to be treated. For example, the active ingredients can be those required for a specific indication being treated, preferably those having complementary activities that do not adversely affect one another, For example, additional pharmaceutical ingredients that provide anti-cancer activity can be provided. The antibody of the present invention is suitably present in combination with the active ingredients in an amount effective for an intended purpose in the pharmaceutical composition and the pharmaceutical formulation.

VI. Combination Product

In yet another aspect, the present invention further provides a combination product comprising the antibody or the antigen-binding fragment thereof, the multispecific antibody or the immunoconjugate of the present invention, and one or more additional therapeutic agents (e.g., chemotherapeutic agents, other antibodies, cytotoxic agents, antineoplastic agents, etc.). The components that make up the combination product, such as the antibody of the present invention and the additional therapeutic agents, can be formulated separately in different formulations and preferably contained in different containers. The mode and order of administration of the components of the combination product can be determined by those skilled in the art based on factors such as the disease to be treated, the individual condition and the like. The combination product of the present invention can be used in a treatment method of the present invention. In some embodiments, the present invention provides a combination product, wherein the additional therapeutic agent refers to, for example, a therapeutic agent, such as an antibody, which is effective to stimulate an immune response and thus further enhance, stimulate or upregulate the immune response in a subject. In some embodiments, the combination product is used for preventing or treating a Claudin18.2-positive tumor.

VII. Method and Use

In one aspect, the present invention provides a method for using the Claudin18.2 antibody and the antigen-binding fragment thereof of the present invention and use thereof, for example, in vivo and in vitro for:

(1) targeting and binding to tumor cells expressing CLAUDIN 18.2 on the surface; and/or (2) inducing ADCC activity and/or CDC activity against tumor cells expressing CLAUDIN 18.2 on the surface; and (3) inhibiting and/or killing tumor cells expressing CLAUDIN 18.2 on the surface.

In some embodiments, the method and use of the present invention relate to the treatment of a disease in an individual or a subject. In other embodiments, the method and use of the present invention relate to detecting the presence of Claudin18.2 in a sample from, for example, a subject. In still other embodiments, the present invention further provides use of the anti-Claudin18.2 antibody or the antigen-binding fragment thereof of the present invention in the preparation of a product (e.g., a pharmaceutical composition or a pharmaceutical product or a combination product or a test product) for the above-mentioned use.

Treatment Method and Use

In one aspect, the present invention provides use of the antibody of the present invention in the prevention and/or treatment of a CLAUDIN 18.2-positive tumor in a subject, comprising administering the antibody of the present invention in a prophylactically and/or therapeutically effective amount.

In the method of the present invention, administration of the antibody of the present invention may comprise: 1) a therapeutic measure that cures, slows, alleviates symptoms of the diagnosed pathological condition or disease, and/or stops progression of the diagnosed pathological condition or disease; or 2) a prophylactic or preventative measure that prevents and/or slows the progression of the pathological condition or disease. Thus, in the method of the present invention, the subject may be an individual already suffering from the disease, an individual susceptible to the disease, or an individual for whom the disease is to be prevented. The individual will benefit from the therapeutic measure or the prophylactic measure and exhibit an alleviation or amelioration in the occurrence, recurrence or progression of the disease, disorder, condition, and/or symptom as compared to an individual not receiving the treatment. In some embodiments, the present invention relates to the treatment of the disease or disorder. In other embodiments, the present invention relates to the prevention of the disease or disorder.

In some embodiments, the antibody of the present invention used in the method of the present invention comprises an Fc region that induces an immune effector function and, upon binding to a cell (e.g., a cancer cell) expressing CLDN18.2 on the surface, induces an immune effect, e.g., ADCC and/or CDC activity. Thus, in one embodiment of the treatment method of the present invention, the antibody or the fusion, conjugate or composition thereof of the present invention mediates cancer cell killing by inducing CDC-mediated cell lysis or ADCC-mediated cell lysis, or both.

The antibody of the present invention (as well as the pharmaceutical composition or immunoconjugate comprising same, and any additional therapeutic agent) may be administered by any suitable route, including parenteral administration, intratumoral administration, and intranasal administration. Parenteral infusion includes intramuscular, intravenous, intra-arterial, intraperitoneal or subcutaneous administration. Administration may be performed by any suitable route, e.g., by injection, e.g., intravenous or subcutaneous injection, depending in part on whether the medication is for short-term or long-term. Various administration schedules are encompassed herein, including, but not limited to, single administration or multiple administrations at multiple time points, bolus injection, and pulse infusion.

Detection Application

The present invention further provides a method and kit for detecting Claudin18.2 in a sample, wherein the method comprises: (a) contacting the sample with the antibody or the antigen-binding fragment or immunoconjugate thereof of the present invention; and (b) detecting the formation of a complex by the antibody or the antigen-binding fragment or immunoconjugate thereof and a Claudin18.2 protein. In some embodiments, the sample is from a cancer patient, e.g., a patient with a digestive system cancer, such as gastric cancer, pancreatic cancer, or esophageal cancer. The detection may be in vitro or in vivo.

The term "detection" or "detect" used herein includes quantitative and qualitative detections, and exemplary detections may involve immunohistochemistry, immunocytochemistry, flow cytometry (e.g., FACS), magnetic beads complexed with antibody molecules, ELISA assay, and PCR (e.g., RT-PCR). In certain embodiments, the biological sample is blood, serum, or other liquid samples of biological origin. In certain embodiments, the biological sample includes cells or tissues. In some embodiments, the biological sample is from a hyperproliferative or cancerous lesion. In certain embodiments, the Claudin18.2 to be detected is human Claudin18.2.

In one embodiment, the anti-Claudin18.2 antibody is used to select a subject suitable for treatment with the anti-Claudin18.2 antibody. In yet another embodiment, the antibody of the present invention can be used to diagnose a cancer or tumor, e.g., to evaluate (e.g., monitor) the treatment or progression, diagnosis, and/or staging of the disease (e.g., the hyperproliferative or cancerous disease) described herein in a subject.

In certain embodiments, provided is a labeled anti-Claudin18.2 antibody. The label includes, but is not limited to, a label or moiety that is detected directly, e.g., a fluorescent label, a chromophoric label, an electron-dense label, a chemiluminescent label, and a radioactive label, and a moiety that is detected indirectly, such as an enzyme or a ligand, for example, by enzymatic reaction or molecular interaction.

These and other aspects and embodiments of the present invention are described in the drawings (with brief description of the drawings immediately following) and in the following detailed description of the present invention and are illustrated in the following examples. Any or all of the features described above and throughout the present application may be combined in various embodiments of the present invention. The present invention will be further illustrated with reference to the following examples. However, it should be understood that the examples are for illustrative purposes, and should not be construed as constituting any limitation.

EXAMPLES

Example I. Preparation and Characterization of Anti-Claudin18.2

Example 1. Construction and Identification of Claudin18.2- and Claudin18.1-Expressing Cell Lines The amino acid sequence of human Claudin18.2 was referenced from NP_001002026.1 in the protein database of NCBI. The amino acid sequence of human Claudin18.1 was referenced from NP_057453.1 in the protein database of NCBI. The amino acid sequence of cynomolgus monkey Claudin18.2 was referenced from XP_015300615.1 in the protein database of NCBI. The amino acid sequence of mouse Claudin18.2 was referenced from NP_001181850.1 in the protein database of NCBI. The amino acid sequence of rat Claudin18.2 was referenced from NP_001014118.1 in the protein database of NCBI. The above amino acid sequences were codon-optimized by GenScript Biotech Corporation and synthesized on a lentiviral vector pLVX or a pCDNA3.4 vector.

Viruses were prepared by a lentiviral packaging system, and the obtained viruses were used to infect HEK293T, L929, and CHO cells, respectively. Puromycin screening was then performed to obtain stable cell lines of CHO-Claudin18.2 (human), HEK293T-Claudin18.1 (human), HEK293T-Claudin18.2 (human), L929-Claudin18.2 (human), HEK293T-Claudin18.2 (cynomolgus monkey), HEK293T-Claudin18.2 (rat), and HEK293T-Claudin18.2 (mouse).

NUGC4 is a gastric cancer tumor cell line endogenously expressing Claudin18.2, and NUGC4 (purchased from Nanjing Cobioer, CBP60493) was selected for subsequent experiments. A stable cell line NUGC4-Claudin18.2 (human) recombinantly overexpressing human Claudin18.2 was also purchased (from Kyinno Biotechnology Co., Ltd., Beijing, KC-1471) for subsequent experiments.

The positive rate of Claudin18.2 was determined by flow cytometry (FACS). The experimental procedures were as follows: The adherent cultured cells were digested, collected by centrifugation, and washed three times with pre-cooled PBS. The cells were resuspended in 1% BSA (in PBS) and added to a 96-well pointed bottom plate at $3\times10^5$ cells/well, with a volume of 50 μL per well. An IMAB362 antibody (with a sequence from the patent CN 101312989 B, obtained by expression and purification with 293E cells using the heavy chain variable region amino acid sequence SEQ ID NO: 135 and light chain variable region amino acid sequence SEQ ID NO: 142 of the antibody 175D10 synthesized by General Biosystems (Anhui) Co., Ltd.) was diluted to 40 g/mL with 1% BSA (in PBS) and added to the cells at 50 μL/well to achieve a final antibody concentration of 20 g/mL. The mixture was well mixed and incubated at 4° C. for 1 h. The cells were collected by centrifugation, washed three times with pre-cooled PBS, and resuspended in 50 μL of 1% BSA (in PBS). 1 μL of an anti-human fluorescent secondary antibody (APC: Biolegend-410712 or PE: BioLegend-410708) was then added to each well, and the mixture was well mixed and incubated at 4° C. for 0.5 h. The cells were collected by centrifugation, washed three times with pre-cooled PBS, resuspended in 200 μL of PBS, and assayed on a machine (flow cytometer model: Sony-LE-SA3800GA or Beckman-Cytoflex) to obtain the APC fluorescence signal value and the percentage of positively stained cells (positive rate (%)).

The positive rate of Claudin18.1 cells was determined by the same method using the sera of immunized mice.

The positive rate results of flow cytometry are shown in FIGS. 1A-1I, indicating that all the above stable cell lines exhibited high (>95%) positive rates, while the NUGC4 cells showed a Claudin18.2 expression positive rate of 23.8%.

Example 2. Preparation of Anti-Human Claudin18.2 Murine Monoclonal Antibodies 24 wild-type mice, aged 5-6 weeks and from 3 strains: Balb/C, KM and CD01, were selected and immunized using the pCDNA3.4-Claudin18.2 plasmid, CHO-Claudin18.2 (human) cells, and L929-Claudin18.2 (human) cells. After 3-4 rounds of immunization, serum titers were detected using flow cytometry. The experimental procedures were as follows: The adherent cultured HEK293T-Claudin18.1 (human) and HEK293T-Claudin18.2 (human) cells were digested, collected by centrifugation, then washed three times with pre-cooled PBS, resuspended in PBS (containing 1% BSA), and added to a 96-well pointed bottom plate at $3\times10^5$ cells/well. Serum subjected to gradient dilution was added, and the mixture was incubated at 4° C. for 1 h. The cells were washed three times with pre-cooled PBS, and then 1 μL of an anti-mouse IgG fluorescent secondary antibody was added to each well. The mixture was incubated at 4° C. for 0.5 h, and the cells were washed three times with pre-cooled PBS, then resuspended, and assayed on a flow cytometer. Mice with high affinity for HEK293T-Claudin18.2 (human) and low affinity for HEK293T-Claudin18.1 (human) were selected as candidates for fusion, and the candidate mice were numbered 61, 64, 79, 89, and 91, respectively.

Cell suspensions were prepared from the spleens and lymph nodes of the mice and mixed with SP2/0 mouse myeloma cells at a 1:1 ratio. The cells were resuspended in a cell electrofusion buffer and subjected to an electrofusion reaction using a BTX-ECM2001 cell electrofusion apparatus. After the electrofusion reaction, the cells were resuspended in a complete fusion medium (RPMI1640+20% FBS+1×HAT), added to a 96-well cell culture plate at 20000-25000 cells/well, and cultured at 37° C. with 5% $CO_2$. After the culture, hybridoma parent clones with higher affinity for human Claudin18.2 were selected by cell-based ELISA using L929-Claudin18.2 (human) cells, and those that could bind to Claudin18.1 were excluded by flow cytometry (FACS) and used for subcloning. After 2 rounds of fusion screening, a total of 52 parent clones were selected for subcloning. 75 cells of each parent clone were added to one 96-well cell culture plate, and a screening medium (RPMI1640+20% FBS+1×HT) was adopted for subcloning culture. Subclone supernatants were taken and screened for monoclonals with higher affinity and no binding to Claudin18.1 by using cell-based ELISA and flow cytometry, which were then subjected to amplification culture. Hybridoma cells were cultured in a serum-free medium, and the collected monoclonal supernatants were purified using packing of the antibody purification medium ProA (GE, Mabselect XL) to obtain murine antibodies.

Example 3. Evaluation of Anti-Human Claudin18.2 Murine Antibodies

The affinity of the anti-human Claudin18.2 murine monoclonal antibodies was evaluated by cell-based ELISA. The experimental procedures were as follows: The day before the experiment, HEK293T-Claudin18.2 (human) cells were plated in a 96-well plate at $5\times10^4$ cells/well. On the day of the experiment, the supernatant was removed, the cells in each well were washed once with 300 μL of PBS, and 100 μL of 4% paraformaldehyde was added to each well for fixation at room temperature for 20 min. Paraformaldehyde was then removed, and the cells in each well were washed twice with 300 μL of PBS. 100 μL of 2% BSA (in PBS) was added to each well, and the mixture was blocked at 37° C. for 2 h. After removing the blocking solution, each antibody subjected to gradient dilution (diluted with 2% BSA (in PBS), starting at g/mL, in a 3-fold gradient, for a total of 11 concentration points) was added to the plate at 100 L/well, and the mixture was incubated at 37° C. for 2 h. The supernatant was removed, and the cells in each well were washed three times with 300 μL of PBST. 100 μL of an anti-mouse IgG HRP secondary antibody (Jackson, cat #115-035-003) in 2% BSA was added to each well, and the mixture was incubated at 37° C. for 1 h. The secondary antibody was then removed, and the cells in each well were washed five times with 300 μL of PBST, followed by the addition of 100 μL of a TMB substrate (Huzhou InnoReagents Co., Ltd.) per well for color development for 5-20 min. The reaction was stopped by adding 50 μL of 2 N HCl to each well, and $OD_{450\ nm}$ values were read on a microplate reader (manufacturer: MD, model: SpectraMax). The values obtained were plotted by GraphPad Prism to calculate the $EC_{50}$ value.

The specificity of the anti-human Claudin18.2 murine monoclonal antibodies was evaluated by flow cytometry (FACS). The experimental procedures were as follows: The adherent cultured HEK293T-Claudin18.1 (human) cells were digested, collected by centrifugation, and washed three times with pre-cooled PBS. The cells were resuspended in 1% BSA (in PBS) and added to a 96-well pointed bottom plate at $3\times10^5$ cells/well, with a volume of 50 μL per well. Each test antibody was diluted to 100 μg/mL with 100 BSA (in PBS) and added to the cells at 50 μL/well to achieve a final antibody concentration of 50 sg/mL. The mixture was well mixed and incubated at 4° C. for 1 h. The cells were collected by centrifugation, washed three times with pre-cooled PBS, and resuspended in 50 μL of 10% BSA (in PBS). 1 μL of a fluorescent secondary antibody (Biolegend, cat #405308) was added to each well, and the mixture was well mixed and incubated at 4° C. for 0.5 h. The cells were collected by centrifugation, washed three times with pre-cooled PBS, resuspended in 200 μL of PBS, and assayed on a machine (flow cytometer model: Sony-LE-SA3800GA). The APC fluorescence signal value was obtained, and the gate was set using an isotype control antibody as a negative control to obtain the percentage of positively stained cells (positive rate (0%)).

The experimental results are shown in Table 1. Clones with higher affinity for HTEK293T-Claudin18.2 and no non-specific binding to HEK293 T-Claudin18.1 were selected for sequencing, and the clones were numbered 1A6G11, 2D3A11, 25C7A5, 40G11H2, 8H11A1, 23F2F2, and 32F7A6, respectively.

TABLE 1

Summary of murine antibody evaluation results

| Clone No. | Affinity HEK293T-18.2 EC50 (ng/mL) | Specificity HEK293T-18.1 Mean APC fluorescence signal value | HEK293T-18.1 Positive rate (%) |
|---|---|---|---|
| 1A6G10 | 5.024 | 111 | 0.16 |
| 15G1B2 | 7.145 | 112 | 0.11 |
| 2D3A11 | 8.143 | 134 | 0.25 |
| 27C12F3 | 9.947 | 140 | 0.59 |
| 27H3A8 | 24.71 | 151 | 0.6 |
| 25C7A5 | 10.49 | 123 | 0.87 |
| 40G11H2 | 7.376 | 160 | 0.98 |
| 24B3B3 | 25.42 | 169 | 1.02 |
| 8H11A10 | 12.32 | 175 | 1.21 |
| 15C12A11 | 20.43 | 230 | 1.21 |
| 34G7B8 | 67.87 | 149 | 1.6 |
| 25B1A11 | 11.74 | 146 | 1.84 |
| 23F2F2 | 6.015 | 222 | 2.16 |
| 6C10G7 | 37.59 | 170 | 2.3 |
| 3G12F5 | 67.42 | 170 | 3.26 |
| 15C12A2 | 8.933 | 639 | 10.6 |
| 13A6D2 | 5.183 | 532 | 18.3 |
| 25F11B8 | 76.49 | 538 | 19 |
| 20G11G2 | 41.15 | 1709 | 21.1 |
| 9B8G6 | 77.46 | 553 | 23.2 |
| 43D2A6 | 2.69 | 1017 | 25.6 |
| 20G1C2 | 20.27 | 850 | 27.2 |
| 40B9B7 | 66.75 | 778 | 45.9 |
| 3G12F7 | 6.149 | 1443 | 51.5 |
| 33A9A4 | 7.272 | 904 | 2.87 |
| 34G7E5 | 10.96 | 968 | 5.32 |
| 32F7A6 | 2.399 | 411 | 0 |
| 9B8D5 | 229 | Not detected | Not detected |
| 10D1G9 | 14.86 | 551 | 2.73 |
| 30B11A5 | 22.45 | 502 | 1.72 |
| 3E9B11 | 23.18 | 472 | 0.38 |
| 39H1G2 | 11.79 | 379 | 0.49 |
| 25H8A7 | 19.94 | 543 | 2.45 |
| 24B1F2 | 13.48 | Not detected | Not detected |

Example 4. Sequencing of Anti-Human Claudin18.2 Murine Monoclonal Antibodies

The above hybridoma cells, about $1\times10^5$ in number, were collected. RNA was extracted by Trizol (Invitrogen, 15596026), and then cDNA was obtained by reverse transcription through PolyA using a PrimeScript RT reagent (TAKARA, RR047A) kit. The forward primers were designed upstream of the heavy chain and the light chain, and the reverse primers were designed in the heavy chain CH1 region and the light chain CL region. The product was amplified by PCR (GoldenStar® T6 Super PCR Mix, Tsingke Biotech, TSE11), and the fragments were recovered using an agarose gel extraction kit, sent to Beijing Tsingke Biotech Co., Ltd. for sequencing, and analyzed by IMGT website to obtain murine antibody sequences. The sequences of the candidate murine antibodies are shown in Table 2.

TABLE 2

| Sequence listing of candidate murine antibodies | | |
|---|---|---|
| Clone No. | Heavy chain variable region (VH) sequence | Light chain variable region (VL) sequence |
| 25C7A5 | SEQ ID NO: 21 | SEQ ID NO: 22 |
| 2D3A11 | SEQ ID NO: 23 | SEQ ID NO: 24 |
| 8H11A10 | SEQ ID NO: 44 | SEQ ID NO: 45 |
| 1A6G10 | SEQ ID NO: 46 | SEQ ID NO: 47 |
| 23F2F2 | SEQ ID NO: 48 | SEQ ID NO: 49 |
| 40G11H | SEQ ID NO: 50 | SEQ ID NO: 51 |
| 32F7A6 | SEQ ID NO: 52 | SEQ ID NO: 53 |

25C7A5 and 2D3A11 were confirmed as candidate antibodies with unique sequences by patent analysis and search of the obtained sequences, which were then subjected to humanization design.

Example 5. Humanization of Anti-Human Claudin18.2 Murine Antibodies

The method of CDR grafting was employed. Firstly, a human germline sequence with the highest homology to the original murine sequence was found by a conventional BLAST method to serve as a template; CDRs of the murine antibody were grafted to the human template to construct a chimera; FR amino acids capable of retaining the original conformation of the murine antibody were analyzed according to the structure, and the corresponding amino acids in the chimera were back-mutated to the murine amino acids to keep the original affinity; and the constructed humanized antibody was subjected to calculation and immunogenicity analysis to find a high-immunogenicity fragment, which was used for replacing a low-immunogenicity fragment. Humanized antibodies, 25C7A5-HZ1, 25C7A5-HZ2, 2D3A11-HZ1 and 2D3A11-HZ2, were obtained, the humanized sequences of which are shown in Table 3.

TABLE 3

| Sequence listing of candidate humanized antibodies | |
|---|---|
| Heavy chain variable region (VH) of 25C7A5-HZ1 | QVQLVQSGAEVKKPGSSVKVSCKASGYTFTNYWLHWVRQAPGQGLEWMGMMHPISGSSNYAQKFQGRATLTVDKSTSTAYMELSSLRSEDTAVYYCARGLLSAMDYWGQGTLVTVSS (SEQ ID NO: 27) |
| Light chain variable region (VL )of 25C7A5-HZ1/25C7A5-HZ2 | EIVLTQSPATLSLSPGERATLSCKASENVKTYVSWYQQKPGQSPRLLIYEASNRYTGVPARFSGSGSATDFTLTISSLEPEDFAVYFCGQTYSFPPTFGQGTKVEIK (SEQ ID NO: 28) |
| Heavy chain variable region (VH) of 25C7A5-HZ2 | QVQLVESGAEVKKPGSSVKVSCKASGYTFTNYWLHWVRQAPGQGLEWMGMMHPISGSSNYAQKFQGRATLTVDKSTSTAYMELSSLRSEDTAVYYCARGLLSAMDYWGQGTLVTVSS (SEQ ID NO: 29) |
| Heavy chain variable region (VH) of 2D3A11-HZ1 | QVQLVQSGAEVKKPGASVKVSCKASGYTFTSYVVHWVRQAPGQGLEWMGYINPYNADSKYSQEFQGRATLTSDKSASTAYMELSSLRSEDMAVYYCSRSYYGNSFDVWGQGTLVTVSS (SEQ ID NO: 30) |
| Light chain variable region (VL) of 2D3A11-HZ1/2D3A11-HZ2 | DIVMTQSPDSLAVSLGERATINCKSSQSLLNSGNQKNYLTWYQQKPGQSPKLLFFWASTRQSGVPDRFSGSGSGTDFTLTISSLQAEDVAVYYCQNDYYFPFTFGQGTKVEIK (SEQ ID NO: 31) |
| Heavy chain variable region (VH) of 2D3A11-HZ2 | QVQLVESGAEVKKPGASVKVSCKASGYTFTSYVVHWVRQAPGQGLEWMGYINPYNADSKYSQEFQGRATLTSDKSASTAYMELSSLRSEDMAVYYCSRSYYGNSFDVWGQGTLVTVSS (SEQ ID NO: 32) |

Example 6. Preparation of Anti-Human Claudin18.2 Humanized Antibodies

Humanized antibodies 25C7A5-HZ1 (with a heavy chain variable region sequence of SEQ ID NO: 1 and a light chain variable region sequence of SEQ ID NO: 2) and 25C7A5-HZ2 (with a heavy chain variable region sequence of SEQ ID NO: 3 and a light chain variable region sequence of SEQ ID NO: 2) and the variable region amino acid sequence of the reference antibody IMAB362 (a sequence from the patent CN 101312989 B, the heavy chain variable region amino acid sequence SEQ ID NO: 135 and light chain variable region amino acid sequence SEQ ID NO: 142 of the antibody 175D10) were codon-optimized, then subjected to gene synthesis (by General Biosystems (Anhui) Co., Ltd.), and constructed on a PTT5 vector. After the synthesis, the plasmid was extracted by direct bacterial shaking, transfected into HEK293E cells by PEImax (Polysciences, 24765-1), and expressed for about 7 days. The supernatant was collected by centrifugation and then purified using MabSelectSure protein A affinity packing (GE). The expressed reference antibody had the same human IgG1 heavy chain constant region (SEQ ID NO: 4) and human Kappa light chain constant region (SEQ ID NO: 5) as the humanized antibodies. The purified antibodies were all exchanged into PBS buffers by ultrafiltration, determined for concentration, and stored at −20° C.

Example 7. Detection of Affinity of Anti-Human Claudin18.2 Humanized Antibodies by Cell-Based ELISA The affinity of the anti-human Claudin18.2 humanized monoclonal antibodies was determined by cell-based ELISA. The cell-based ELISA was conducted as described in Example I-3. Cells selected were L929-Claudin18.2 (human) cells, HEK293T-Claudin18.2 (human) cells and NUGC4-Claudin18.2 (human) cells stably expressing human Claudin18.2 after transfection, and NUGC4 cells endogenously expressing human Claudin18.2.

1) For both L929-Claudin18.2 cells and HEK293T-Claudin18.2 cells, the experimental results are shown in Table 4, indicating that 2D3A11-HZ1, 2D3A11-HZ2, 25C7A5-HZ1 and 25C7A5-HZ2 all had high affinity for both cell lines.

TABLE 4

Affinity results of anti-Claudin18.2 humanized antibodies by cell-based ELISA

| | Affinity detected by cell-based ELISA ($EC_{50}$, ng/mL) | |
|---|---|---|
| Sample name | L929-Claudin18.2 | HEK293T-Claudin18.2 |
| 2D3A11-HZ1 | 17.12 ± 0.85 (N = 2) | 12.67 ± 2.1 (N = 2) |
| 2D3A11-HZ2 | 25.62 | 14.01 ± 2.29 (N = 2) |
| 25C7A5-HZ1 | 13.41 | 11.15 |
| 25C7A5-HZ2 | 14.80 ± 3.1 (N = 2) | 11.17 ± 2.19 (N = 2) |

Note:
N = 2 represents 2 independent replicate experiments.

Figure 2A:
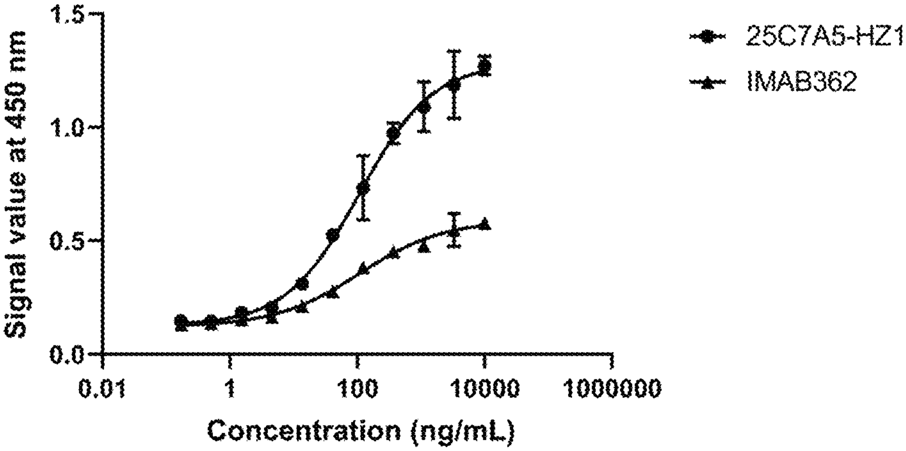
FIGS. 2A-2B show the detection of the affinity of anti-human Claudin18.2 humanized antibodies and a reference antibody IMAB362 for NUGC4-Claudin18.2 (human) cells (FIG. 2A) and NUGC4 cells (FIG. 2B) in a cell-based ELISA assay.

2) For NUGC4-Claudin18.2 cells, the results are shown in Table 5 and FIG. 2A. For the binding to NUGC4-Claudin18.2, the $EC_{50}$ value of 25C7A5-HZ1 was 107.6 ng/mL, and the $EC_{50}$ value of IMAB362 was 109.1 ng/mL; 25C7A5-HZ1 bound to NUGC4-Claudin18.2 with a maximum signal value of 1.284, which was significantly higher than the maximum signal value of 0.591 of IMAB362, indicating that 25C7A5-HZ1 had superior affinity for NUGC4-Claudin18.2 compared to IMAB362.

Figure 2B:
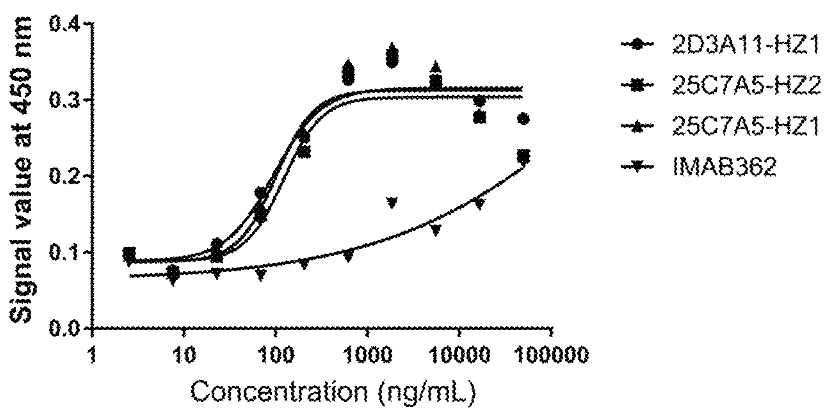

3) For NUGC4 cells, the experimental results are shown in Table 5 and FIG. 2B. 2D3A11-HZ1, 25C7A5-HZ1, and 25C7A5-HZ2 had higher affinity for NUGC4, while IMAB362 had weaker affinity for NUGC4 cells (did not reach the maximum signal value), indicating that 2D3A11-HZ1, 25C7A5-HZ1, and 25C7A5-HZ2 had superior affinity for NUGC4 compared to IMAB362.

TABLE 5

Affinity results of anti-Claudin18.2 humanized antibodies by cell-based ELISA

| | Cell name | | | |
|---|---|---|---|---|
| | NUGC4-Claudin18.2 | | NUCG4 | |
| Antibody name | EC50 ng/mL | Maximum signal value | EC50 ng/mL | Maximum signal value |
| 25C7A5-HZ1 | 107.6 | 1.284 | 101.2 | 0.304 |
| 25C7A5-HZ2 | Not detected | Not detected | 122.5 | 0.313 |
| 2D3A11-HZ1 | Not detected | Not detected | 95.18 | 0.316 |
| IMAB362 | 109.1 | 0.591 | Not detected | Not reached |

Example 8. Detection of Affinity of Anti-Human Claudin18.2 Humanized Antibodies by Cell-Based FACS The affinity of the anti-human Claudin18.2 humanized antibodies was detected by flow cytometry. The experimental procedures were as follows: The adherent cultured HEK293T-Claudin18.2 (human), NUGC4-Claudin18.2 (human) and NUGC4 cells were digested, collected by centrifugation, and washed three times with pre-cooled PBS. The cells were resuspended in 1% BSA (in PBS) and added to a 96-well pointed bottom plate at $3\times10^5$ cells/well, with a volume of 50 μL per well. Each test antibody was diluted with 1% BSA (in PBS) (starting at 100 g/mL, diluted in a 3-fold gradient, for 10 concentration points). The test antibody subjected to gradient dilution was added to the cells at 50 L/well, and the mixture was well mixed and incubated at 4° C. for 1 h. The cells were collected by centrifugation, washed three times with pre-cooled PBS, and resuspended in 50 μL of 1% BSA (in PBS). 1 μL of a fluorescent secondary antibody (Biolegend-410712) was added to each well, and the mixture was well mixed and incubated at 4° C. for 0.5 h. The cells were collected by centrifugation, washed three times with pre-cooled PBS, resuspended in 200 μL of PBS, and assayed on a machine.

Figure 3A:
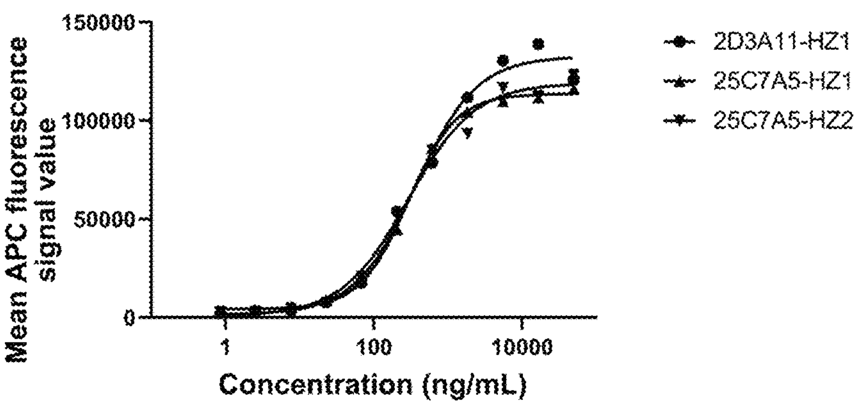
FIGS. 3A-3C show the detection of the affinity of anti-human Claudin18.2 humanized antibodies and a reference antibody IMAB362 for HEK293T-Claudin18.2 (human) cells (FIG. 3A), NUGC4-Claudin18.2 (human) cells (FIG. 3B), and NUGC4 cells (FIG. 3C) by flow cytometry.
Figure 3B:
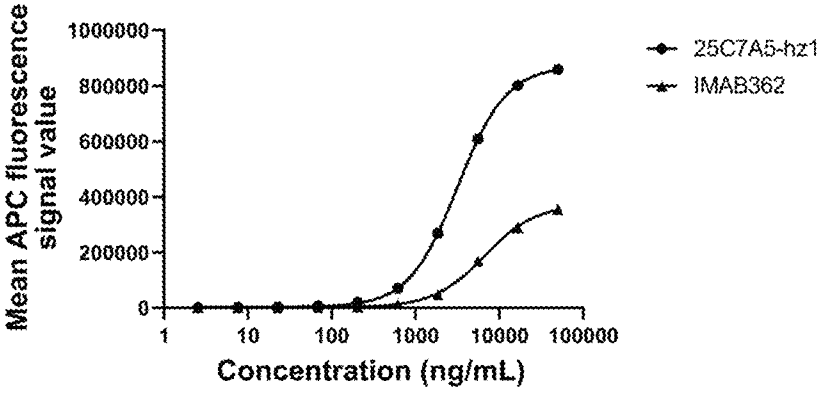
Figure 3C:
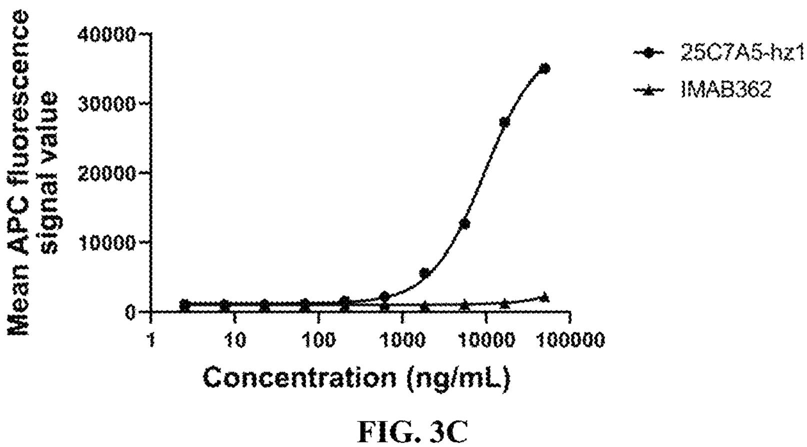

The experimental results are shown in FIGS. 3A-3C and Table 6. 2D3A11-HZ1, 25C7A5-HZ1, and 25C7A5-HZ2 all had high affinity for HEK293T-Claudin18.2 cells (FIG. 3A); for NUGC4-Claudin18.2 cells (FIG. 3B), 25C7A5-HZ1 had an affinity $EC_{50}$ value of 3192 ng/mL, while IMAB362 had an affinity $EC_{50}$ value of 6668 ng/mL, and the maximum signal value of 25C7A5-HZ1 was significantly higher than that of IMAB362, indicating that 25C7A5-HZ1 had superior affinity compared to IMAB362; for NUGC4 cells (FIG. 3C), 25C7A5-HZ1 exhibited significant binding to NUGC4, while IMAB362 exhibited very weak binding to NUGC4, also indicating that 25C7A5-HZ1 had superior affinity compared to IMAB362.

TABLE 6

Affinity results of anti-Claudin18.2 humanized antibodies by cell-based FACS

| | Cell name | | | |
|---|---|---|---|---|
| | HEK293T-Claudin18.2 | | NUCG4- Claudin18.2 | |
| Antibody name | EC50 ng/mL | Maximum signal value | EC50 ng/mL | Maximum signal value |
| 25C7A5-HZ1 | 292 | 113572 | 3192 | 871132 |
| 25C7A5-HZ2 | 292.8 | 119070 | Not detected | Not detected |
| 2D3A11-HZ1 | 368.7 | 132603 | Not detected | Not detected |
| IMAB362 | Not detected | Not detected | 6668 | 373157 |

Example 9. Evaluation of Species Affinity of Anti-Human Claudin18.2 Humanized Monoclonal Antibodies The affinity of the anti-human Claudin18.2 humanized monoclonal antibodies for Claudin18.2 of different species was determined by flow cytometry (FACS). The experimental procedures were as follows: HEK293T-Claudin18.2 (cynomolgus monkey) cells, HEK293T-Claudin18.2 (mouse) cells and HEK293T-Claudin18.2 (rat) cells were digested, collected by centrifugation, washed three times with pre-cooled PBS, resuspended in 1% BSA (in PBS), and added to a 96-well pointed bottom plate at $3\times10^5$ cells/well. Each antibody subjected to gradient dilution was added, and the mixture was incubated at 4° C. for 1 h. The cells were washed three times with pre-cooled PBS, and then 1 μL of a fluorescent secondary antibody (APC: Biolegend-410712) was added to each well. The mixture was incubated at 4° C. for 0.5 h, and the cells were washed three times with pre-cooled PBS, then resuspended, and assayed on a flow cytometer.

Figure 4A:
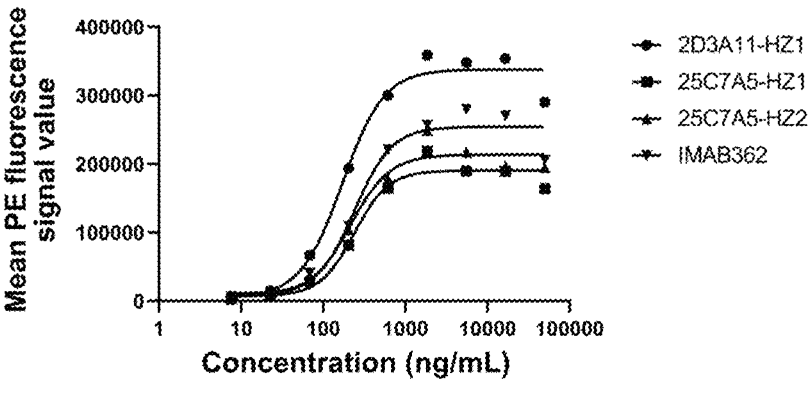
FIGS. 4A-4C show the detection of the affinity of anti-human Claudin18.2 humanized antibodies and a reference antibody IMAB362 for HEK293T-Claudin18.2 (cynomolgus monkey) cells (FIG. 4A), HEK293T-Claudin18.2 (rat) cells (FIG. 4B), and HEK293T-Claudin18.2 (mouse) cells (FIG. 4C) by flow cytometry.
Figure 4B:
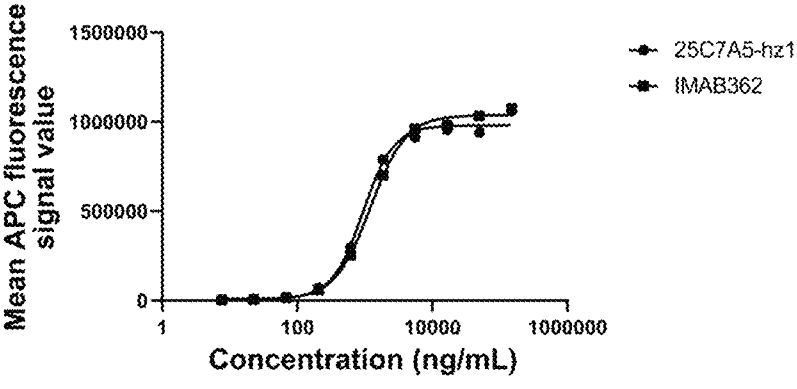
Figure 4C:
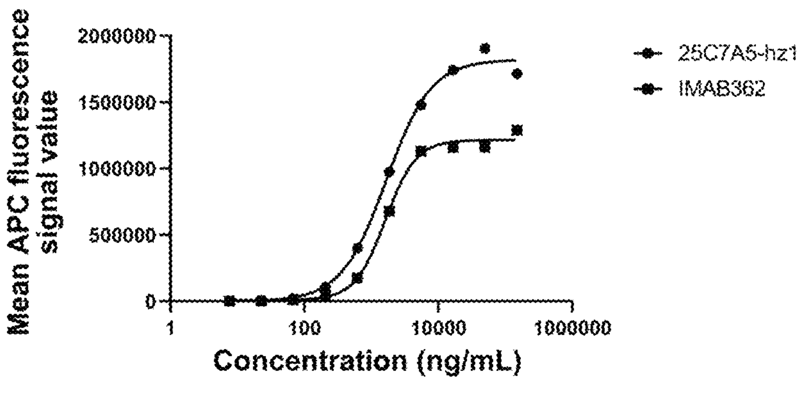

The experimental results are shown in FIGS. 4A-4C and Table 7, indicating that 2D3A11-HZ1, 25C7A5-HZ1, 25C7A5-HZ2, and IMAB362 all had high affinity for cynomolgus monkey Claudin18.2 (FIG. 4A); 25C7A5-HZ1 and IMAB362 also exhibited good species binding to rat Claudin18.2 (FIG. 4B) and mouse Claudin18.2 (FIG. 4C).

TABLE 7

Affinity results of anti-Claudin18.2 humanized antibodies by cell-based FACS

| Antibody name | Cell name | | |
|---|---|---|---|
| | HEK293T-Claudin18.2 (cynomolgus monkey) EC50 ng/mL | HEK293T-Claudin18.2 (mouse) EC50 ng/mL | HEK293T-Claudin18.2 (rat) EC50 ng/mL |
| 25C7A5-HZ1 | 239.8 | 940.7 | 1672 |
| 25C7A5-HZ2 | 213.3 | Not detected | Not detected |
| 2D3A11-HZ1 | 171.9 | Not detected | Not detected |
| IMAB362 | 242.7 | 1217 | 1624 |

Example 10. Evaluation of Specificity of Anti-Human Claudin18.2 Humanized Monoclonal Antibodies The specificity of the anti-human Claudin18.2 humanized monoclonal antibodies was determined by flow cytometry (FACS). The experimental procedures were as follows: HEK293T-Claudin18.1 (human) cells were digested, collected by centrifugation, washed three times with pre-cooled PBS, resuspended in 1% BSA (in PBS), and added to a 96-well pointed bottom plate at $3\times10^5$ cells/well. Each test antibody with a final concentration of 50 g/mL was added, and the mixture was incubated at 4° C. for 1 h. The cells were washed three times with pre-cooled PBS, and then 1 μL of a fluorescent secondary antibody (APC: Biolegend-410712 or PE: BioLegend-410708) was added to each well. The mixture was incubated at 4° C. for 0.5 h, and the cells were washed three times with pre-cooled PBS, then resuspended, and assayed on a flow cytometer. For reference, anti-human Claudin18.1 positive control antibodies (positive control antibody-1 and positive control antibody-2) were included in the experiment. Antibodies that exhibited significant binding to HEK293T-Claudin18.1 (human) cells in Example I-3 were selected as the positive control antibodies, and the antibody clones were numbered 13A6D2 (positive control antibody-1) and 15C12A2 (positive control antibody-2), respectively.

The experimental results are shown in Table 8, indicating that 2D3A11-HZ1, 2D3A11-HZ2, 25C7A5-HZ1, and 25C7A5-HZ2 did not recognize human Claudin18.1 non-specifically.

TABLE 8

Non-specific detection of anti-Claudin18.2 humanized antibodies

| Antibody name | Median APC fluorescence signal value | Mean APC fluorescence signal value | Positive rate (%) |
|---|---|---|---|
| 2D3A11-HZ1 | 233 | 281 | 0.69 |
| 2D3A11-HZ2 | 329 | 382 | 1 |
| Positive control antibody-1 | 726 | 979 | 16.2 |
| **Antibody name** | **Median PE fluorescence signal value** | **Mean PE fluorescence signal value** | **Positive rate (%)** |
| 25C7A5-HZ1 | 504 | 583 | 0.54 |
| 25C7A5-HZ2 | 471 | 559 | 0.55 |
| Positive control antibody-2 | 1055 | 1231 | 6.78 |
| Negative control antibody (NC) | 385 | 448 | 0.32 |

Example 11. Evaluation of Antibody-Dependent Cell-Mediated Cytotoxicity (ADCC) Activity of Anti-Human Claudin18.2 Humanized Monoclonal Antibodies ADCC activity of the anti-human Claudin18.2 humanized monoclonal antibodies was detected by a fluorescein reporter system. The experiment was carried out using a Rhinogen® Bio-Glory One-Step Firefly Luciferase Assay kit (Suzhou Rhino Bio, RA-GL04), following the manufacturer's instructions. The experimental procedures were as follows: HEK293T-Claudin18.2 (human) cells were digested, collected by centrifugation, resuspended in DMEM+1% FBS, and then plated at 50000 cells/well. Jurkat-NFAT-CD16a cells were collected by centrifugation and resuspended in 1640+1% FBS, and then plated at 100000 cells/well. Each test antibody subjected to gradient dilution was added, and the mixture was incubated at 37° C. for 5 h. 50 μL of a Bio-Glory One-Step luciferase substrate was added to each well, and readings were taken on a microplate reader (MD, SpectraMax i3x).

Figure 5:
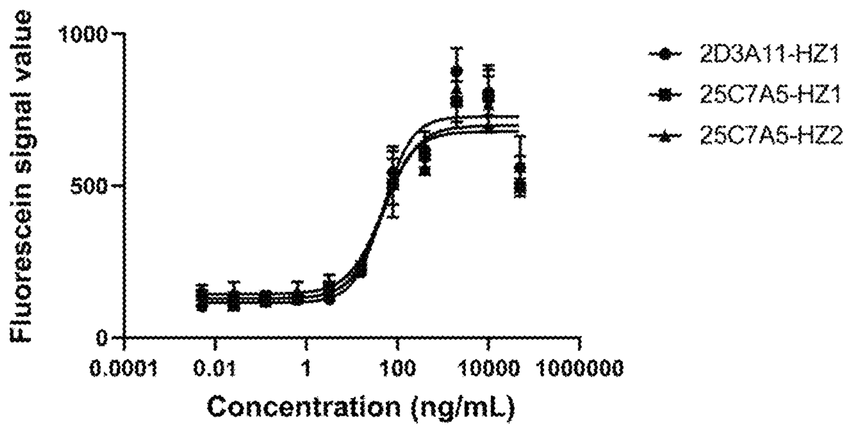
FIG. 5 shows the results of an ADCC killing activity assay for anti-human Claudin18.2 humanized antibodies against HEK293T-Claudin 18.2 (human) cells.

The experimental results are shown in FIG. 5, indicating that 2D3A11-HZ1, 25C7A5-HZ1, and 25C7A5-HZ2 all had strong ADCC activity, with $EC_{50}$ values of 47.91 ng/mL, 46.49 ng/mL and 48.75 ng/mL, respectively.

Example 12. Evaluation of Complement-Dependent Cytotoxicity (CDC) Activity of Anti-Human Claudin18.2 Humanized Monoclonal Antibodies CDC activity of the anti-human Claudin18.2 humanized monoclonal antibodies was detected by a guinea pig serum killing experiment. The experimental procedures were as follows: HEK293T-Claudin18.2 (human) cells were digested, collected by centrifugation, plated at 50000 cells/well, and incubated overnight. The supernatant was discarded, and 100 μL of each test antibody subjected to gradient dilution with DMEM+20% guinea pig serum (Beijing Bersee, BM361Y) was added to each well. The mixture was incubated at 37° C. for 5 h, and 20 μL of a CCK8 reagent (Suzhou Rhino Bio, QDY-003-D) was added to each well. The mixture was allowed to react for 1-4 h, and readings were taken at 450 nm on a microplate reader.

Figure 6:
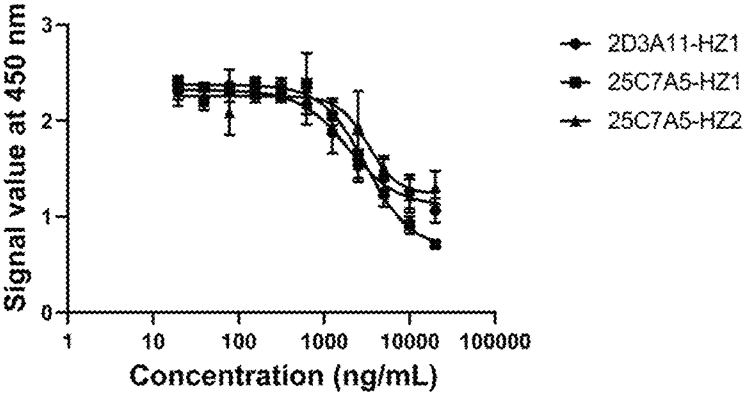
FIG. 6 shows the results of a CDC killing activity assay for anti-human Claudin18.2 humanized antibodies against HEK293T-Claudin 18.2 (human) cells.
Figure 7:
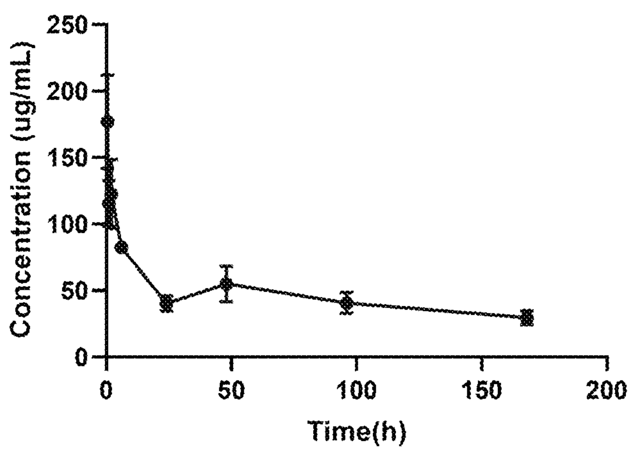
FIG. 7 shows an in-vivo pharmacokinetic assay for an anti-Claudin18.2 humanized antibody in rats.

The experimental results are shown in FIG. 6, indicating that 2D3A11-HZ1, 25C7A5-HZ1, and 25C7A5-HZ2 all had strong CDC activity, with $EC_{50}$ values of 1904 ng/mL, 3137 ng/mL and 3283 ng/mL, respectively.

Example 13. Evaluation of Endocytic Activity of Anti-Human Claudin18.2 Humanized Monoclonal Antibodies The endocytic activity of the anti-human Claudin18.2 humanized monoclonal antibodies was detected by flow cytometry (FACS). The experimental procedures were as follows: HEK293T-Claudin18.2 cells were digested, collected by centrifugation, incubated with each test antibody with a concentration of 10 g/mL at 4° C. for 1 h, washed 3 times with PBS, and resuspended in DMEM+10% FBS. The cell suspension was divided into 4 portions, which were then incubated at 37° C. for 0 h, 1 h, 2 h, and 4 h, respectively. The cells were washed three times with PBS, and then 1 μL of a fluorescent secondary antibody (Biolegend, 410712) was added. The mixture was incubated at 4° C. for 0.5 h. The cells were then washed three times with PBS, resuspended, and assayed on a machine. The endocytosis rate was calculated according to the following formula: endocytosis rate (%)=[1−(average fluorescence value of test sample at the time point−average fluorescence value of negative control sample at the time point)/(average fluorescence value of test sample at 0 h−average fluorescence value of negative control sample at 0 h)]×100. The negative antibody was an isotype control antibody.

The experimental results show that 25C7A5-HZ1 and 25C7A5-HZ2 both had endocytic activity, with both showing an endocytosis rate of 12% or greater at 4 h.

Example 14. Detection of Accelerated Stability of Anti-Human Claudin18.2 Humanized Antibody The accelerated stability of the anti-human Claudin18.2 humanized monoclonal antibody was detected by the following method: The test antibody was exchanged by ultrafiltration into PBS (pH=7.4) at a concentration of 4.7 mg/mL, sterilized by filtration, and left to stand at 37° C. for 0, 3, 7 and 14 days or subjected to 4 or 8 repeated freeze-thaw cycles at −80° C. Then, the SEC-HPLC purity and CE-SDS purity of the sample were detected. The antibody was examined for stability changes in the accelerated stability assay, using a control left to stand for 0 days at 37° C.

The SEC-HPLC detection method was as follows:

instrument: Waters Alliance e2695 HPLC;

chromatographic column: Thermo MabPac SEC-1, 5 m, 7.8×300 mm;

mobile phase: 61 mmol/L $Na_2HPO_4$, 39 mmol/L $NaH_2PO_4$, 200 mmol/L NaCl, 5% IPA;

instrument parameters: sample chamber temperature: 8° C.; column temperature: 30° C.; flow rate: 0.5 mL/min; sample injection volume: 20 g; detection wavelength: 280 nm; and isocratic run: 30 min.

The CE-SDS detection method was as follows: Each sample was diluted to 4 mg/mL with ultrapure water. 25 μL of the sample dilution was added to a centrifuge tube, and 75 μL of a premixed solution (SDS Sample buffer+iodoacetamide) was added. The mixture was well mixed, centrifuged at 10000 g for 1 min, and treated at 70° C. for 5 min. The sample was taken out, allowed to cool at room temperature, centrifuged at 10000 g for 1 min, well mixed, and transferred to a sample injection bottle.

The analysis was carried out using a PA800 plus capillary electrophoresis instrument from SCIEX, with the instrument parameters set as follows:

capillary tube: 30.2 cm×50 μm (bare tube), effective length: 20 cm;

capillary column temperature: 25° C., sample tray temperature: 15° C.;

detection wavelength: 220 nm; and collection frequency: 4 Hz.

The experimental results show that the 25C7A5 humanized antibody of the present invention had good stability under the accelerated conditions and repeated freeze-thaw cycles, with a SEC purity of 95% or greater, a CE-SDS non-reduced purity of 90% or greater, and a CE-SDS reduced purity of 95% or greater.

Example 15. In-vivo Pharmacokinetic Assay for Anti-Human Claudin18.2 Humanized Antibody in Rats The metabolism of the anti-human Claudin18.2 humanized antibody in vivo was examined as follows. The test samples, the humanized antibody and the IMAB362 antibody, were each administered to male rats (Chengdu Dossy) by injection at the tail vein at a dose of 10 mg/kg, with 3 rats in each group. Serum samples were collected 30 min, 1 h, 2 h, 6 h, 24 h, 48 h, 96 h, 168 h after the administration. The plasma drug concentration was determined by L929-Claudin18.2 cell-based ELISA (as described in Example 3). The results show that the 25C7A5 humanized antibody of the present invention had a comparable in-vivo half-life in rats to the reference antibody IMAB362.

Example II. Preparation and Characterization of Antibody-Drug Conjugates

Example 1. Preparation of Antibody-Drug Conjugates (ADCs)

Example 1.1. Synthesis of Intermediates Used in Synthesis of "Drug-Linker Compounds"

Example 1.1.1: Synthesis of(S)-7-ethyl-7-hydroxy-14-(3-hydroxypropyl)-10,13-dihydro-11H-[1,3]dioxolo[4,5-g]pyrano[3',4':6,7]indolizino[1,2-b]quinoline-8,11(7H)-dione (A1)

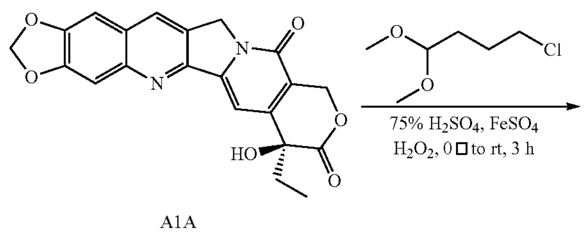

A1A

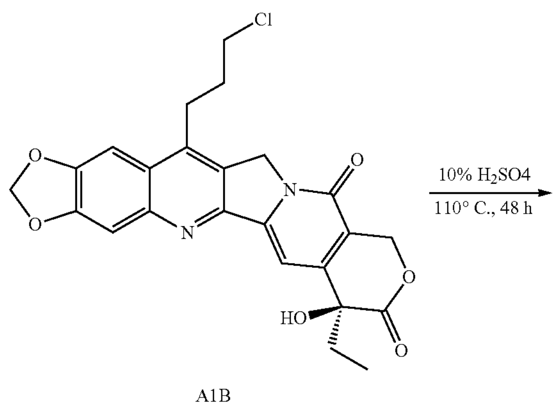

A1B

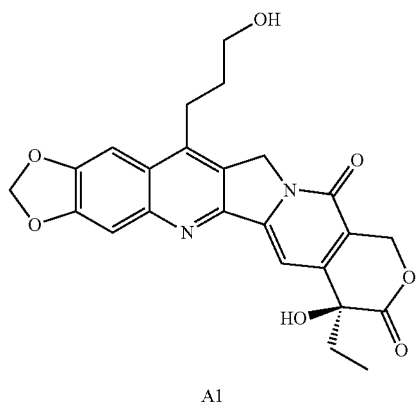

A1

Step 1: synthesis of(S)-7-ethyl-7-hydroxy-14-(3-chloropropyl)-10,13-dihydro-11H-[1,3]dioxolo[4,5-g]pyrano[3',4':6,7]indolizino[1,2-b]quinoline-8,11(7H)-dione (A1B)

To a solution of compound (S)-7-ethyl-7-hydroxy-10,13-dihydro-11H-[1,3]dioxolo[4,5-g]pyrano[3',4':6,7]indolizino[1,2-b]quinoline-8,11(7H)-dione (A1A, Cas No. 151636-76-9, 500 mg) in 75% sulfuric acid (5 mL) were added ferrous sulfate heptahydrate (570 mg of ferrous sulfate heptahydrate dissolved in 1 mL of water) and 4,4-dimethoxychlorobutane (3.89 g) in an ice bath, and the reaction solution was stirred for three minutes, followed by the dropwise addition of hydrogen peroxide (29%, 2.5 mL). The reaction solution was stirred at 0° C. for reaction for 5 min, then heated to room temperature, and stirred for reaction for another 3 h. The reaction solution was diluted with water (50 mL) and extracted with ethyl acetate (80 mL×2). The organic phase was washed with saturated brine, dried over anhydrous sodium sulfate, and concentrated to give a crude product. The crude product was further purified using a C18 column (acetonitrile/0.05% aqueous formic acid solution: 5%-60%) to give the target compound A1B (yellow solid, 400 mg, yield: 67%).

LCMS (ESI) $[M+H]^+$: 468.9;

$^1H$ NMR (400 MHz, DMSO-d6) δ 7.65 (s, 1H), 7.51 (s, 1H), 7.24 (s, 1H), 6.50 (s, 1H), 6.30 (s, 2H), 5.42 (s, 2H), 5.26 (s, 2H), 3.81 (d, J=5.9 Hz, 2H), 3.22 (s, 2H), 1.98 (d, J=6.7 Hz, 4H), 0.88 (t, J=7.2 Hz, 3H).

Step 2: synthesis of (S)-7-ethyl-7-hydroxy-14-(3-hydroxypropyl)-10,13-dihydro-11H-[1,3]dioxolo[4,5-g]pyrano[3',4':6,7]indolizino[1,2-b]quinoline-8,11(7H)-dione (A1)

Compound (S)-7-ethyl-7-hydroxy-14-(3-chloropropyl)-10,13-dihydro-11H-[1,3]dioxolo[4,5-g]pyrano[3',4':6,7]indolizino[1,2-b]quinoline-8,11(7H)-dione (100 mg, 0.213 mmol) was dissolved in a 10% sulfuric acid (5 mL) solution, and the reaction solution was allowed to react at 110° C. for 48 h. To the reaction solution was added a saturated sodium bicarbonate solution (30 mL), and the resulting mixture was extracted with dichloromethane (10 mL×5), dried over anhydrous sodium sulfate, filtered under vacuum, and concentrated under reduced pressure to give a crude product. The crude product was purified by preparative high performance liquid chromatography (acetonitrile/water containing 0.05% formic acid) to give (S)-7-ethyl-7-hydroxy-14-(3-hydroxypropyl)-10,13-dihydro-1H-[1,3]dioxolo[4,5-g]pyrano[3',4':6,7]indolizino[1,2-b]quinoline-8,11(7H)-dione (A1, 1.78 mg).

LCMS (ESI) $[M+H]^+$: 451.0;

$^1H$ NMR (400 MHz, DMSO-d6) δ 7.63 (s, 1H), 7.50 (s, 1H), 7.24 (s, 1H), 6.48 (s, 1H), 6.28 (s, 2H), 5.47-5.37 (m, 2H), 5.32-5.19 (m, 2H), 3.51-3.46 (m, 2H), 3.17-3.13 (m, 2H), 1.92-1.76 (m, 4H), 0.90-0.84 (m, 3H).

Example 1.1.2: Synthesis of(S)-2-amino-N-((3-(7-ethyl-7-hydroxy-8,11-dioxo-7,8,11,13-tetrahydro-10H-[1,3]dioxolo[4,5-g]pyrano[3',4':6,7]indolizino[1,2-b]quinolin-14-yl)propoxy)methyl)acetamide (B1)
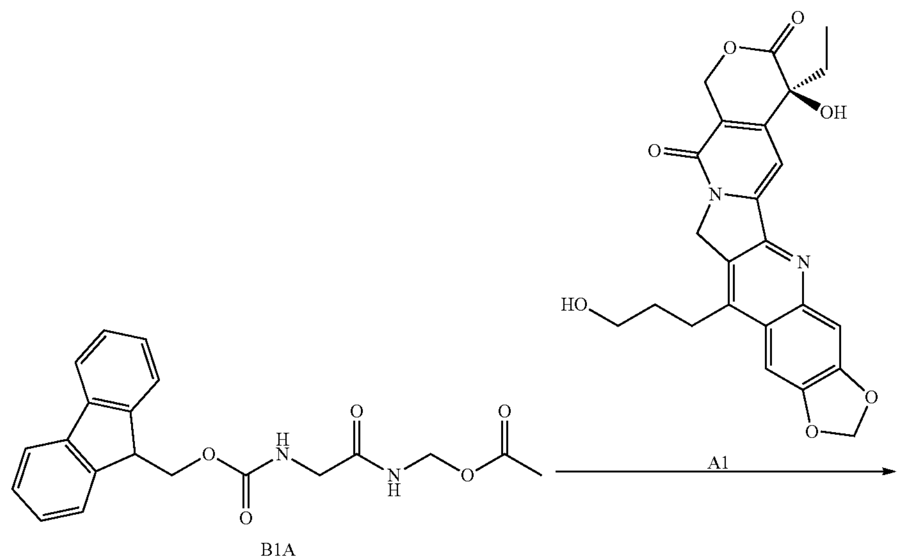
B1A
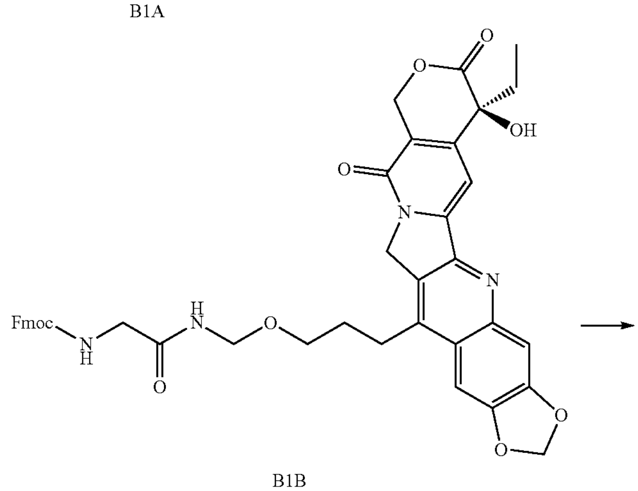
B1B
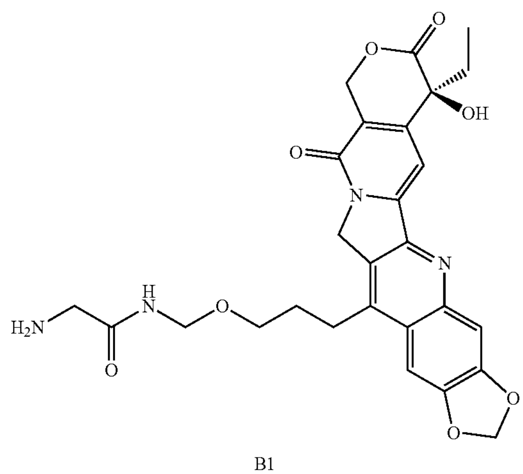
B1

Step 1: Compound (B1A) (Cas No. 1599440-06-8, 368 mg), compound (A1) (440 mg), and pyridinium p-toluenesulfonate (PPTS) (25 mg) were refluxed in dichloromethane (20 mL) for 20 h, then washed sequentially with an aqueous sodium bicarbonate solution and an aqueous hydrochloric acid solution. The mixture was concentrated under reduced pressure to remove the organic solvent to give a crude product. The crude product was purified by column chromatography (dichloromethane:methanol=10/1) to give the target compound B1B (240 mg).

LCMS (ESI) $[M+H]^+$: 759.5.

Step 2: B1B (240 mg) was dissolved in DMF (5 mL), piperidine (1 mL) was added, and the mixture was stirred for 20 min. The reaction solution was concentrated under reduced pressure to remove low boiling components, and the residue was used directly in the next step. A small amount of the crude product was purified by reverse-phase chromatography (acetonitrile/0.05% aqueous FA solution: 5% to 50%) to give the target compound B1.

ESI-MS (m/z): 537.4 $[M+H]^+$;

$^1$H NMR (400 MHz, DMSO-d6) δ 9.13 (t, 1H), 8.04 (br, 2H), 7.58 (s, 1H), 7.51 (s, 1H), 7.25 (s, 1H), 6.29 (s, 2H), 5.43 (S, 2H), 5.21 (s, 2H), 4.65 (d, 2H), 3.63 (m, 2H), 3.53 (m, 2H), 3.11 (m, 2H), 1.87 (m, 4H), 0.88 (t, 3H).

Example 1.1.3: $N^6$,$N^6$-Dimethyl-$N^2$-((6-(2-(methylsulfonyl)pyrimidin-5-yl)hex-5-ynoyl)-L-valyl)-L-lysine (C1)

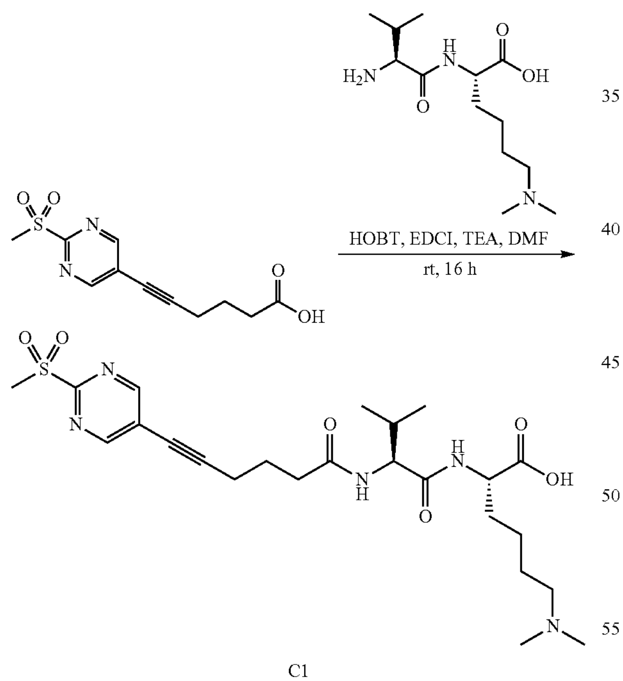

C1

6-(2-(Methylsulfonyl)pyrimidin-5-yl)hex-5-ynoic acid (268 mg, Cas No. 2356229-58-6), compound C1A (328 mg), and triethylamine (322 mg) were dissolved in N,N-dimethylformamide (5 mL). 1-Hydroxybenzotriazole (HOBT, 162 mg) and 1-(3-dimethylaminopropyl)-3-ethylcarbodiimide hydrochloride (EDCI, 229 mg) were then added, and the reaction solution was stirred at room temperature for 16 h and then directly purified by C18 reverse-phase column chromatography (acetonitrile and 0.05% aqueous formic acid solution system) to give the target compound $N^6$,$N^6$-dimethyl-$N^2$-((6-(2-(methylsulfonyl)pyrimidin-5-yl)hex-5-ynoyl)-L-valyl)-L-lysine (C1, white solid, 327 mg).

LCMS (ESI) $[M+H]^+$: 524.4.

$^1$H NMR (400 MHz) δ 9.13 (s, 2H), 7.95 (t, J=8.8 Hz, 2H), 4.21 (dd, J=8.8, 6.9 Hz, 1H), 4.08-4.03 (m, 1H), 3.41 (s, 3H), 2.55 (t, J=7.0 Hz, 2H), 2.42-2.32 (m, 4H), 2.27 (s, 6H), 1.98 (dd, J=13.6, 6.8 Hz, 1H), 1.86-1.77 (m, 2H), 1.74-1.55 (m, 2H), 1.47-1.37 (m, 2H), 1.31-1.23 (m, 2H), 0.85 (dd, J=12.8, 6.8 Hz, 6H).

Example 1.1.4: $N^6$,$N^6$-Diethyl-$N^2$-((6-(2-(methylsulfonyl)pyrimidin-5-yl)hex-5-ynoyl)-L-valyl)-L-lysine (C2)

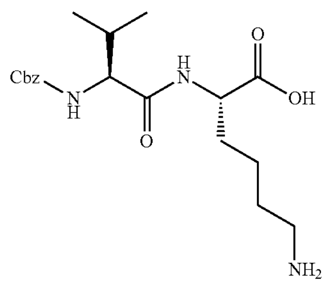

C2A

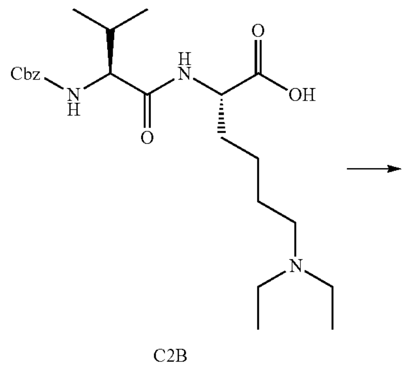

C2B

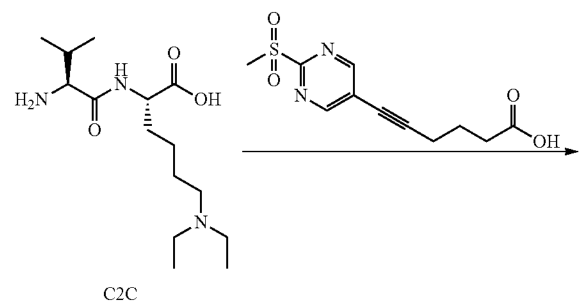

C2C

-continued

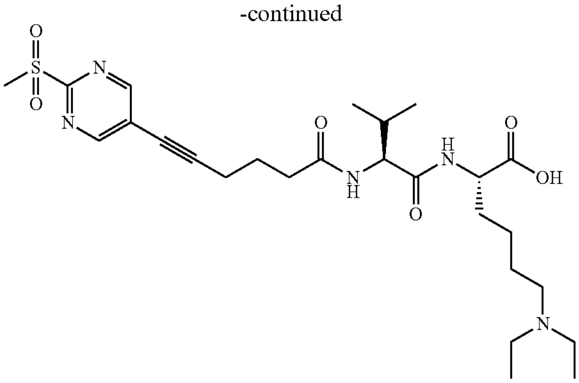

C2

Step 1:

Compound C2A (5.0 g, 12.05 mmol, Cas No. 1872-06-8) was dissolved in dichloromethane (100 mL), and acetaldehyde (3.2 g, 72.3 mmol) was added to the reaction solution. The mixture was stirred at room temperature for 10 min. Sodium triacetoxyborohydride (12.8 g, 60.25 mmol) was added to the reaction solution, and the resulting mixture was stirred at room temperature for reaction for 1 h. After the reaction was completed as detected by LCMS, to the reaction solution was added a saturated aqueous ammonium chloride solution, and the resulting mixture was stirred for one hour, concentrated by rotary evaporation, and filtered. The filtrate was purified by C18 reverse-phase column chromatography (acetonitrile:0.05% aqueous formic acid solution: 5% to 55%) to give the target compound C2B (4.57 g, yield: 82.0%) as a white solid.

LCMS (ESI) $[M+H]^+$=436.4;

$^1$H NMR (400 MHz, DMSO-d6) δ 7.70 (d, J=7.0 Hz, 1H), 7.41 (d, J=9.0 Hz, 1H), 7.38-7.26 (m, 5H), 5.08-4.99 (m, 2H), 4.00 (dd, J=12.6, 6.5 Hz, 1H), 3.86 (dd, J=8.6, 6.8 Hz, 1H), 2.74 (dd, J=14.0, 6.9 Hz, 4H), 2.64-2.54 (m, 2H), 2.05-1.94 (m, 1H), 1.72-1.52 (m, 2H), 1.52-1.38 (m, 2H), 1.38-1.18 (m, 2H), 1.04 (t, J=7.1 Hz, 6H), 0.87-0.81 (m, 6H).

Step 2:

Compound C2B (1.6 g, 3.68 mmol) was dissolved in methanol (80 mL) at room temperature, and then Pd/C (0.16 g) was added to the reaction solution. The resulting mixture was stirred at room temperature under hydrogen atmosphere for reaction for 12 h. After the reaction was completed as detected by LCMS, the reaction solution was filtered, and the filtrate was concentrated under reduced pressure to give the target compound C2C (900 mg, yield: 82%) as a creamy-white solid.

$^1$H NMR (400 MHz, DMSO-d6) δ 8.04 (br s, 1H), 4.02-3.99 (m, 1H), 3.10 (d, J=4.5 Hz, 1H), 2.65 (q, J=7.1 Hz, 4H), 2.55-2.51 (m, 2H), 2.06-1.93 (m, 1H), 1.73-1.54 (m, 2H), 1.47-1.38 (m, 2H), 1.30-1.21 (m, 2H), 1.01 (t, J=7.1 Hz, 6H), 0.89 (d, J=6.9 Hz, 3H), 0.79 (d, J=6.8 Hz, 3H).

Step 3:

Compound 6-(2-(methylsulfonyl)pyrimidin-5-yl)hex-5-ynoic acid (268 mg, 1 mmol) was dissolved in DMF (8 mL), and HATU (380 mg, 1 mmol) and triethylamine (322 mg, 2.5 mmol) were added sequentially. The resulting mixture was stirred at room temperature for 20 min, and then compound C2C (301 mg, 1 mmol) was added. The mixture was stirred at room temperature for another 30 min. After the reaction was completed as detected by LCMS, the reaction solution was directly purified by C18 reverse-phase column chromatography (acetonitrile and 0.05% aqueous formic acid solution system) to give the target compound C2 (280 mg, yield: 51%) as a white solid.

LCMS (ESI) $[M+H]^+$=552.3;

$^1$H NMR (400 MHz, DMSO-d6) δ 9.13 (s, 2H), 7.95 (d, J=8.9 Hz, 1H), 7.86 (d, J=7.2 Hz, 1H), 4.18 (dd, J=8.8, 6.8 Hz, 1H), 4.02 (dd, J=12.8, 7.2 Hz, 1H), 3.41 (s, 3H), 2.74-2.69 (m, 4H), 2.62-2.52 (m, 4H), 2.44-2.29 (m, 2H), 2.04-1.94 (m, 1H), 1.86-1.77 (m, 2H), 1.72-1.54 (m, 2H), 1.51-1.39 (m, 2H), 1.33-1.23 (m, 2H), 1.02 (t, J=7.2 Hz, 6H), 0.87-0.82 (m, 6H).

Example 1.1.5: $N^6$,$N^6$-Di-n-propyl-$N^2$-((6-(2-(methylsulfonyl)pyrimidin-5-yl)hex-5-ynoyl)-L-valyl)-L-lysine (C3)

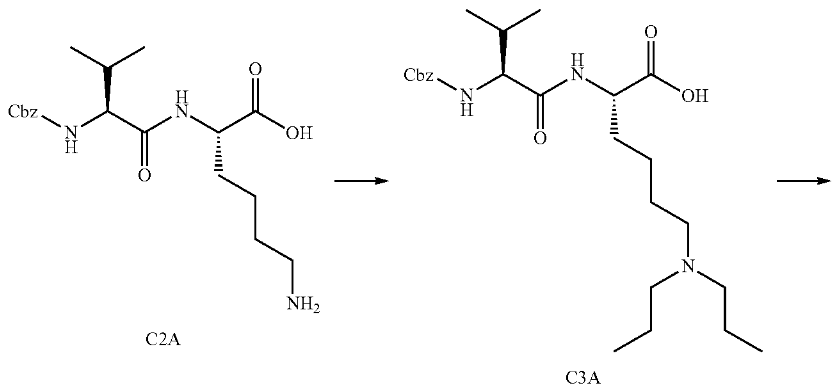

C2A C3A

-continued

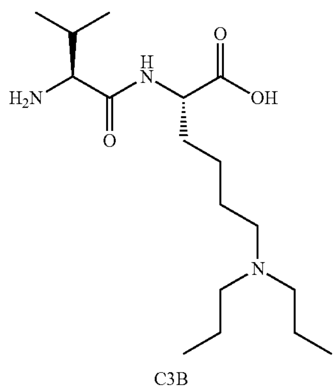

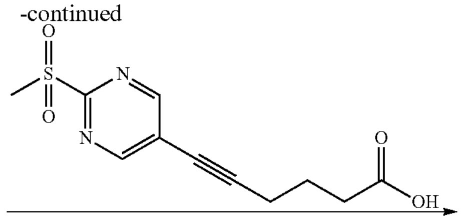

C3B

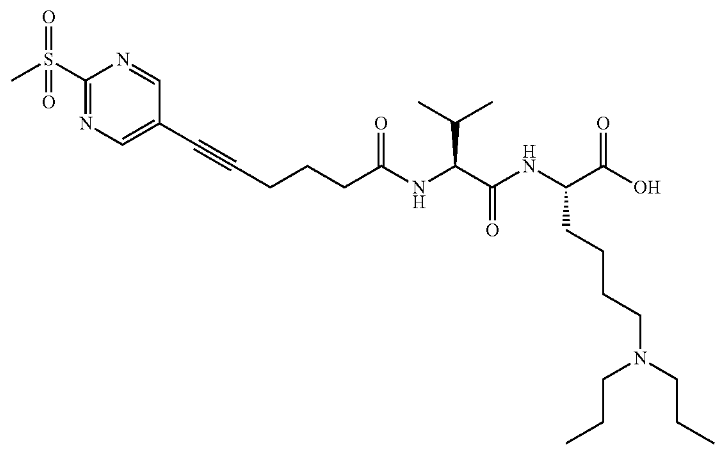

C3

Step 1:

Compound C2A (5.0 g, 12 mmol) was dissolved in dichloromethane (100 mL), and n-propionaldehyde (4.2 g, 72.3 mmol) was added to the reaction solution. The resulting mixture was stirred at room temperature for reaction for 10 min. Sodium triacetoxyborohydride (12.8 g, 60.25 mmol) was then added to the reaction solution, and the resulting mixture was stirred at room temperature for reaction for 1 h. After the reaction was completed as detected by LCMS, to the reaction solution was added a saturated aqueous ammonium chloride solution, and the resulting mixture was stirred for one hour, concentrated by rotary evaporation, and filtered. The filtrate was purified by C18 reverse-phase column chromatography (acetonitrile:0.05% aqueous formic acid solution: 5% to 55%) to give the target compound C3A (4.57 g, yield: 82.0%) as a white solid.

LCMS (ESI) $[M+H]^+$=464.0;

$^1$H NMR (400 MHz, DMSO-d6) δ 7.81 (d, J=7.3 Hz, 1H), 7.38-7.28 (m, 5H), 5.04 (d, J=1.7 Hz, 2H), 4.12-4.02 (m, 1H), 3.94-3.82 (m, 1H), 2.65-2.52 (m, 6H), 2.06-1.94 (m, 1H), 1.76-1.64 (m, 1H), 1.64-1.53 (m, 1H), 1.52-1.40 (m, 6H), 1.34-1.18 (m, 2H), 0.92-0.80 (m, 12H).

Step 2:

Compound C3A (2.0 g, 4.32 mmol) was dissolved in methanol (80 mL) at room temperature, and then Pd/C (0.16 g) was added to the reaction solution. The resulting mixture was stirred at room temperature under hydrogen atmosphere for reaction for 12 h. After the reaction was completed as detected by LCMS, the reaction solution was filtered, and the filtrate was concentrated under reduced pressure to give the target compound C3B (1.2 g, yield: 85.5%) as a white solid.

Step 3:

compound 6-(2-(methylsulfonyl)pyrimidin-5-yl)hex-5-ynoic acid (100 mg, 0.373 mmol) was dissolved in N,N-dimethylformamide (1 mL), and then HATU (142 mg, 0.373 mmol) and N,N-diisopropylethylamine (120 mg, 0.93 mmol) were added. The system was stirred for 30 min, and then compound C3B (122 mg, 0.371 mmol) was added. The reaction solution was stirred at room temperature for 1 h. After the reaction was completed as detected by LCMS, the reaction solution was directly purified by C18 reverse-phase column chromatography (acetonitrile and 0.05% aqueous formic acid solution system) to give the target compound $N^6$,$N^6$-di-n-propyl-$N^2$-((6-(2-(methylsulfonyl)pyrimidin-5-yl)hex-5-ynoyl)-L-valyl)-L-lysine (C3, 50 mg, yield: 28%) as a light yellow solid.

LCMS (ESI) $[M+H]^+$=580.0;

$^1$H NMR (400 MHz, DMSO-d6) δ 8.24 (s, 2H), 7.98-7.93 (m, 2H), 4.24-4.16 (m, 1H), 4.10 (d, J=5.2 Hz, 1H), 3.41 (s, 3H), 2.79-2.64 (m, 6H), 2.55 (t, J=7.1 Hz, 2H), 2.45-2.26 (m, 2H), 2.06-1.91 (m, 1H), 1.89-1.78 (m, 2H), 1.76-1.66 (m, 1H), 1.64-1.57 (m, 1H), 1.57-1.42 (m, 6H), 1.37-1.24 (m, 2H), 0.93-0.78 (m, 12H).

Example 1.2. Synthesis of Drug-Linker Compounds

Example 1.2.1: N-((11S,14S)-11-(4-(Dipropylamino)butyl)-1-((S)-7-ethyl-7-hydroxy-8,11-dioxo-7,8,11,13-tetrahydro-10H-[1,3]dioxolo[4,5-g]pyrano[3',4':6,7]indolizino[1,2-b]quinolin-14-yl)-15-methyl-7,10,13-trioxo-4-oxa-6,9,12-triazahexadecan-14-yl)-6-(2-(methylsulfonyl)pyrimidin-5-yl)hex-5-ynamide (DL-01)

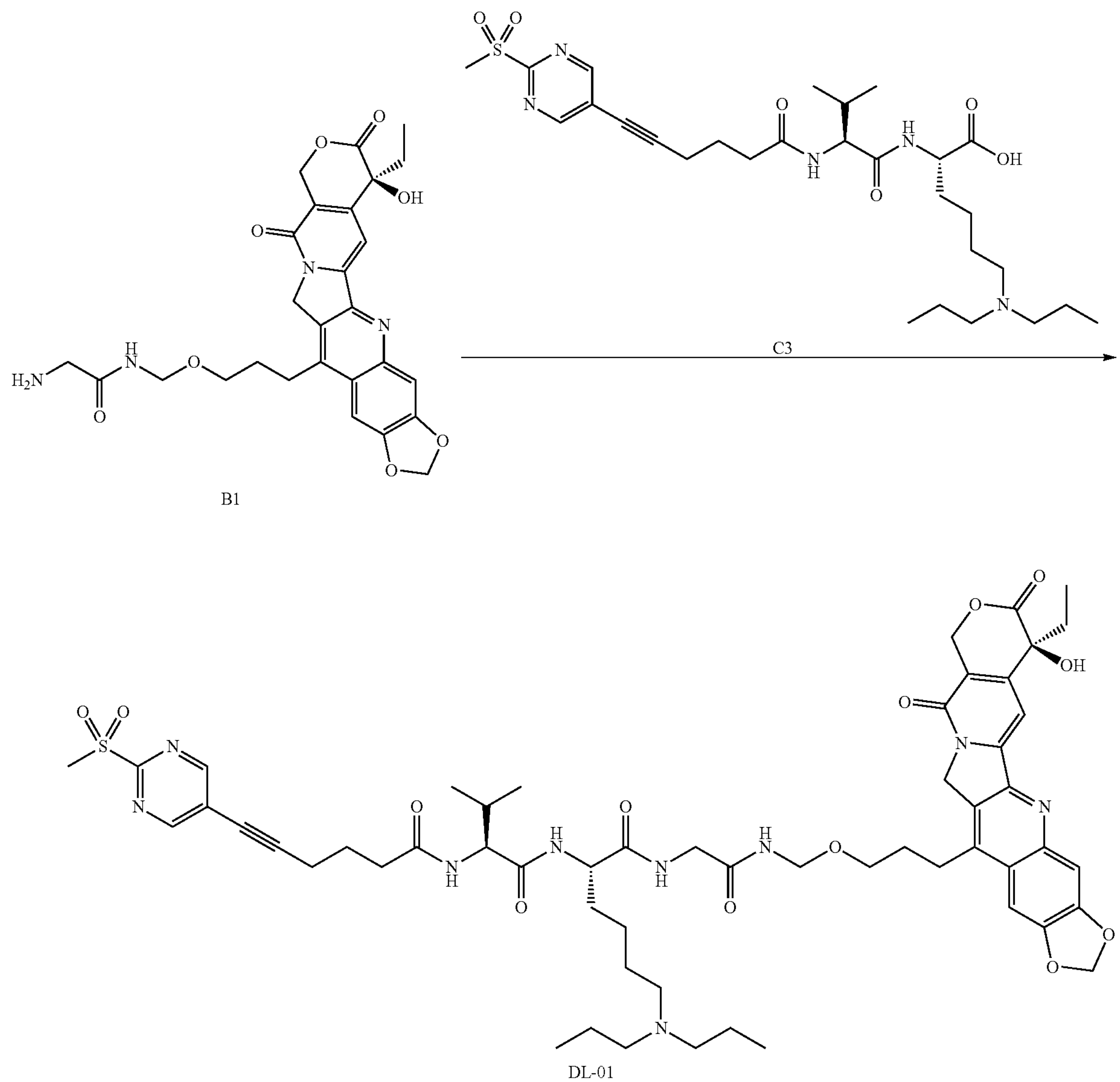 [SMILES: CC[C@@]1(O)C(=O)OCc2c1cc1n(c2=O)Cc2c-1nc1cc3c(cc1c2CCCOCNC(=O)CN)OCO3 ; CCCN(CCC)CCCC[C@H](NC(=O)[C@@H](NC(=O)CCCC#Cc1cnc(S(C)(=O)=O)nc1)C(C)C)C(=O)O ; "C3" ; "B1" ; CCCN(CCC)CCCC[C@H](NC(=O)[C@@H](NC(=O)CCCC#Cc1cnc(S(C)(=O)=O)nc1)C(C)C)C(=O)NCC(=O)NCOCCCc1c2c(nc3cc4c(cc13)OCO4)-c1cc3c(c(=O)n1C2)COC(=O)[C@]3(O)CC]

B1

DL-01

Compound C3 (43 mg, 0.074 mmol) and compound B1 (40 mg, 0.075 mmol) were dissolved in N,N-dimethylformamide (1 mL), and then HBTU (28 mg, 0.075 mmol) and NN-diisopropylethylamine (24 mg, 0.187 mmol) were added sequentially. The reaction solution was stirred at room temperature for 1 h. After the reaction was completed as detected by LCMS, the reaction solution was directly purified by preparative chromatography (0.01% aqueous trifluoroacetic acid solution, acetonitrile) to give the target compound (DL-01, 8.5 mg, yield: 10%) as a yellow solid.

LCMS (ESI) $[M+H]^+$=1098.6;

$^1$H NMR (400 MHz, DMSO-d6) δ 9.10 (s, 2H), 9.03 (s, 1H), 8.64 (t, J=6.4 Hz, 1H), 8.19 (t, J=5.9 Hz, 1H), 8.08 (d, J=7.4 Hz, 1H), 7.92 (d, J=8.5 Hz, 1H), 7.59 (s, 1H), 7.51 (s, 1H), 7.24 (s, 1H), 6.49 (s, 1H), 6.29 (s, 2H), 5.42 (s, 2H), 5.24 (s, 2H), 4.66-4.52 (m, 2H), 4.31-4.21 (m, 1H), 4.19-4.10 (m, 1H), 3.74 (d, J=5.5 Hz, 2H), 3.49-3.48 (m, 2H), 3.40 (s, 3H), 3.15-3.06 (m, 2H), 3.02-2.95 (m, 6H), 2.59-2.52 (m, 3H), 2.41-2.29 (m, 2H), 2.05-1.90 (m, 2H), 1.91-1.77 (m, 6H), 1.63-1.57 (m, 6H), 1.31-1.29 (m, 2H), 0.92-0.80 (m, 15H).

Example 1.2.2: N-((11S,14S)-11-(4-(Diethylamino)butyl)-1-((S)-7-ethyl-7-hydroxy-8,11-dioxo-7,8,11,13-tetrahydro-10H-[1,3]dioxolo[4,5-g]pyrano[3',4':6,7]indolizino[1,2-b]quinolin-14-yl)-15-methyl-7,10,13-trioxo-4-oxa-6,9,12-triazahexadecan-14-yl)-6-(2-(methylsulfonyl)pyrimidin-5-yl)hex-5-ynamide (DL-02)

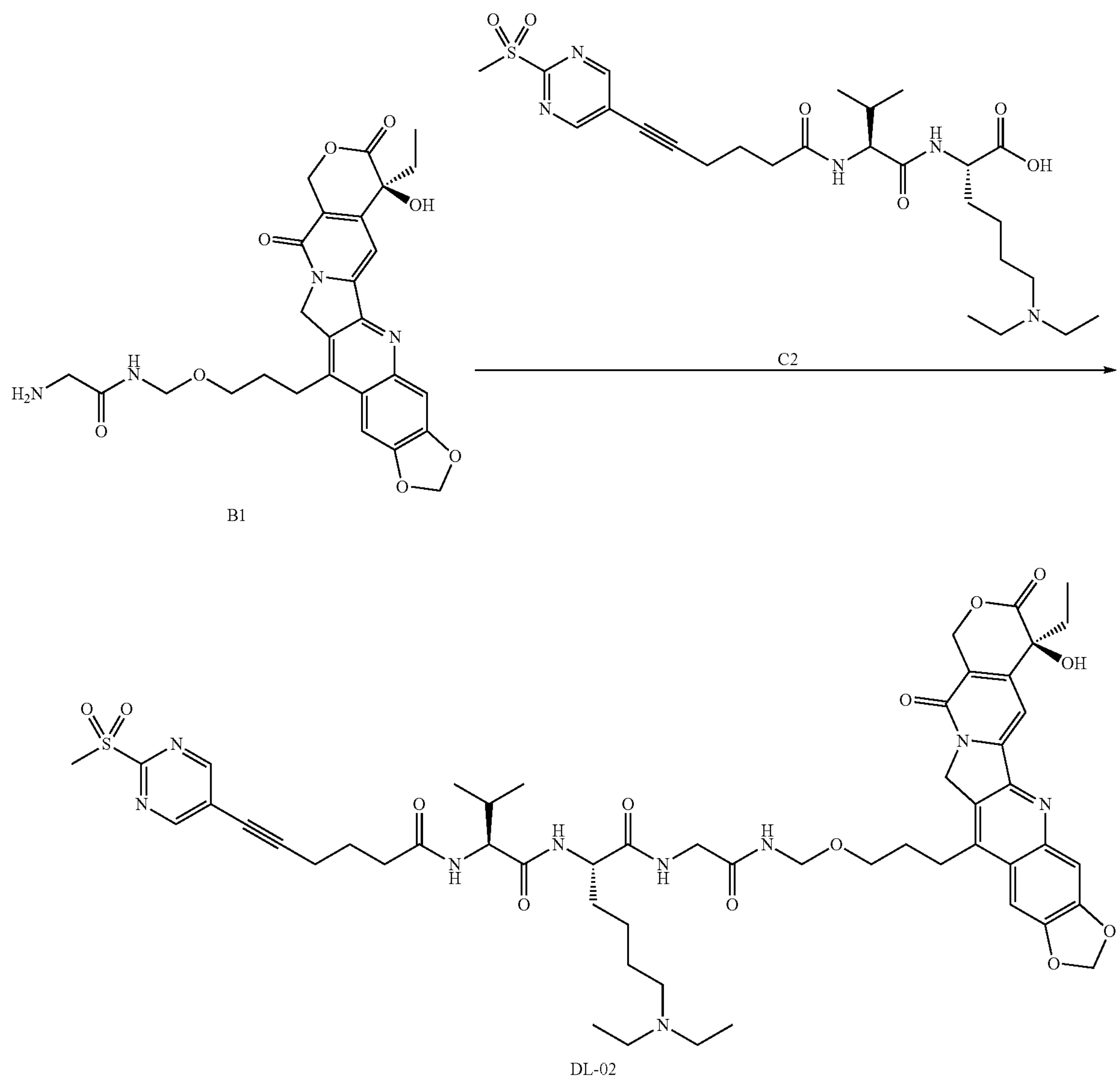 [SMILES: CC[C@@]1(O)C(=O)OCc2c1cc1n(c2=O)Cc2c-1nc1cc3c(cc1c2CCCOCNC(=O)CN)OCO3 ; CCN(CC)CCCC[C@H](NC(=O)[C@@H](NC(=O)CCCC#Cc1cnc(S(C)(=O)=O)nc1)C(C)C)C(=O)O ; "C2" ; "B1" ; CCN(CC)CCCC[C@H](NC(=O)[C@@H](NC(=O)CCCC#Cc1cnc(S(C)(=O)=O)nc1)C(C)C)C(=O)NCC(=O)NCOCCCc1c2c(nc3cc4c(cc13)OCO4)-c1cc3c(c(=O)n1C2)COC(=O)[C@]3(O)CC]

B1

DL-02

Compound C2 (40 mg, 0.075 mmol) and compound B1 (41 mg, 0.075 mmol) were dissolved in DMF (1 mL), and then HOBt (15.2 mg, 0.113 mmol) and 1-(3-dimethylaminopropyl)-3-ethylcarbodiimide hydrochloride (21.5 mg, 0.113 mmol) were added, followed by the addition of triethylamine (23 mg, 0.225 mmol). After the addition, the reaction solution was stirred at room temperature for 16 h. After the reaction was completed as detected by LCMS, the reaction solution was concentrated to give a crude product. The crude product was purified by preparative chromatography (0.01% aqueous TFA solution, acetonitrile) to give the target compound (DL-02, 16 mg, yield: 20%) as a yellow solid.

LCMS (ESI) $[M+H]^+$=1070.6;

$^1$H NMR (400 MHz, DMSO-d6) δ 9.13-9.08 (m, 2H), 9.01 (s, 1H), 8.64 (t, J=6.5 Hz, 1H), 8.20 (t, J=5.7 Hz, 1H), 8.09 (d, J=7.4 Hz, 1H), 7.92 (d, J=8.4 Hz, 1H), 7.59 (s, 1H), 7.51 (s, 1H), 7.24 (s, 1H), 6.50 (s, 1H), 6.29 (s, 2H), 5.43 (s, 2H), 5.24 (s, 2H), 4.65-4.53 (m, 2H), 4.26 (d, J=6.5 Hz, 1H), 4.20-4.10 (m, 1H), 3.74 (d, J=5.5 Hz, 2H), 3.50 (t, J=5.8 Hz, 2H), 3.41 (s, 3H), 3.14-3.07 (m, 6H), 2.98 (s, 2H), 2.55 (d, J=7.3 Hz, 2H), 2.41-2.29 (m, 2H), 2.03-1.89 (m, 2H), 1.89-1.77 (m, 7H), 1.61-1.56 (m, 2H), 1.32 (s, 2H), 1.16 (t, J=7.2 Hz, 6H), 0.91-0.78 (m, 9H).

Example 1.2.3: N-((11S,14S)-11-(4-(Dimethylamino)butyl)-1-((S)-7-ethyl-7-hydroxy-8,11-dioxo-7,8,11,13-tetrahydro-10H-[1,3]dioxolo[4,5-g]pyrano[3',4':6,7]indolizino[1,2-b]quinolin-14-yl)-15-methyl-7,10,13-trioxo-4-oxa-6,9,12-triazahexadecan-14-yl)-6-(2-(methylsulfonyl)pyrimidin-5-yl)hex-5-ynamide (DL-03)

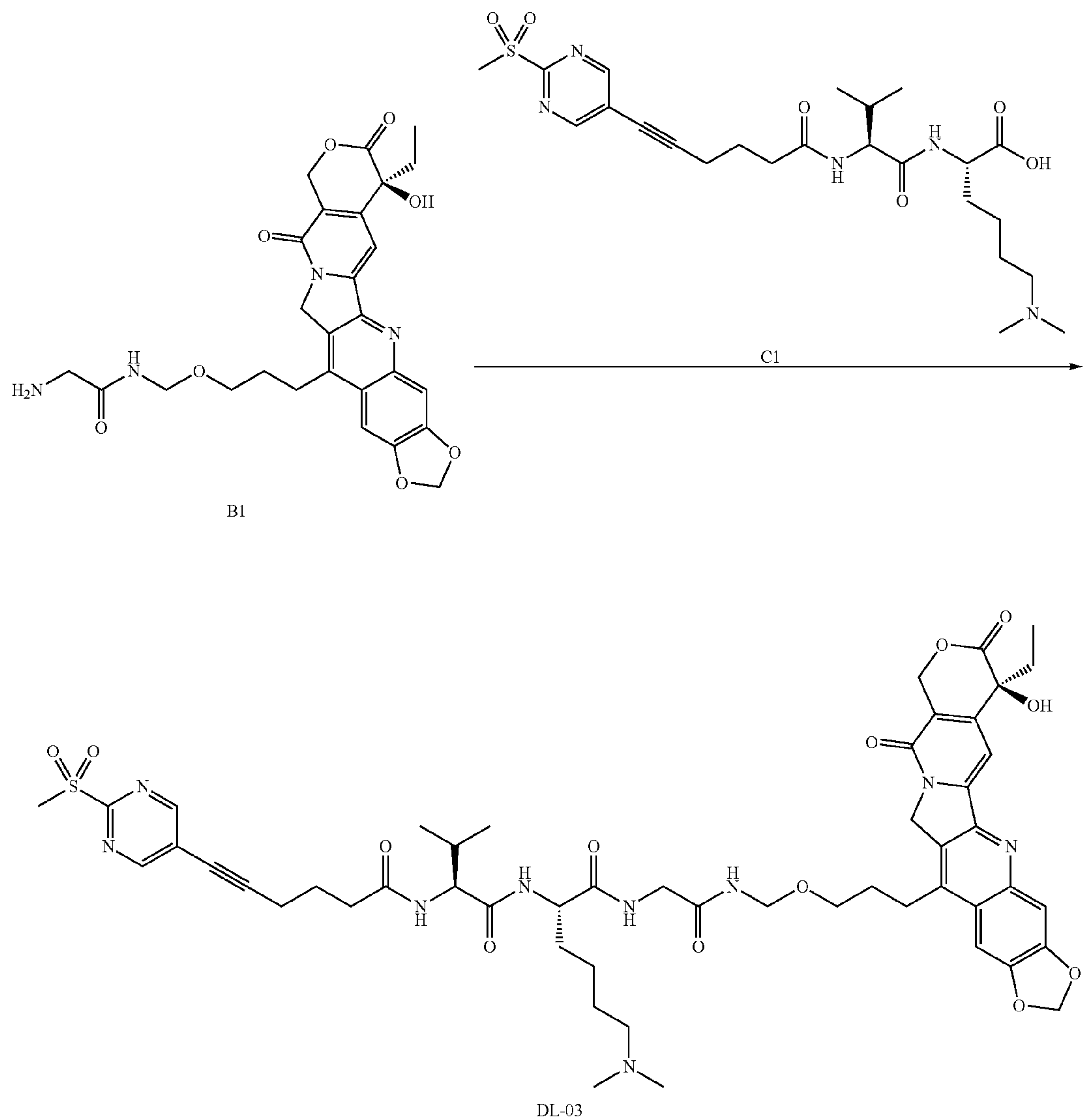

B1

DL-03

Compound B1 (100 mg, 0.186 mmol) and compound $N^6$,$N^6$-dimethyl-$N^2$-((6-(2-(methylsulfonyl)pyrimidin-5-yl)hex-5-ynoyl)-L-valyl)-L-lysine (C1, 100 mg, 0.191 mmol) were dissolved in DMF (2 mL). 1-Hydroxybenzotriazole (38 mg, 0.280 mmol) and 1-(3-dimethylaminopropyl)-3-ethylcarbodiimide hydrochloride (53 mg, 0.280 mmol) were added, followed by the addition of triethylamine (56 mg, 0.559 mmol). After the addition, the reaction solution was stirred at room temperature for 16 h. After the reaction was completed as detected by LCMS, the reaction solution was directly purified by preparative chromatography (0.01% aqueous TFA solution, acetonitrile) to give the target compound (DL-03, 20 mg, yield: 10%) as a yellow solid.

LCMS (ESI) $[M+H]^+$=1042.5;

$^1$H NMR (400 MHz, DMSO-d6) δ 9.28 (s, 1H, TFA), 9.10 (s, 2H), 8.64 (br s, 1H), 8.19 (br s, 1H), 8.09 (d, J=6.4 Hz, 1H), 7.92 (d, J=7.8 Hz, 1H), 7.59 (s, 1H), 7.51 (s, 1H), 7.24 (s, 1H), 6.50 (s, 1H), 6.29 (s, 2H), 5.43 (s, 2H), 5.24 (s, 2H), 4.67-4.52 (m, 2H), 4.30-4.10 (m, 2H), 3.74 (br s, 2H), 3.50 (br s, 2H), 3.41 (s, 3H), 3.17-3.07 (m, 2H), 3.04-2.91 (m, 2H), 2.75 (s, 6H), 2.46-2.24 (m, 3H), 2.04-1.66 (m, 9H), 1.63-1.46 (m, 3H), 1.32-1.29 (m, 2H), 0.87-0.82 (m, 9H).

Example 1.3. Preparation of Anti-CLDN18.2 Antibody-Drug Conjugates

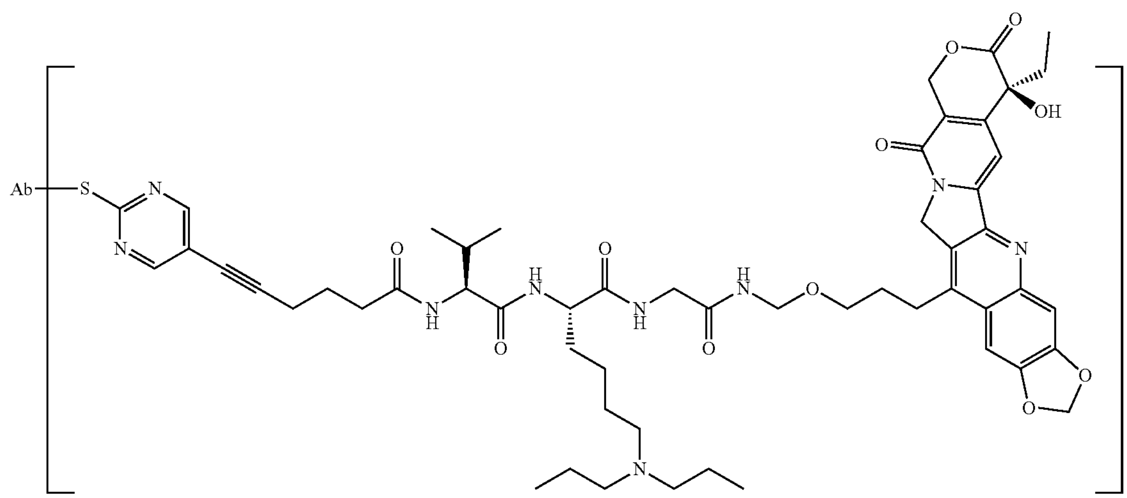

Ab is an antibody.

1.3.1. Preparation of CLDN18.2-ADC (DAR8) Sample 30 mg of the anti-CLDN18.2 antibody was diluted with a diluent (20 mM PB, pH 7.5), a sodium edetate solution at a final concentration of 5 mM was added, and the resulting mixture was well mixed. A TCEP solution that was 6.0 times the equivalent of the antibody was added, and the resulting mixture was well mixed and left to stand at room temperature for 60 min. DL-01 dissolved in dimethyl sulfoxide that was 12 times the equivalent of the antibody was added to the above solution system, and the resulting mixture was well mixed and left to stand at room temperature for 1 h to give a conjugate sample. After the reaction was completed, the sample was exchanged into a 10 mM histidine buffer solution with pH of 5.5 using a 30 KDa ultrafiltration tube to remove low-molecular weight substances, and finally the sample was concentrated to give a solution CLDN18.2-ADC (DAR8) containing the anti-CLDN18.2 antibody-ADC composition. The DAR value was determined to be 8.0 by mass spectrometry described in Example 3.4.

1.3.2. Preparation of CLDN18.2-ADC (DAR2) Sample 30 mg of the anti-CLDN18.2 antibody was diluted with a diluent (20 mM PB, pH 7.5), a sodium edetate solution at a final concentration of 5 mM was added, and the resulting mixture was well mixed. A TCEP solution that was 6.0 times the equivalent of the antibody was added, and the resulting mixture was well mixed and left to stand at room temperature for 60 min. DL-01 dissolved in dimethyl sulfoxide that was 2.5 times the equivalent of the antibody was added to the above solution system, and the resulting mixture was well mixed and left to stand at room temperature for 1 h to give a conjugate sample. After the reaction was completed, the sample was exchanged into a 10 mM histidine buffer solution with pH of 5.5 using a 30 KDa ultrafiltration tube to remove low-molecular weight substances, and finally the sample was concentrated to give a solution CLDN18.2-ADC (DAR2) containing the anti-CLDN18.2 antibody-ADC composition. The DAR value was determined to be 1.7 by mass spectrometry.

1.3.3. Preparation of CLDN18.2-ADC (DAR4) Sample 30 mg of the anti-CLDN18.2 antibody was diluted with a diluent (20 mM PB, pH 7.5), a sodium edetate solution at a final concentration of 5 mM was added, and the resulting mixture was well mixed. A TCEP solution that was 6.0 times the equivalent of the antibody was added, and the resulting mixture was well mixed and left to stand at room temperature for 60 min. DL-01 dissolved in dimethyl sulfoxide that was 4.5 times the equivalent of the antibody was added to the above solution system, and the resulting mixture was well mixed and left to stand at room temperature for 1 h to give a conjugate sample. After the reaction was completed, the sample was exchanged into a 10 mM histidine buffer solution with pH of 5.5 using a 30 KDa ultrafiltration tube to remove low-molecular weight substances, and finally the sample was concentrated to give a solution CLDN18.2-ADC (DAR4) containing the anti-CLDN18.2 antibody-ADC composition. The DAR value was determined to be 4.0 by mass spectrometry.

1.3.4. Preparation of CLDN18.2-ADC (DAR6) Sample 30 mg of the anti-CLDN18.2 antibody was diluted with a diluent (20 mM PB, pH 7.5), a sodium edetate solution at a final concentration of 5 mM was added, and the resulting mixture was well mixed. A TCEP solution that was 6.0 times the equivalent of the antibody was added, and the resulting mixture was well mixed and left to stand at room temperature for 60 min. DL-01 dissolved in dimethyl sulfoxide that was 7.0 times the equivalent of the antibody was added to the above solution system, and the resulting mixture was well mixed and left to stand at room temperature for 1 h to give a conjugate sample. After the reaction was completed, the sample was exchanged into a 10 mM histidine buffer solution with pH of 5.5 using a 30 KDa ultrafiltration tube to remove low-molecular weight substances, and finally the sample was concentrated to give a solution CLDN18.2-ADC-07 (DAR6) containing the anti-CLDN18.2 antibody-ADC composition. The DAR value was determined to be 5.6 by mass spectrometry.

Example 1.4. Determination of DAR Values of Conjugate Samples by Mass Spectrometry LC-MS molecular weight and DAR value analyses were performed on CLDN18.2-ADC-07 (DAR8) under the following conditions:

Chromatographic conditions:

chromatographic column: ACQUITY UPLC BEH200 SEC 1.7 m, 4.6×150 mm;

mobile phase A: 0.1% FA/$H_2O$, mobile phase B: 0.1% FA/ACN;
column temperature: 30° C.;
sample chamber temperature: 8° C.;
flow rate: 0.3 mL/min; and
sample injection volume: 1 μL.

| Time (min) | 1 | 5 | 7 | 7.1 | 10 |
|---|---|---|---|---|---|
| Mobile phase A | 90 | 40 | 10 | 90 | 90 |
| Mobile phase B | 10 | 80 | 80 | 10 | 10 |

Sample treatment: 50 g of the sample was taken, 2 μL of 1 M DTT was added, and ultrapure water was added to bring the volume to 50 μL, so that the solution was diluted to a concentration of about 1.0 mg/mL. The solution was well mixed and reduced at room temperature for 30 min.

LC/MS model: AB SCIEX X500 Q-TOF

Mass spectrum conditions: Gas1: 45; Gas2: 45; CUR: 30; TEM: 450; ISVF: 5000; DP: 120; CE: 12; and mass number range: 600-4000.

The results are shown in Table 9 below.

TABLE 9

Theoretical molecular weight and measured molecular weight

| | Peptide chain | mAb | DAR1 | DAR2 | DAR3 |
|---|---|---|---|---|---|
| LC | Theoretical value | 23426.6 | 24445 | NA | NA |
| | Measured value | Not detected | 24444.4 | Not detected | Not detected |
| HC | Theoretical value | 50211.8 | 51229.2 | 52246.6 | 53264 |
| | Measured value | Not detected | Not detected | Not detected | 53264.5 |

In Table 9, mAb represents an unconjugated monoclonal antibody; LC represents an antibody light chain; HC represents an antibody heavy chain; DAR1 represents a conjugate comprising a light chain or a heavy chain conjugated to 1 toxin molecule; DAR2 represents a conjugate comprising a light chain or a heavy chain conjugated to 2 toxin molecules; DAR3 represents a conjugate comprising a light chain or a heavy chain conjugated to 3 toxin molecules; wherein the theoretical molecular weight of the monoclonal antibody is calculated by GOF glycoform. In the following text, mAb, LC, HC, DAR1, DAR2, and DAR3 are as described above.

The detection results show that in the CLDN18.2-ADC (DAR8), the antibody light chain was conjugated to 0-1 toxin molecule (the proportions of LC and DAR1 are 0% and 100%, respectively), and the antibody heavy chain was conjugated to 0-3 toxin molecules (the proportions of mAb, DAR1, DAR2, and DAR3 are 0%, 0%, 0%, and 100%, respectively). Therefore, the drug-to-antibody ratio (DAR value) of CLDN18.2-ADC (DAR8) was calculated to be 8.0.

Similarly, the drug-to-antibody ratios (DAR values) can be determined for other conjugate samples using mass spectrometry.

Example 2. Anti-Claudin18.2 Antibody ADC Conjugation and Evaluation

Example 2.1. Anti-Claudin18.2 Antibody ADC Conjugation

According to the ADC preparation method described in Example 1, ADCs were constructed using 25C7A5-HZ1, 25C7A5-HZ2, and the isotype control IgG antibody.

1) Antibody pretreatment: A 0.1 M EDTA stock solution was added at 1% of the antibody volume, and then the pH of the sample was adjusted to 7.7±0.2 with a 1 M disodium hydrogen phosphate stock solution.
2) Preparation of TCEP stock solution: A certain mass of TCEP-HCL was weighed, and an 80% TCEP solvent was added. The pH was then adjusted to 7.7±0.2 with 0.5 M sodium hydroxide, and finally, the solution was brought to volume with a TCEP solvent to achieve a TCEP concentration of 20 mM.
3) Reduction: Each pretreated antibody was added to the TCEP stock solution at a 1:4.4 ratio (antibody-to-TCEP molar ratio), and the resulting mixture was well mixed and allowed to react at room temperature for 0.5 h.
4) Conjugation: A toxin linker was added to the reduced antibody at a 1:12 ratio (antibody-to-toxin molar ratio), and the resulting mixture was well mixed and allowed to react at room temperature for 2 h or more.
5) Ultrafiltration: The reaction solution was exchanged into an ultrafiltration buffer (10 mM HCl-His, pH 5.5) using an ultrafiltration tube (each concentration was followed by the addition of 4 volumes or more of the buffer, and the buffer exchange was performed 3 times or more), and then the ultrafiltration membrane was rinsed with a small amount of buffer to recover a sample.

The conjugate sample was detected for concentration, purity and DAR. The results are shown in Table 10, indicating that no significant aggregation was observed after conjugation of the antibody to ADC, and the purity was higher than 98% as determined by SEC-HPLC.

TABLE 10

Detection results for anti-Claudin18.2 humanized antibody ADCs

| No.* | Sample name | SEC (%) | DAR |
|---|---|---|---|
| 1 | 25C7A5-HZ1-B82 | 98.85 | 6.82 |
| 2 | 25C7A5-HZ2-B82 | 99.34 | 7.10 |
| 3 | IgG-B81 | 98.4 | 8.00 |
| 4 | 25C7A5-HZ1-B81 | 98.4 | 7.97 |

*Samples 1-2 and samples 3-4 are two batches of preparations prepared separately.

Example 2.2. Detection of Affinity of Anti-Claudin18.2 Humanized Antibodies and ADCs The cell binding affinity of the antibody before and after conjugation to the toxin was detected according to a method similar to that described in Example 2.2. L929-claudin 18.2 (human) or NUGC4 cells were digested with trypsin, collected by centrifugation, washed three times with pre-cooled PBS, resuspended, added to a 96-well plate at $5\times10^4$ cells/well, and incubated overnight. The cells were fixed with 4% paraformaldehyde and blocked with 2% BSA (in PBS) at 37° C. for 2 h. Each ADC drug or antibody subjected to gradient dilution was added, and the mixture was incubated at 37° C. for 2 h. An HRP-labeled anti-human secondary antibody (Jackson, 109-035-088) was then added, and the mixture was incubated at 37° C. for 1 h. A TMB substrate was added for color development, and after the reaction was stopped by 2 M HCl, $OD_{450\ nm}$ values were read on a microplate reader.

Figure 8A:
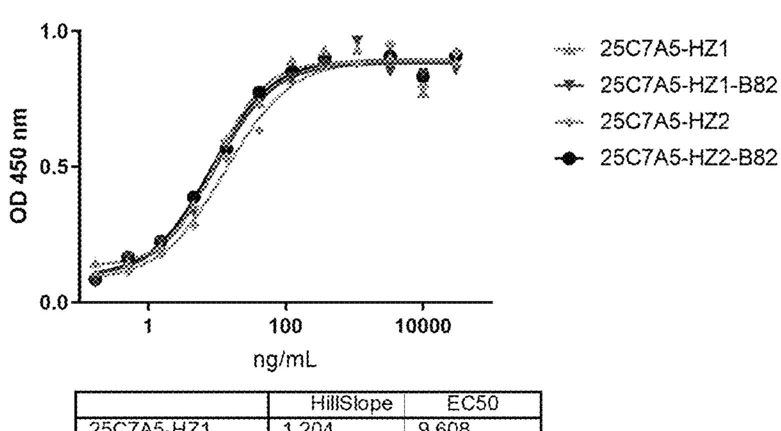
FIGS. 8A-8B show the binding of anti-Claudin18.2 humanized antibody ADCs to L929-Claudin18.2 cells (FIG. 8A) and NUGC4 cells (FIG. 8B) before and after conjugation to a toxin.
Figure 8B:
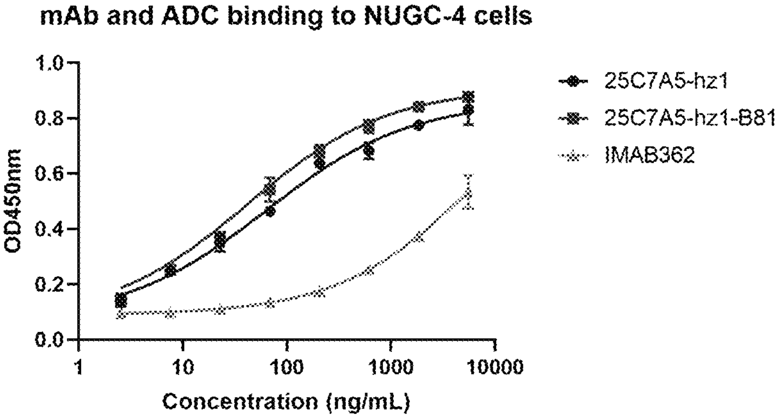
Figure 9A:
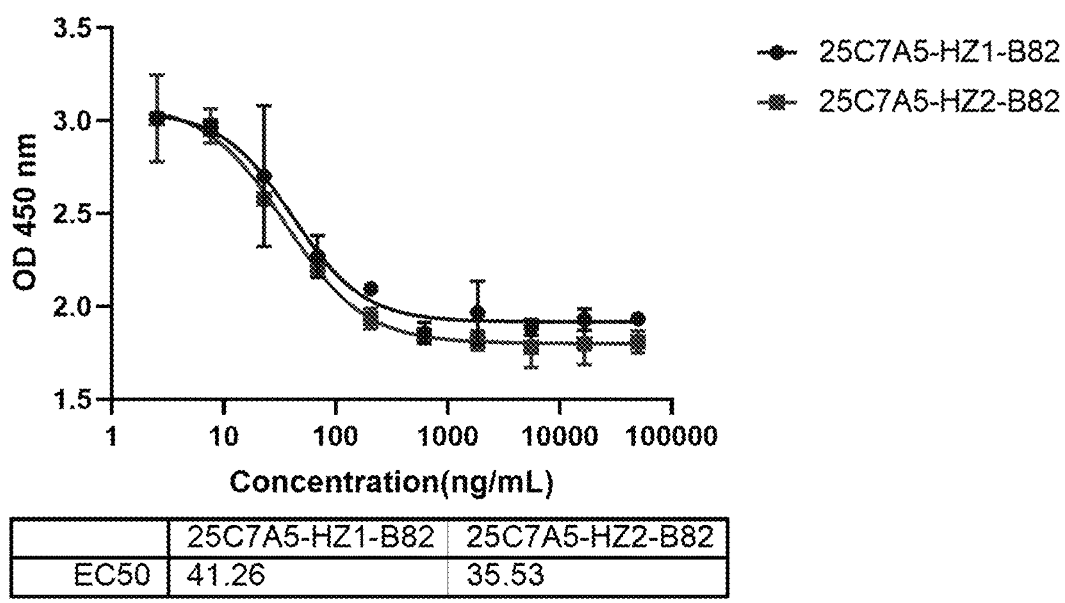
FIGS. 9A-9E show the killing effect of anti-Claudin18.2 humanized antibody ADC drugs on HEK293T-Claudin 18.2 cells (FIGS. 9A and 9B), HEK293T-Claudin 18.1 cells (FIGS. 9C and 9D), and NUGC4-Claudin 18.2 cells (FIG. 9E) in an in-vitro assay.
Figure 9B:
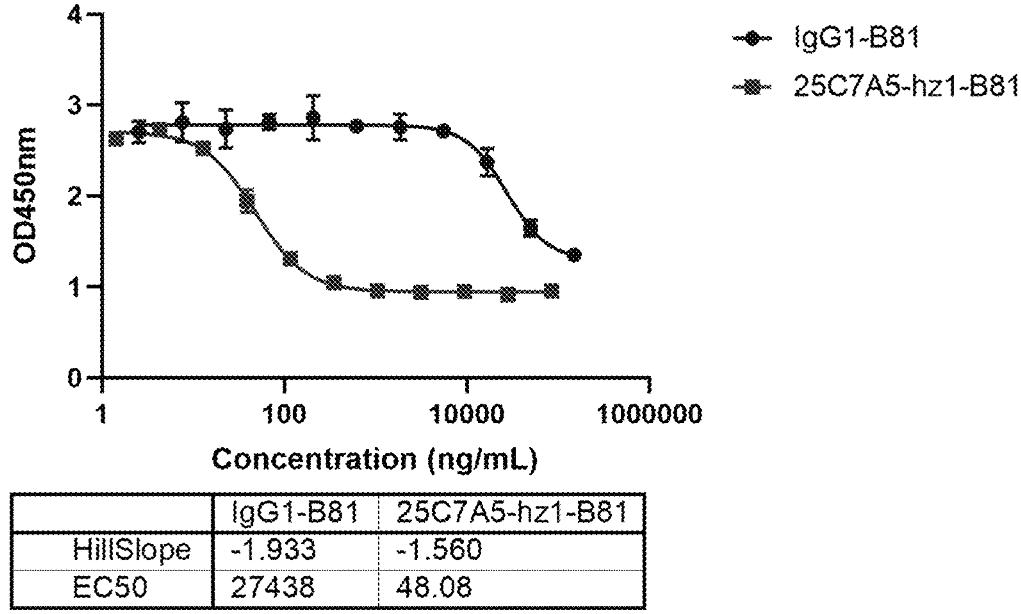
Figure 9C:
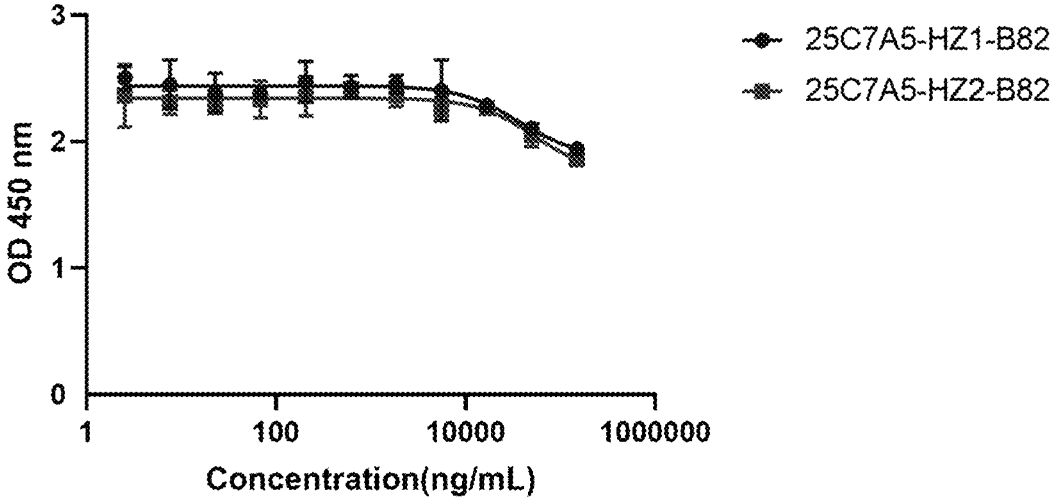
Figure 9D:
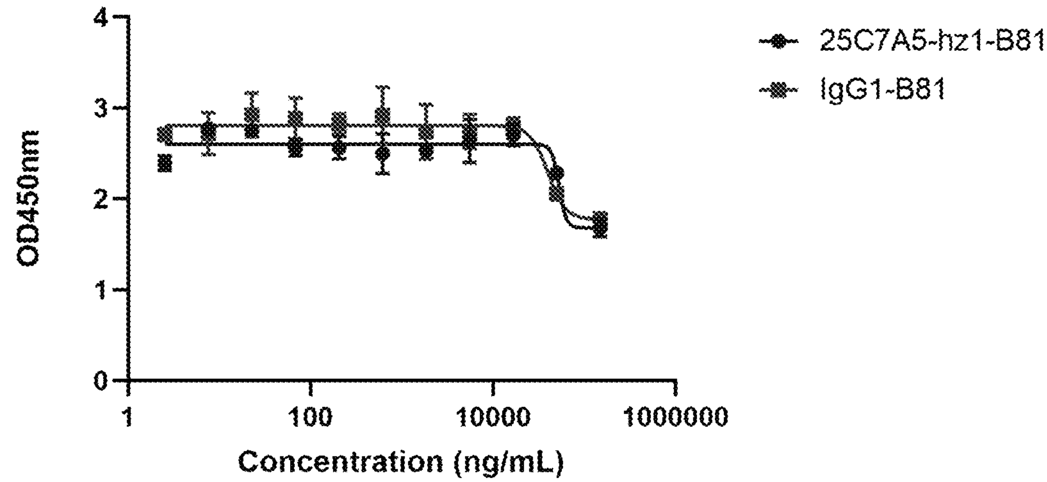
Figure 9E:
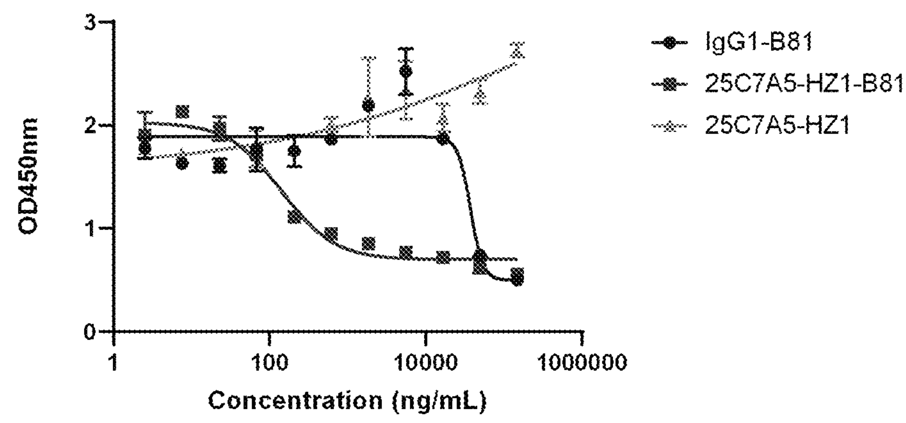

The experimental results are shown in FIGS. 8A and 8B, indicating that there were no significant changes in the affinity of 25C7A5-HZ1 and 25C7A5-HZ2 for the cells before and after conjugation.

Example 2.3. In-Vitro Killing Activity Assay on ADCs

HEK293T-claudin 18.2 (human) cells, HEK293T-claudin 18.1 (human) cells, and NUGC4-Claudin18.2 cells were digested with trypsin, collected by centrifugation, resuspended in DEME+2% FBS, and plated at 10000 cells/well. Each test antibody ADC drug was subjected to gradient dilution with DEME+2% FBS and added to the plate, and the mixture was incubated at 37° C. for 72 h. After the incubation was completed, a CCK8 reagent was added at 20 μL/well for reaction for 2-4 h. Readings were taken at 450 nm on a microplate reader and imported into Graphpad Prism for curve fitting.

The experimental results are shown in FIGS. 9A-9E, indicating that the ADCs formed by conjugation of 25C7A5-HZ1 and 25C7A5-HZ2 were both effective in killing HEK293T-claudin18.2 cells and NUGC-4-Claudin18.2 cells; meanwhile, the conjugated 25C7A5-HZ1 and 25C7A5-HZ2 substantially did not kill HEK293T-claudin18.1 cells, indicating that the conjugated ADCs did not non-specifically recognize claudin18.1 and had good stability.

Example 2.4. In-Vivo Efficacy of ADCs

In order to verify the in-vivo efficacy of the anti-Claudin18.2 humanized ADC drug, and to evaluate the anti-tumor effect of the test drug in a female Balb/c Nude mouse model with subcutaneously xenografted human gastric cancer cells NUGC-4 (Nanjing Cobioer), female Balb/c Nude mice aged 5-6 weeks (Vital River) were purchased. NUGC4 cells in the logarithmic growth phase were digested with EDTA and resuspended in PBS, and $5\times10^6$ cells were subcutaneously inoculated into each mouse. When the tumor grew to the size of 100-200 $m^3$, the ADC drug was intravenously administered once a week at 10 mg/kg. The specific regimen is shown in Table 7 below. The main observation indexes of the experiment are as follows: 1) relative tumor proliferation rate, T/C (%), i.e., the percentage value of the relative tumor volume or tumor weight of the treatment group and the control group at a certain time point, calculated as: T/C (%)=TRTV/CRTV×100% (TRTV: mean RTV of treatment group; CRTV: mean RTV of control group; RTV=Vt/V0, V0 is the tumor volume of the animal at the time of grouping, and Vt is the tumor volume of the animal after treatment); or T/C %=TTW/CTW×100% (TTW: mean tumor weight of treatment group at the end of experiment; CTW: mean tumor weight of control group at the end of experiment). 2) Relative tumor inhibition, TGI (%), calculated as: TGI (%)=(1−T/C)×100% (T and C are the relative tumor volume (RTV) or tumor weight (TW) of the treatment group and the control group, respectively, at a particular time point). 3) Photographs showing the tumor volume size, and tumor weight at the end of experiment. 4) Effect of the ADC drugs on the body weight of the mice.

TABLE 11

Experimental protocol for in-vivo efficacy of anti-Claudin18.2 humanized antibody ADCs

| Model | Group | Number | Sample | Dose (mg/kg) | Route of administration | Administration regimen |
|---|---|---|---|---|---|---|
| NUGC-4 | 1 | 5 | Control | / | i.v. | QW*3 wks |
| | 2 | 5 | IgG-B81 | 10 | i.v. | QW*3 wks |
| | 3 | 5 | 25C7A5-hz1-B81 | 10 | i.v. | QW*3 wks |
| | 4 | 5 | 25C7A5-hz1 | 10 | i.v. | QW*3 wks |

Figure 10:
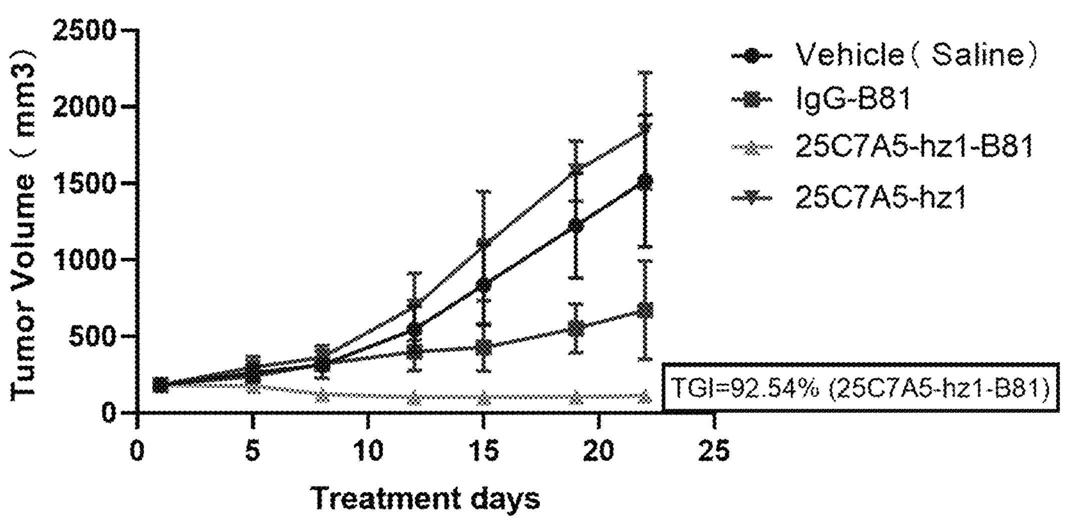
FIG. 10 shows the tumor inhibitory efficacy of an anti-Claudin18.2 humanized antibody ADC drug in an NUGC-4 CDX model.
Figure 11:
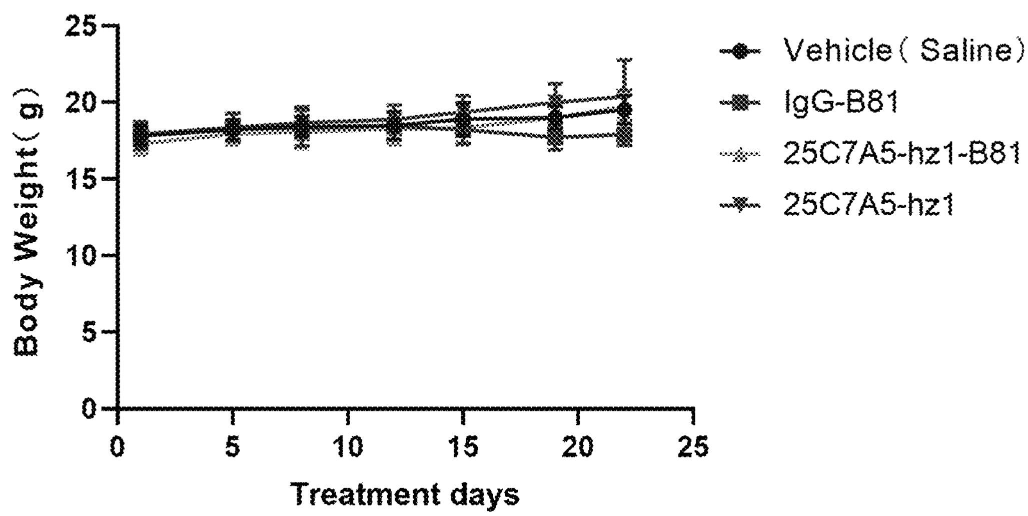
FIG. 11 shows the effect of an anti-Claudin18.2 humanized antibody ADC drug on the body weight of mice.

The experimental results are shown in FIGS. 10 and 11, indicating that 25C7A5-hzl-B81 showed significant efficacy in the NUGC-4 CDX model (FIG. 10); moreover, the drug was well tolerated by the mice overall, with no adverse reactions (FIG. 11).

Sequence Listing:

| SEQ ID NO: | Description | Sequence |
|---|---|---|
| 1 | Heavy chain variable region (VH) of 25C7A5-HZ1 | QVQLVQSGAEVKKPGSSVKVSCKASGYTFTNYWLHWV RQAPGQGLEWMGMMHPISGSSNYAQKFQGRATLTVDK STSTAYMELSSLRSEDTAVYYCARGLLSAMDYWGQGTL VTVSS |
| 2 | Light chain variable region (VL) of 25C7A5-HZ1/25C7A5-HZ2 | EIVLTQSPATLSLSPGERATLSCKASENVKTYVSWYQQKP GQSPRLLIYEASNRYTGVPARFSGSGSATDFTLTISSLEPE DFAVYFCGQTYSFPPTFGQGTKVEIK |
| 3 | Heavy chain variable region (VH) of 25C7A5-HZ2 | QVQLVESGAEVKKPGSSVKVSCKASGYTFTNYWLHWV RQAPGQGLEWMGMMHPISGSSNYAQKFQGRATLTVDK STSTAYMELSSLRSEDTAVYYCARGLLSAMDYWGQGTL VTVSS |
| 4 | Human IgG1 heavy chain constant region sequence | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPELLG |

-continued

| SEQ ID NO: | Description | Sequence |
|---|---|---|
| | | GPSVFLFPPKPKDTLMISRTPEVTCVVVDVSHEDPEVKF<br>NWYVDGVEVHNAKTKPREEQYNSTYRVVSVLTVLHQD<br>WLNGKEYKCKVSNKALPAPIEKTISKAKGQPREPQVYT<br>LPPSRDELTKNQVSLTCLVKGFYPSDIAVEWESNGQPEN<br>NYKTTPPVLDSDGSFFLYSKLTVDKSRWQQGNVFSCSV<br>MHEALHNHYTQKSLSLSPGK |
| 5 | Human Kappa light chain constant region sequence | RTVAAPSVFIFPPSDEQLKSGTASVVCLLNNFYPREAKVQ<br>WKVDNALQSGNSQESVTEQDSKDSTYSLSSTLTLSKAD<br>YEKHKVYACEVTHQGLSSPVTKSFNRGEC |
| 6 | IMGT heavy chain CDR1 of 25C7A5 | GYTFTNYW |
| 7 | IMGT heavy chain CDR2 of 25C7A5 | MHPISGSS |
| 8 | IMGT heavy chain CDR3 of 25C7A5 | ARGLLSAMDY |
| 9 | IMGT light chain CDR1 of 25C7A5 | ENVKTY |
| | IMGT light chain CDR2 of 25C7A5 | EAS |
| 11 | IMGT light chain CDR3 of 25C7A5 | GQTYSFPPT |
| 12 | Kabat heavy chain CDR1 of 25C7A5 | NYWLH |
| 13 | Kabat heavy chain CDR2 of 25C7A5-HZ1/2 | MMHPISGSSNYAQKFQG |
| 14 | Kabat heavy chain CDR3 of 25C7A5 | GLLSAMDY |
| 15 | Kabat light chain CDR1 of 25C7A5 | KASENVKTYVS |
| 16 | Kabat light chain CDR2 of 25C7A5 | EASNRYT |
| 17 | Kabat light chain CDR3 of 25C7A5 | GQTYSFPPT |
| 18 | Heavy chain intact sequence of 25C7A5-HZ1 | QVQLVQSGAEVKKPGSSVKVSCKASGYTFTNYWLHWV<br>RQAPGQGLEWMGMMHPISGSSNYAQKFQGRATLTVDK<br>STSTAYMELSSLRSEDTAVYYCARGLLSAMDYWGQGTL<br>VTVSSASTKGPSVFPLAPSSKSTSGGTAALGCLVKDYFPE<br>PVTVSWNSGALTSGVHTFPAVLQSSGLYSLSSVVTVPSSS<br>LGTQTYICNVNHKPSNTKVDKKVEPKSCDKTHTCPPCP<br>APELLGGPSVFLFPPKPKDTLMISRTPEVTCVVVDVSHE<br>DPEVKFNWYVDGVEVHNAKTKPREEQYNSTYRVVSVL<br>TVLHQDWLNGKEYKCKVSNKALPAPIEKTISKAKGQPR<br>EPQVYTLPPSRDELTKNQVSLTCLVKGFYPSDIAVEWESN<br>GQPENNYKTTPPVLDSDGSFFLYSKLTVDKSRWQQGNV<br>FSCSVMHEALHNHYTQKSLSLSPGK |

-continued

| SEQ ID NO: | Description | Sequence |
|---|---|---|
| 19 | Heavy chain intact sequence of 25C7A5-HZ2 | QVQLVESGAEVKKPGSSVKVSCKASGYTFTNYWLHWVRQAPGQGLEWMGMMHPISGSSNYAQKFQGRATLTVDKSTSTAYMELSSLRSEDTAVYYCARGLLSAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 20 | Light chain intact sequence of 25C7A5-HZ1/25C7A5-HZ2 | EIVLTQSPATLSLSPGERATLSCKASENVKTYVSWYQQKPGQSPRLLIYEASNRYTGVPARFSGSGSATDFTLTISSLEPEDFAVYFCGQTYSFPPTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 21 | Heavy chain variable region (VH) sequence of 25C7A5 | EVQLQQPGAELVKPGTSVKLSCKASGYTFTNYWLHWVRQRPGQGLEWIGMMHPISGSSNNNERFKSKATLTVDKSSTTAYMQLSRMTSEDSAVYYCARGLLSAMDYWGQGTSVTVSS |
| 22 | Light chain variable region (VL) sequence of 25C7A5 | CIVLTQSPKSMSMSVGERVTLSCKASENVKTYVSWYQQRPEQSPKLLIYEASNRYTGVPDRFTGSGSATVFTLTISSVQTEDLANYFCGQTYSFPPTFGSGTKLEIK |
| 23 | Heavy chain variable region (VH) sequence of 2D3A11 | EVQLQQSGPELVKPGASVRMSCKASGYTFTSYVVHWVKQKPGQGLEWIGYINPYNADSKYNERFKGKATLTSDKSSNSAYMELSSLTSEDSAVYYCSRSYYGNSFDVWGAGTTVTVSS |
| 24 | Light chain variable region (VL) sequence of 2D3A11 | DIVMTQSPSSLTVTTGEKVTMSCKSSQSLLNSGNQKNYLTWYQQKPGQSPKLLFFWASTRQSGVPDRFTGSGSGTYFTLTISSVQAEDLAVYYCQNDYYFPFTFGTGTKLEIK |
| 25 | Kabat heavy chain CDR2 of 25C7A5 | MMHPISGSSNNNERFKS |
| 26 | Kabat heavy chain CDR1 of 2D3A11 | SYVVH |
| 27 | Kabat heavy chain CDR2 of 2D3A11 | YINPYNADSKYNERFKG |
| 28 | Kabat heavy chain CDR3 of 2D3A11 | SYYGNSFDV |
| 29 | IMGT heavy chain CDR1 of 2D3A11 | GYTFTSYV |
| 30 | IMGT heavy chain CDR2 of 2D3A11 | INPYNADS |
| 31 | IMGT heavy chain CDR3 of 2D3A11 | SRSYYGNSFDV |
| 32 | Kabat light chain CDR1 of 2D3A11 | KSSQSLLNSGNQKNYLT |
| 33 | Kabat light chain CDR2 of 2D3A11 | WASTRQS |
| 34 | Kabat/IMGT light chain CDR3 of 2D3A11 | QNDYYFPFT |
| 35 | IMGT light chain CDR1 of 2D3A11 | QSLLNSGNQKNY |
| | IMGT light chain CDR2 of 2D3A11 | WAS |

-continued

| SEQ ID NO: | Description | Sequence |
| --- | --- | --- |
| 37 | Kabat heavy chain CDR2 of 2D3A11-HZ1/2 | YINPYNADSKYSQEFQG |
| 38 | Heavy chain variable region (VH) of 2D3A11-HZ1 | QVQLVQSGAEVKKPGASVKVSCKASGYTFTSYVVHWV RQAPGQGLEWMGYINPYNADSKYSQEFQGRATLTSDKS ASTAYMELSSLRSEDMAVYYCSRSYYGNSFDVWGQGTL VTVSS |
| 39 | Light chain variable region (VL) of 2D3A11-HZ1/2D3A11-HZ2 | DIVMTQSPDSLAVSLGERATINCKSSQSLLNSGNQKNYLT WYQQKPGQSPKLLFFWASTRQSGVPDRFSGSGSGTDFT LTISSLQAEDVAVYYCQNDYYFPFTFGQGTKVEIK |
| 40 | Heavy chain variable region (VH) of 2D3A11-HZ2 | QVQLVESGAEVKKPGASVKVSCKASGYTFTSYVVHWV RQAPGQGLEWMGYINPYNADSKYSQEFQGRATLTSDKS ASTAYMELSSLRSEDMAVYYCSRSYYGNSFDVWGQGTL VTVSS |
| 41 | Heavy chain intact sequence of 2D3A11-HZ1 | QVQLVQSGAEVKKPGASVKVSCKASGYTFTSYVVHWV RQAPGQGLEWMGYINPYNADSKYSQEFQGRATLTSDKS ASTAYMELSSLRSEDMAVYYCSRSYYGNSFDVWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSCDKTHTCPPCP APELLGGPSVFLFPPKPKDTLMISRTPEVTCVVVDVSHE DPEVKFNWYVDGVEVHNAKTKPREEQYNSTYRVVSVL TVLHQDWLNGKEYKCKVSNKALPAPIEKTISKAKGQPR EPQVYTLPPSRDELTKNQVSLTCLVKGFYPSDIAVEWESN GQPENNYKTTPPVLDSDGSFFLYSKLTVDKSRWQQGNV FSCSVMHEALHNHYTQKSLSLSPGK |
| 42 | Heavy chain intact sequence of 2D3A11-HZ2 | QVQLVESGAEVKKPGASVKVSCKASGYTFTSYVVHWV RQAPGQGLEWMGYINPYNADSKYSQEFQGRATLTSDKS ASTAYMELSSLRSEDMAVYYCSRSYYGNSFDVWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSCDKTHTCPPCP APELLGGPSVFLFPPKPKDTLMISRTPEVTCVVVDVSHE DPEVKFNWYVDGVEVHNAKTKPREEQYNSTYRVVSVL TVLHQDWLNGKEYKCKVSNKALPAPIEKTISKAKGQPR EPQVYTLPPSRDELTKNQVSLTCLVKGFYPSDIAVEWESN GQPENNYKTTPPVLDSDGSFFLYSKLTVDKSRWQQGNV FSCSVMHEALHNHYTQKSLSLSPGK |
| 43 | Light chain intact sequence of 2D3A11-HZ1/2D3A11-HZ2 | DIVMTQSPDSLAVSLGERATINCKSSQSLLNSGNQKNYLT WYQQKPGQSPKLLFFWASTRQSGVPDRFSGSGSGTDFT LTISSLQAEDVAVYYCQNDYYFPFTFGQGTKVEIKRTVA APSVFIFPPSDEQLKSGTASVVCLLNNFYPREAKVQWKV DNALQSGNSQESVTEQDSKDSTYSLSSTLTLSKADYEKH KVYACEVTHQGLSSPVTKSFNRGEC |
| 44 | Heavy chain variable region (VH) sequence of 8H11A10 | QVQLKESGPVLVAPSQSLSITCTVSGFSLTNYGVHWVRQ PPGKGLEWLGVIWSGGRTNYNSALMSRLSISKDNSKSQ VFLKMNSLQTDDTAMYYCAKRDGIYGDYWGQGTSVT VSS |
| 45 | Light chain variable region (VL) sequence of 8H11A10 | DIVETQSPSSLTVTAGEKVTMSCKSSQSLLNSGNQKNYL TWYQQKPGQSPKLLIYWASTRESGVPDRFTGSGFGTDFT LTISSVQAEDLAVYYCQNDYIYPLTFGAGTKLELK |
| 46 | Heavy chain variable region (VH) sequence of 1A6G10 | QVQLKESGGGLVKPGGSLKLSCAASGFTFSSYAMSWVR QTPEKRLEWVAAIHSNGGSTYNSDTMRDRFTISRDHAK NTLYLQMSSLRSEDTALYYCGRQSFGNALDYWGQGTSV TVSS |
| 47 | Light chain variable region (VL) sequence of 1A6G10 | DIQMTQSPSSLTVTAGEKVTLTCKSSQSLLNSGNQKNYL TWYQQKPGQPPKLLIYWASTRESGVPDRFTGSGSGTFFT LTISSVQAEDLAVYFCQNDYVYPFTFGAGTQLELK |
| 48 | Heavy chain variable region (VH) sequence of 23F2F2 | QVQLKESGGGLVQPGGSMKLSCAASGFTFSDAWMNWV RQSPEKGLEWVAEIRNKADYHATHYVESVTGRFTISRDD SKSSVYLQMNRLRAEDTGIYYCTRNYGSRFDYWGQGT TLTVSS |

-continued

| SEQ ID NO: | Description | Sequence |
|---|---|---|
| 49 | Light chain variable region (VL) sequence of 23F2F2 | DIVETQSPSSLTVTAGEKVTMSCKSSQSLLNSGNQRNYL TWYQQKPGHPPKLLIYWASTRESGVPDRFTGSGSGTDFT LTVTSVQAEDLAVYYCQNDYFYPLAFGTGTKLELK |
| 50 | Heavy chain variable region (VH) sequence of 40G11H | EVQLQQSGAELARPGASVKLSCKASGYTFTSYGIRWVK QRTGQGLEWIGEIYPRGGNTYYDEKFKGKATLTADKSSS TAYMGLRSLTSEDSAVYFCARADYGNSFAYWGQGTLVT VSA |
| 51 | Light chain variable region (VL) sequence of 40G11H | DIVMTQSPSSLTVTAREKVTMSCKSSQSLLNSGNQKNYL TWYHQKPGQPPKLLIYWASTRESGVPDRFTGSGSGTDFT LTISSVQAEDLAVYFCQNAYFYPFTFGTGTKLEIK |
| 52 | Heavy chain variable region (VH) sequence of 32F7A6 | QIQLVQSGPELRKPGETVKISCKASGYTFTAYTMGWVK QAPGKGLEWMAWINTYSGVPTYAADFKGRFAFSLETSA STAYLLINNLKNEDTATYFCARGVRGNSMDYWGQGTSV TVSS |
| 53 | Light chain variable region (VL) sequence of 32F7A6 | DIVETQSPSSLTVTVGERVTLSCKSSQSLLNSGNQRNYLT WSQQKPGQPPKLLIYWASTRESGVPNRFTGGGSGTYFTL TISSVQVEDLAVYYCQNTYSFPFTFGTGTKLEIK |

SEQUENCE LISTING

```
Sequence total quantity: 58
SEQ ID NO: 1            moltype = AA  length = 117
FEATURE                 Location/Qualifiers
source                  1..117
                        mol_type = protein
                        note = Artificial Sequence
                        organism = unidentified
SEQUENCE: 1
QVQLVQSGAE VKKPGSSVKV SCKASGYTFT NYWLHWVRQA PGQGLEWMGM MHPISGSSNY  60
AQKFQGRATL TVDKSTSTAY MELSSLRSED TAVYYCARGL LSAMDYWGQG TLVTVSS     117

SEQ ID NO: 2            moltype = AA  length = 107
FEATURE                 Location/Qualifiers
source                  1..107
                        mol_type = protein
                        note = Artificial Sequence
                        organism = unidentified
SEQUENCE: 2
EIVLTQSPAT LSLSPGERAT LSCKASENVK TYVSWYQQKP GQSPRLLIYE ASNRYTGVPA  60
RFSGSGSATD FTLTISSLEP EDFAVYFCGQ TYSFPPTFGQ GTKVEIK                107

SEQ ID NO: 3            moltype = AA  length = 117
FEATURE                 Location/Qualifiers
source                  1..117
                        mol_type = protein
                        note = Artificial Sequence
                        organism = unidentified
SEQUENCE: 3
QVQLVESGAE VKKPGSSVKV SCKASGYTFT NYWLHWVRQA PGQGLEWMGM MHPISGSSNY  60
AQKFQGRATL TVDKSTSTAY MELSSLRSED TAVYYCARGL LSAMDYWGQG TLVTVSS     117

SEQ ID NO: 4            moltype = AA  length = 330
FEATURE                 Location/Qualifiers
source                  1..330
                        mol_type = protein
                        note = Artificial Sequence
                        organism = unidentified
SEQUENCE: 4
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 5            moltype = AA  length = 107
FEATURE                 Location/Qualifiers
source                  1..107
```

```
                        mol_type = protein
                        note = Artificial Sequence
                        organism = unidentified
SEQUENCE: 5
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC                107

SEQ ID NO: 6            moltype = AA  length = 8
FEATURE                 Location/Qualifiers
source                  1..8
                        mol_type = protein
                        note = Artificial Sequence
                        organism = unidentified
SEQUENCE: 6
GYTFTNYW                                                           8

SEQ ID NO: 7            moltype = AA  length = 8
FEATURE                 Location/Qualifiers
source                  1..8
                        mol_type = protein
                        note = Artificial Sequence
                        organism = unidentified
SEQUENCE: 7
MHPISGSS                                                           8

SEQ ID NO: 8            moltype = AA  length = 10
FEATURE                 Location/Qualifiers
source                  1..10
                        mol_type = protein
                        note = Artificial Sequence
                        organism = unidentified
SEQUENCE: 8
ARGLLSAMDY                                                         10

SEQ ID NO: 9            moltype = AA  length = 6
FEATURE                 Location/Qualifiers
source                  1..6
                        mol_type = protein
                        note = Artificial Sequence
                        organism = unidentified
SEQUENCE: 9
ENVKTY                                                             6

SEQ ID NO: 10           moltype =   length =
SEQUENCE: 10
000

SEQ ID NO: 11           moltype = AA  length = 9
FEATURE                 Location/Qualifiers
source                  1..9
                        mol_type = protein
                        note = Artificial Sequence
                        organism = unidentified
SEQUENCE: 11
GQTYSFPPT                                                          9

SEQ ID NO: 12           moltype = AA  length = 5
FEATURE                 Location/Qualifiers
source                  1..5
                        mol_type = protein
                        note = Artificial Sequence
                        organism = unidentified
SEQUENCE: 12
NYWLH                                                              5

SEQ ID NO: 13           moltype = AA  length = 17
FEATURE                 Location/Qualifiers
source                  1..17
                        mol_type = protein
                        note = Artificial Sequence
                        organism = unidentified
SEQUENCE: 13
MMHPISGSSN YAQKFQG                                                 17

SEQ ID NO: 14           moltype = AA  length = 8
FEATURE                 Location/Qualifiers
source                  1..8
                        mol_type = protein
                        note = Artificial Sequence
```

```
                        organism = unidentified
SEQUENCE: 14
GLLSAMDY                                                         8

SEQ ID NO: 15           moltype = AA  length = 11
FEATURE                 Location/Qualifiers
source                  1..11
                        mol_type = protein
                        note = Artificial Sequence
                        organism = unidentified
SEQUENCE: 15
KASENVKTYV S                                                     11

SEQ ID NO: 16           moltype = AA  length = 7
FEATURE                 Location/Qualifiers
source                  1..7
                        mol_type = protein
                        note = Artificial Sequence
                        organism = unidentified
SEQUENCE: 16
EASNRYT                                                          7

SEQ ID NO: 17           moltype = AA  length = 9
FEATURE                 Location/Qualifiers
source                  1..9
                        mol_type = protein
                        note = Artificial Sequence
                        organism = unidentified
SEQUENCE: 17
GQTYSFPPT                                                        9

SEQ ID NO: 18           moltype = AA  length = 447
FEATURE                 Location/Qualifiers
source                  1..447
                        mol_type = protein
                        note = Artificial Sequence
                        organism = unidentified
SEQUENCE: 18
QVQLVQSGAE VKKPGSSVKV SCKASGYTFT NYWLHWVRQA PGQGLEWMGM MHPISGSSNY  60
AQKFQGRATL TVDKSTSTAY MELSSLRSED TAVYYCARGL LSAMDYWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APELLGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSRDELTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                    447

SEQ ID NO: 19           moltype = AA  length = 447
FEATURE                 Location/Qualifiers
source                  1..447
                        mol_type = protein
                        note = Artificial Sequence
                        organism = unidentified
SEQUENCE: 19
QVQLVESGAE VKKPGSSVKV SCKASGYTFT NYWLHWVRQA PGQGLEWMGM MHPISGSSNY  60
AQKFQGRATL TVDKSTSTAY MELSSLRSED TAVYYCARGL LSAMDYWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APELLGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSRDELTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                    447

SEQ ID NO: 20           moltype = AA  length = 214
FEATURE                 Location/Qualifiers
source                  1..214
                        mol_type = protein
                        note = Artificial Sequence
                        organism = unidentified
SEQUENCE: 20
EIVLTQSPAT LSLSPGERAT LSCKASENVK TYVSWYQQKP GQSPRLLIYE ASNRYTGVPA  60
RFSGSGSATD FTLTISSLEP EDFAVYFCGQ TYSFPPTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 21           moltype = AA  length = 117
FEATURE                 Location/Qualifiers
source                  1..117
                        mol_type = protein
```

```
                        note = Artificial Sequence
                        organism = unidentified
SEQUENCE: 21
EVQLQQPGAE LVKPGTSVKL SCKASGYTFT NYWLHWVRQR PGQGLEWIGM MHPISGSSNN  60
NERFKSKATL TVDKSSTTAY MQLSRMTSED SAVYYCARGL LSAMDYWGQG TSVTVSS     117

SEQ ID NO: 22           moltype = AA  length = 107
FEATURE                 Location/Qualifiers
source                  1..107
                        mol_type = protein
                        note = Artificial Sequence
                        organism = unidentified
SEQUENCE: 22
CIVLTQSPKS MSMSVGERVT LSCKASENVK TYVSWYQQRP EQSPKLLIYE ASNRYTGVPD  60
RFTGSGSATV FTLTISSVQT EDLANYFCGQ TYSFPPTFGS GTKLEIK               107

SEQ ID NO: 23           moltype = AA  length = 118
FEATURE                 Location/Qualifiers
source                  1..118
                        mol_type = protein
                        note = Artificial Sequence
                        organism = unidentified
SEQUENCE: 23
EVQLQQSGPE LVKPGASVRM SCKASGYTFT SYVVHWVKQK PGQGLEWIGY INPYNADSKY  60
NERFKGKATL TSDKSSNSAY MELSSLTSED SAVYYCSRSY YGNSFDVWGA GTTVTVSS    118

SEQ ID NO: 24           moltype = AA  length = 113
FEATURE                 Location/Qualifiers
source                  1..113
                        mol_type = protein
                        note = Artificial Sequence
                        organism = unidentified
SEQUENCE: 24
DIVMTQSPSS LTVTTGEKVT MSCKSSQSLL NSGNQKNYLT WYQQKPGQSP KLLFFWASTR  60
QSGVPDRFTG SGSGTYFTLT ISSVQAEDLA VYYCQNDYYF PFTFGTGTKL EIK         113

SEQ ID NO: 25           moltype = AA  length = 17
FEATURE                 Location/Qualifiers
source                  1..17
                        mol_type = protein
                        note = Artificial Sequence
                        organism = unidentified
SEQUENCE: 25
MMHPISGSSN NNERFKS                                                 17

SEQ ID NO: 26           moltype = AA  length = 5
FEATURE                 Location/Qualifiers
source                  1..5
                        mol_type = protein
                        note = Artificial Sequence
                        organism = unidentified
SEQUENCE: 26
SYVVH                                                              5

SEQ ID NO: 27           moltype = AA  length = 17
FEATURE                 Location/Qualifiers
source                  1..17
                        mol_type = protein
                        note = Artificial Sequence
                        organism = unidentified
SEQUENCE: 27
YINPYNADSK YNERFKG                                                 17

SEQ ID NO: 28           moltype = AA  length = 9
FEATURE                 Location/Qualifiers
source                  1..9
                        mol_type = protein
                        note = Artificial Sequence
                        organism = unidentified
SEQUENCE: 28
SYYGNSFDV                                                          9

SEQ ID NO: 29           moltype = AA  length = 8
FEATURE                 Location/Qualifiers
source                  1..8
                        mol_type = protein
                        note = Artificial Sequence
                        organism = unidentified
SEQUENCE: 29
```

```
GYTFTSYV                                                          8

SEQ ID NO: 30          moltype = AA  length = 8
FEATURE                Location/Qualifiers
source                 1..8
                       mol_type = protein
                       note = Artificial Sequence
                       organism = unidentified
SEQUENCE: 30
INPYNADS                                                          8

SEQ ID NO: 31          moltype = AA  length = 11
FEATURE                Location/Qualifiers
source                 1..11
                       mol_type = protein
                       note = Artificial Sequence
                       organism = unidentified
SEQUENCE: 31
SRSYYGNSFD V                                                      11

SEQ ID NO: 32          moltype = AA  length = 17
FEATURE                Location/Qualifiers
source                 1..17
                       mol_type = protein
                       note = Artificial Sequence
                       organism = unidentified
SEQUENCE: 32
KSSQSLLNSG NQKNYLT                                                17

SEQ ID NO: 33          moltype = AA  length = 7
FEATURE                Location/Qualifiers
source                 1..7
                       mol_type = protein
                       note = Artificial Sequence
                       organism = unidentified
SEQUENCE: 33
WASTRQS                                                           7

SEQ ID NO: 34          moltype = AA  length = 9
FEATURE                Location/Qualifiers
source                 1..9
                       mol_type = protein
                       note = Artificial Sequence
                       organism = unidentified
SEQUENCE: 34
QNDYYFPFT                                                         9

SEQ ID NO: 35          moltype = AA  length = 12
FEATURE                Location/Qualifiers
source                 1..12
                       mol_type = protein
                       note = Artificial Sequence
                       organism = unidentified
SEQUENCE: 35
QSLLNSGNQK NY                                                     12

SEQ ID NO: 36          moltype =   length =
SEQUENCE: 36
000

SEQ ID NO: 37          moltype = AA  length = 17
FEATURE                Location/Qualifiers
source                 1..17
                       mol_type = protein
                       note = Artificial Sequence
                       organism = unidentified
SEQUENCE: 37
YINPYNADSK YSQEFQG                                                17

SEQ ID NO: 38          moltype = AA  length = 118
FEATURE                Location/Qualifiers
source                 1..118
                       mol_type = protein
                       note = Artificial Sequence
                       organism = unidentified
SEQUENCE: 38
QVQLVQSGAE VKKPGASVKV SCKASGYTFT SYVVHWVRQA PGQGLEWMGY INPYNADSKY  60
SQEFQGRATL TSDKSASTAY MELSSLRSED MAVYYCSRSY YGNSFDVWGQ GTLVTVSS    118
```

-continued

```
SEQ ID NO: 39          moltype = AA  length = 113
FEATURE                Location/Qualifiers
source                 1..113
                       mol_type = protein
                       note = Artificial Sequence
                       organism = unidentified
SEQUENCE: 39
DIVMTQSPDS LAVSLGERAT INCKSSQSLL NSGNQKNYLT WYQQKPGQSP KLLFFWASTR  60
QSGVPDRFSG SGSGTDFTLT ISSLQAEDVA VYYCQNDYYF PFTFGQGTKV EIK         113

SEQ ID NO: 40          moltype = AA  length = 118
FEATURE                Location/Qualifiers
source                 1..118
                       mol_type = protein
                       note = Artificial Sequence
                       organism = unidentified
SEQUENCE: 40
QVQLVESGAE VKKPGASVKV SCKASGYTFT SYVVHWVRQA PGQGLEWMGY INPYNADSKY  60
SQEFQGRATL TSDKSASTAY MELSSLRSED MAVYYCSRSY YGNSFDVWGQ GTLVTVSS    118

SEQ ID NO: 41          moltype = AA  length = 448
FEATURE                Location/Qualifiers
source                 1..448
                       mol_type = protein
                       note = Artificial Sequence
                       organism = unidentified
SEQUENCE: 41
QVQLVQSGAE VKKPGASVKV SCKASGYTFT SYVVHWVRQA PGQGLEWMGY INPYNADSKY  60
SQEFQGRATL TSDKSASTAY MELSSLRSED MAVYYCSRSY YGNSFDVWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                     448

SEQ ID NO: 42          moltype = AA  length = 448
FEATURE                Location/Qualifiers
source                 1..448
                       mol_type = protein
                       note = Artificial Sequence
                       organism = unidentified
SEQUENCE: 42
QVQLVESGAE VKKPGASVKV SCKASGYTFT SYVVHWVRQA PGQGLEWMGY INPYNADSKY  60
SQEFQGRATL TSDKSASTAY MELSSLRSED MAVYYCSRSY YGNSFDVWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                     448

SEQ ID NO: 43          moltype = AA  length = 220
FEATURE                Location/Qualifiers
source                 1..220
                       mol_type = protein
                       note = Artificial Sequence
                       organism = unidentified
SEQUENCE: 43
DIVMTQSPDS LAVSLGERAT INCKSSQSLL NSGNQKNYLT WYQQKPGQSP KLLFFWASTR  60
QSGVPDRFSG SGSGTDFTLT ISSLQAEDVA VYYCQNDYYF PFTFGQGTKV EIKRTVAAPS  120
VFIFPPSDEQ LKSGTASVVC LLNNFYPREA KVQWKVDNAL QSGNSQESVT EQDSKDSTYS  180
LSSTLTLSKA DYEKHKVYAC EVTHQGLSSP VTKSFNRGEC                        220

SEQ ID NO: 44          moltype = AA  length = 116
FEATURE                Location/Qualifiers
source                 1..116
                       mol_type = protein
                       note = Artificial Sequence
                       organism = unidentified
SEQUENCE: 44
QVQLKESGPV LVAPSQSLSI TCTVSGFSLT NYGVHWVRQP PGKGLEWLGV IWSGGRTNYN  60
SALMSRLSIS KDNSKSQVFL KMNSLQTDDT AMYYCAKRDG IYGDYWGQGT SVTVSS      116

SEQ ID NO: 45          moltype = AA  length = 113
FEATURE                Location/Qualifiers
source                 1..113
                       mol_type = protein
                       note = Artificial Sequence
```

```
                        organism = unidentified
SEQUENCE: 45
DIVETQSPSS LTVTAGEKVT MSCKSSQSLL NSGNQKNYLT WYQQKPGQSP KLLIYWASTR  60
ESGVPDRFTG SGFGTDFTLT ISSVQAEDLA VYYCQNDYIY PLTFGAGTKL ELK         113

SEQ ID NO: 46           moltype = AA  length = 118
FEATURE                 Location/Qualifiers
source                  1..118
                        mol_type = protein
                        note = Artificial Sequence
                        organism = unidentified
SEQUENCE: 46
QVQLKESGGG LVKPGGSLKL SCAASGFTFS SYAMSWVRQT PEKRLEWVAA IHSNGGSTYN  60
SDTMRDRFTI SRDHAKNTLY LQMSSLRSED TALYYCGRQS FGNALDYWGQ GTSVTVSS    118

SEQ ID NO: 47           moltype = AA  length = 113
FEATURE                 Location/Qualifiers
source                  1..113
                        mol_type = protein
                        note = Artificial Sequence
                        organism = unidentified
SEQUENCE: 47
DIQMTQSPSS LTVTAGEKVT LTCKSSQSLL NSGNQKNYLT WYQQKPGQPP KLLIYWASTR  60
ESGVPDRFTG SGSGTFFTLT ISSVQAEDLA VYFCQNDYVY PFTFGAGTQL ELK         113

SEQ ID NO: 48           moltype = AA  length = 119
FEATURE                 Location/Qualifiers
source                  1..119
                        mol_type = protein
                        note = Artificial Sequence
                        organism = unidentified
SEQUENCE: 48
QVQLKESGGG LVQPGGSMKL SCAASGFTFS DAWMNWVRQS PEKGLEWVAE IRNKADYHAT  60
HYVESVTGRF TISRDDSKSS VYLQMNRLRA EDTGIYYCTR NYGSRFDYWG QGTTLTVSS   119

SEQ ID NO: 49           moltype = AA  length = 113
FEATURE                 Location/Qualifiers
source                  1..113
                        mol_type = protein
                        note = Artificial Sequence
                        organism = unidentified
SEQUENCE: 49
DIVETQSPSS LTVTAGEKVT MSCKSSQSLL NSGNQRNYLT WYQQKPGHPP KLLIYWASTR  60
ESGVPDRFTG SGSGTDFTLT VTSVQAEDLA VYYCQNDYFY PLAFGTGTKL ELK         113

SEQ ID NO: 50           moltype = AA  length = 118
FEATURE                 Location/Qualifiers
source                  1..118
                        mol_type = protein
                        note = Artificial Sequence
                        organism = unidentified
SEQUENCE: 50
EVQLQQSGAE LARPGASVKL SCKASGYTFT SYGIRWVKQR TGQGLEWIGE IYPRGGNTYY  60
DEKFKGKATL TADKSSSTAY MGLRSLTSED SAVYFCARAD YGNSFAYWGQ GTLVTVSA    118

SEQ ID NO: 51           moltype = AA  length = 113
FEATURE                 Location/Qualifiers
source                  1..113
                        mol_type = protein
                        note = Artificial Sequence
                        organism = unidentified
SEQUENCE: 51
DIVMTQSPSS LTVTAREKVT MSCKSSQSLL NSGNQKNYLT WYHQKPGQPP KLLIYWASTR  60
ESGVPDRFTG SGSGTDFTLT ISSVQAEDLA VYFCQNAYFY PFTFGTGTKL EIK         113

SEQ ID NO: 52           moltype = AA  length = 118
FEATURE                 Location/Qualifiers
source                  1..118
                        mol_type = protein
                        note = Artificial Sequence
                        organism = unidentified
SEQUENCE: 52
QIQLVQSGPE LRKPGETVKI SCKASGYTFT AYTMGWVKQA PGKGLEWMAW INTYSGVPTY  60
AADFKGRFAF SLETSASTAY LLINNLKNED TATYFCARGV RGNSMDYWGQ GTSVTVSS    118

SEQ ID NO: 53           moltype = AA  length = 113
FEATURE                 Location/Qualifiers
source                  1..113
                        mol_type = protein
```

-continued

```
                        note = Artificial Sequence
                        organism = unidentified
SEQUENCE: 53
DIVETQSPSS LTVTVGERVT LSCKSSQSLL NSGNQRNYLT WSQQKPGQPP KLLIYWASTR  60
ESGVPNRFTG GGSGTYFTLT ISSVQVEDLA VYYCQNTYSF PFTFGTGTKL EIK        113

SEQ ID NO: 54           moltype = AA  length = 4
FEATURE                 Location/Qualifiers
source                  1..4
                        mol_type = protein
                        organism = synthetic construct
SEQUENCE: 54
GFLG                                                              4

SEQ ID NO: 55           moltype = AA  length = 4
FEATURE                 Location/Qualifiers
source                  1..4
                        mol_type = protein
                        organism = synthetic construct
SEQUENCE: 55
ALAL                                                              4

SEQ ID NO: 56           moltype = AA  length = 4
FEATURE                 Location/Qualifiers
source                  1..4
                        mol_type = protein
                        organism = synthetic construct
SEQUENCE: 56
GGFG                                                              4

SEQ ID NO: 57           moltype = AA  length = 4
FEATURE                 Location/Qualifiers
source                  1..4
                        mol_type = protein
                        organism = synthetic construct
SEQUENCE: 57
GVKG                                                              4

SEQ ID NO: 58           moltype = AA  length = 4
FEATURE                 Location/Qualifiers
source                  1..4
                        mol_type = protein
                        organism = synthetic construct
SEQUENCE: 58
VKGG                                                              4
```

We claim:

1. An antibody-drug conjugate (ADC) having the following formula (I), or a pharmaceutically acceptable salt or solvate thereof:

$$Ab\text{-}[L\text{-}D]_q \qquad (I),$$

wherein

Ab represents an anti-Claudin18.2 antibody,

L represents a linker,

D represents a cytotoxic or cytostatic drug, and q is selected from 1-20, 1-10, 1-8, 2-8, 4-8, and 6-8, wherein Ab comprises three heavy chain complementarity determining regions (HCDRs) and three light chain complementarity determining regions (LCDRs), wherein (i) according to the IMGT scheme, the HCDR1 comprises or consists of the amino acid sequence of SEQ ID NO: 6, the HCDR2 comprises or consists of the amino acid sequence of SEQ ID NO: 7, the HCDR3 comprises or consists of the amino acid sequence of SEQ ID NO: 8, the LCDR1 comprises or consists of the amino acid sequence of SEQ ID NO: 9, the LCDR2 comprises or consists of the amino acid sequence of EAS, and the LCDR3 comprises or consists of the amino acid sequence of SEQ ID NO: 11; or (ii) according to the Kabat scheme, the HCDR1 comprises or consists of the amino acid sequence of SEQ ID NO: 12, the HCDR2 comprises or consists of the amino acid sequence of SEQ ID NO: 13, the HCDR3 comprises or consists of the amino acid sequence of SEQ ID NO: 14, the LCDR1 comprises or consists of the amino acid sequence of SEQ ID NO: 15, the LCDR2 comprises or consists of the amino acid sequence of SEQ ID NO: 16, and the LCDR3 comprises or consists of the amino acid sequence of SEQ ID NO: 17.

2. The antibody-drug conjugate or the pharmaceutically acceptable salt or solvate thereof according to claim 1, wherein Ab comprises:

a heavy chain variable region sequence of SEQ ID NO: 1 or 3 or an amino acid sequence having at least 80%, 85%, 90%, 95%, 96%, 97%, 98% or 99% sequence identity thereto; or a light chain variable region sequence of SEQ ID NO: 2 or an amino acid sequence having at least 80%, 85%, 90%, 95%, 96%, 97%, 98% or 99% sequence identity thereto.

3. The antibody-drug conjugate or the pharmaceutically acceptable salt or solvate thereof according to claim 1, wherein D represents a camptothecin drug comprising the following structure:

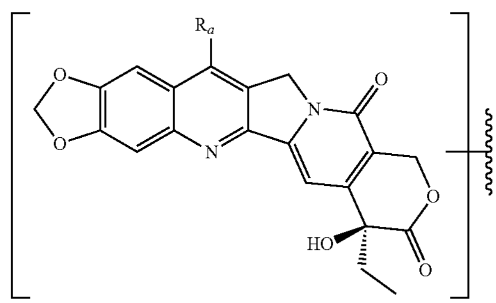

wherein $R_a$ is selected from:

hydrogen;

$C_3$-$C_8$ cycloalkyl;

phenyl; and $C_1$-$C_8$ alkyl optionally substituted with a substituent selected from: halogen, hydroxy, $C_1$-$C_4$ alkoxy optionally substituted with $NH_2$, $NH(C_1$-$C_4$ alkyl) and $N(C_1$-$C_4$ alkyl$)_2$, $C_3$-$C_8$ cycloalkyl, heterocycloalkyl, phenyl, and $NR^1R^2$, wherein $R^1$ and $R^2$ are each independently selected from:

hydrogen;

$C_1$-$C_8$ alkyl optionally substituted with a substituent selected from: hydroxy, amino, amino substituted with one or two $C_1$-$C_4$ alkyl, amino substituted with one or two $C_1$-$C_4$ hydroxyalkyl, and amino substituted with ($C_1$-$C_4$ hydroxyalkyl) and ($C_1$-$C_4$ alkyl);

$C_1$-$C_4$ alkyl substituted with 1 or 2 $C_3$-$C_{10}$ cycloalkyl, $C_3$-$C_{10}$ heterocycloalkyl, phenyl or heteroaryl;

$C_3$-$C_{10}$ cycloalkyl;

$C_3$-$C_{10}$ heterocycloalkyl;

$C_2$-$C_6$ heteroalkyl;

heteroaryl;

optionally halogenated phenyl; and $C_1$-$C_8$ alkyl-C(=O)— optionally substituted with hydroxy or amino;

or, $R^1$ and $R^2$, in combination with the nitrogen atom to which they are connected, form a 5-, 6-, or 7-membered heterocycle having 0-3 substituents selected from halogen, $C_1$-$C_4$ alkyl, OH, $C_1$-$C_4$ alkoxy, $NH_2$, $NH(C_1$-$C_4$ alkyl), and $N(C_1$-$C_4$ alkyl$)_2$, wherein the cycloalkyl, heterocycloalkyl, phenyl and heteroaryl, at each occurrence, are each independently and optionally substituted with 0-3 substituents selected from: OH, $C_1$-$C_4$ alkyl, $C_1$-$C_4$ alkoxy, $NH_2$, $NIH(C_1$-$C_4$ alkyl), and $N(C_1$-$C_4$ alkyl$)_2$.

4. The antibody-drug conjugate or the pharmaceutically acceptable salt or solvate thereof according to claim 1, wherein the L-D unit in formula (I) comprises the following structure:

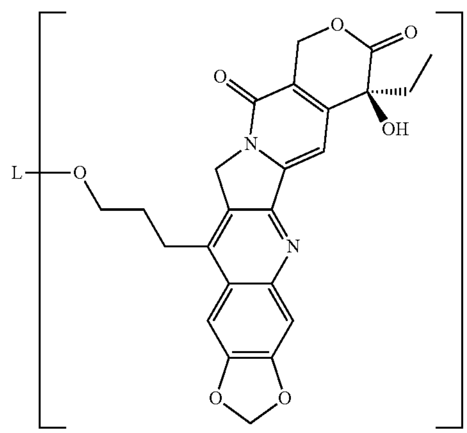

5. The antibody-drug conjugate or the pharmaceutically acceptable salt or solvate thereof according to claim 1, wherein L is a peptide-containing linker and comprises the following structure of formula (II):

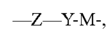

—Z—Y-M-, wherein

Z is a linking group linked to Ab,

Y is a peptide of 2-5 amino acids, and

M is absent or is a spacer group for linking to the drug D.

6. The antibody-drug conjugate or the pharmaceutically acceptable salt or solvate thereof according to claim 5, wherein Y is a peptide having an amino acid sequence of the following formula from the N-terminus to the C-terminus:

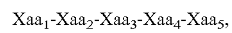

$Xaa_1$-$Xaa_2$-$Xaa_3$-$Xaa_4$-$Xaa_5$, wherein $Xaa_1$ is absent or is an amino acid selected from valine, glycine, alanine, and glutamic acid;

$Xaa_2$ is an amino acid selected from phenylalanine, leucine, and valine;

$Xaa_3$ is unsubstituted or substituted lysine;

$Xaa_4$ is an amino acid selected from leucine, glycine, and alanine;

$Xaa_5$ is absent or is an amino acid selected from glycine and alanine; and wherein the N-terminus of the amino acid sequence is linked to Z, and the C-terminus is linked to M (if M is present) or directly linked to the drug D.

7. The antibody-drug conjugate or the pharmaceutically acceptable salt or solvate thereof according to claim 5, wherein Y is

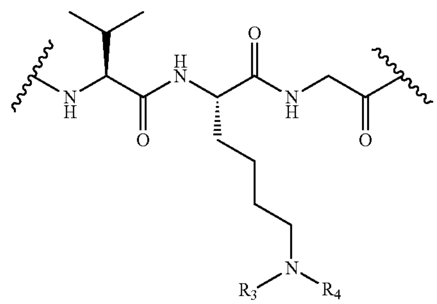

wherein $R_3$ and $R_4$ are each independently selected from methyl, ethyl, and propyl; and wherein the left wavy line indicates the position where Y is linked to Z, and the right wavy line indicates the position where Y is linked to M.

8. The antibody-drug conjugate or the pharmaceutically acceptable salt or solvate thereof according to claim 5, wherein Z has the following structure:

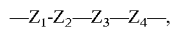

$—Z_1\text{-}Z_2—Z_3—Z_4—$, wherein $Z_1$ is a sulfur atom in Ab;

$Z_2$ is 5- to 10-membered heterocyclyl containing 1 or 2 heteroatoms selected from N, S, and O;

$Z_3$ is selected from a bond, —C(═O)—, —$C_1$-$C_{10}$ alkylene-C(═O)—, —$C_3$-$C_{10}$ alkynylene-C(═O)—, —$C_3$-$C_{10}$ alkenylene-C(═O)—, —$C_1$-$C_{10}$ heteroalkylene-C(═O)—, —$C_3$-$C_8$ cycloalkylene-C(═O)—, —O—$C_1$-$C_8$ alkylene-C(═O)—, -arylene-C(═O)—, —$C_1$-$C_{10}$ alkylene-arylene-C(═O)—, -arylene-$C_1$-$C_{10}$ alkylene-C(═O)—, —$C_1$-$C_{10}$ alkylene-$C_3$-$C_8$ cycloalkylene-C(═O)—, —$C_3$-$C_8$ cycloalkylene-$C_1$-$C_{10}$-alkylene-C(═O)—, —$C_3$-$C_8$-heterocyclylene-C(═O)—, —$C_1$-$C_{10}$ alkylene-$C_3$-$C_8$-heterocyclylene-C(═O)—, and —$C_3$-$C_8$ heterocyclylene-$C_1$-$C_{10}$ alkylene-C(═O)—; and $Z_4$ is a bond or a PEG unit represented by the following formula:

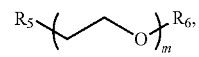

wherein $R_5$ is selected from $C_{1-4}$ alkylene, —NH—, and —NH—$C_{1-4}$ alkylene-heteroaryl-, wherein the heteroaryl is a 5- or 6-membered nitrogen-containing heteroaryl; and $R_6$ is —C(═O)—, $C_{1-4}$ alkylene, $C_{1-4}$ alkylene-C(═O)—, —NH—C(═O)—($CH_2OCH_2$)—C(═O)—, and $C_{1-4}$ alkylene-NH—C(═O)—($CH_2OCH_2$)—C(═O)—, wherein m is an integer of 2-12.

9. The antibody-drug conjugate or the pharmaceutically acceptable salt or solvate thereof according to claim 5, wherein M is absent or is amino-$C_1$-$C_3$ alkylene or amino-phenyl-$C_1$-$C_3$ alkylene-O—C(═O)—.

10. The antibody-drug conjugate or the pharmaceutically acceptable salt or solvate thereof according to claim 5, wherein L is a linker comprising the following structure:

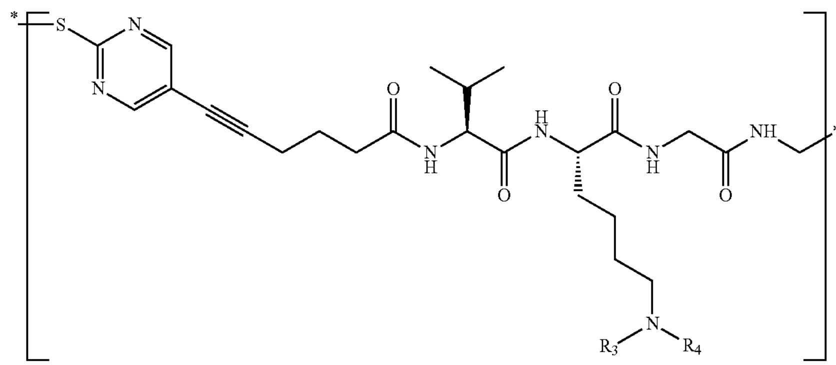

wherein $R_3$ and $R_4$ are each independently selected from methyl, ethyl, and propyl.

11. The antibody-drug conjugate or the pharmaceutically acceptable salt or solvate thereof according to claim 10, wherein $R_3$ and $R_4$ are both methyl; or $R_3$ and $R_4$ are both ethyl; or $R_3$ and $R_4$ are both propyl.

12. The antibody-drug conjugate or the pharmaceutically acceptable salt or solvate thereof according to claim 1, wherein the L-D unit in formula I is linked to the antibody by forming a thioether bond with a sulfhydryl group of a cysteine of the light chain and/or heavy chain of Ab.

13. The antibody-drug conjugate or the pharmaceutically acceptable salt or solvate thereof according to claim 1, wherein the ADC is selected from:

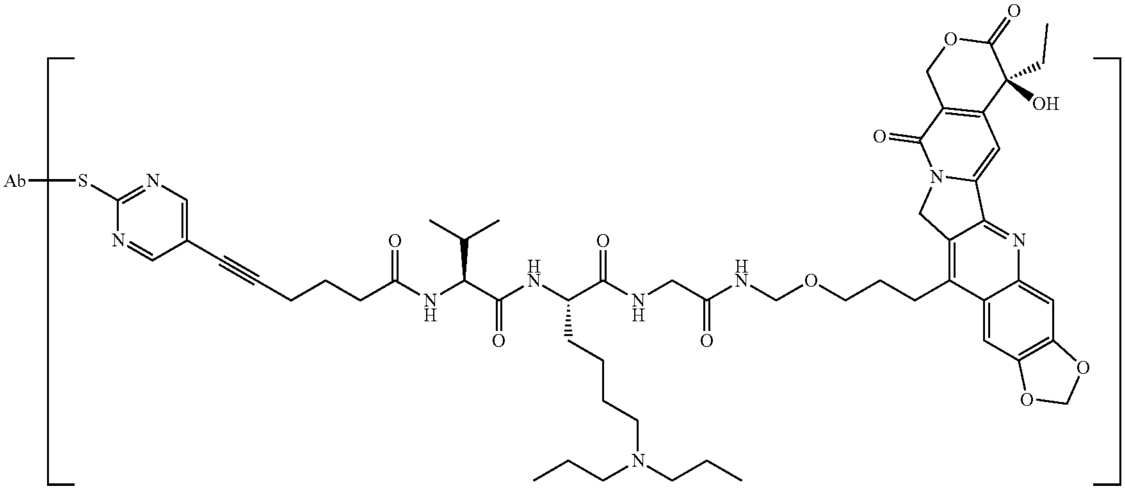

or

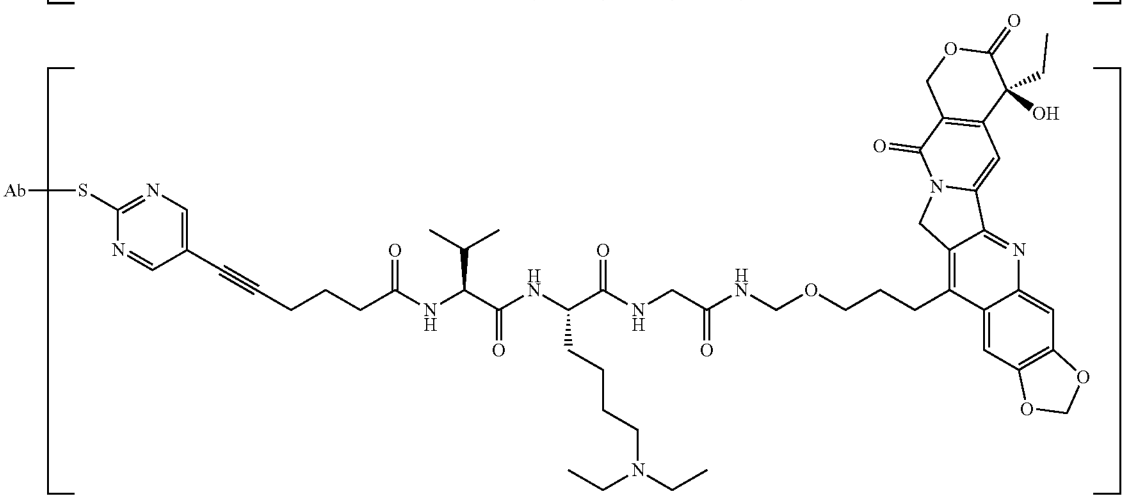

or

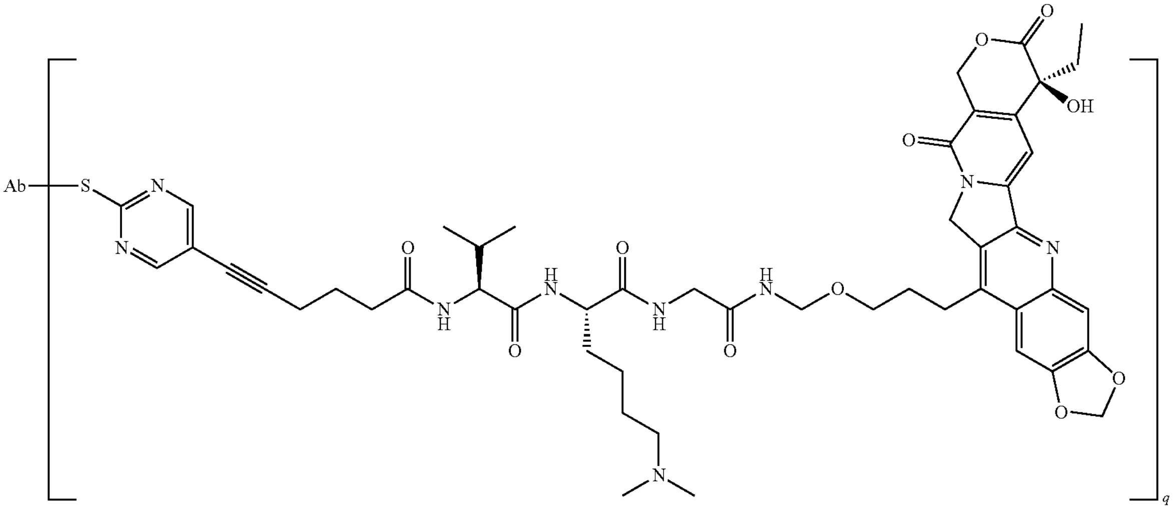

, wherein q is an average DAR value selected from 1-8, about 2, about 4, about 6, about 7, and about 8.

14. A pharmaceutical composition, comprising the antibody-drug conjugate or the pharmaceutically acceptable salt or solvate thereof according to claim 1, and a pharmaceutical auxiliary material.

15. An antibody or an antigen-binding fragment thereof that binds to CLAUDIN 18.2, comprising:

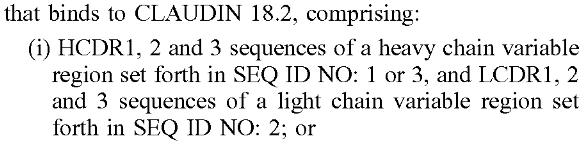

(i) HCDR1, 2 and 3 sequences of a heavy chain variable region set forth in SEQ ID NO: 1 or 3, and LCDR1, 2 and 3 sequences of a light chain variable region set forth in SEQ ID NO: 2; or (ii) HCDR1, 2 and 3 sequences of a heavy chain variable region set forth in SEQ ID NO: 21, and LCDR1, 2 and 3 sequences of a light chain variable region set forth in SEQ ID NO: 22; or (iii) HCDR1, 2 and 3 sequences of a heavy chain variable region set forth in SEQ ID NO: 23, and LCDR1, 2 and 3 sequences of a light chain variable region set forth in SEQ ID NO: 24; or (iv) HCDR1, 2 and 3 sequences of a heavy chain variable region set forth in SEQ ID NO: 38 or 40, and LCDR1, 2 and 3 sequences of a light chain variable region set forth in SEQ ID NO: 39; or (v) HCDR1, 2 and 3 sequences of a heavy chain variable region set forth in SEQ ID NO: 44, and LCDR1, 2 and 3 sequences of a light chain variable region set forth in SEQ ID NO: 45; or (vi) HCDR1, 2 and 3 sequences of a heavy chain variable region set forth in SEQ ID NO: 46, and LCDR1, 2 and 3 sequences of a light chain variable region set forth in SEQ ID NO: 47; or (vii) HCDR1, 2 and 3 sequences of a heavy chain variable region set forth in SEQ ID NO: 48, and LCDR1, 2 and 3 sequences of a light chain variable region set forth in SEQ ID NO: 49; or (viii) HCDR1, 2 and 3 sequences of a heavy chain variable region set forth in SEQ ID NO: 50, and LCDR1, 2 and 3 sequences of a light chain variable region set forth in SEQ ID NO: 51; or (ix) HCDR1, 2 and 3 sequences of a heavy chain variable region set forth in SEQ ID NO: 52, and LCDR1, 2 and 3 sequences of a light chain variable region set forth in SEQ ID NO: 53, wherein the CDRs are defined according to Kabat or IMGT, or a combination thereof.

16. An isolated nucleic acid, encoding the anti-CLAUDIN 18.2 antibody or the antigen-binding fragment thereof according to claim 15.

17. A vector, comprising the nucleic acid according to claim 16.

18. A host cell, comprising the nucleic acid according to claim 16.

19. An immunoconjugate, comprising the antibody or the antigen-binding fragment thereof according to claim 15 conjugated to a therapeutic agent or a diagnostic agent.

20. A pharmaceutical composition, comprising the antibody or the antigen-binding fragment thereof according to claim 15 or an immunoconjugate comprising the antibody or the antigen-binding fragment thereof conjugated to a therapeutic agent or a diagnostic agent, and a pharmaceutical auxiliary material.

21. A method for preventing or treating a CLAUDIN 18.2-positive tumor in a subject, comprising administering to the subject an effective amount of the antibody-drug conjugate or the pharmaceutically acceptable salt or solvate thereof according to claim 1.

22. The method according to claim 21, wherein the CLAUDIN 18.2-positive tumor is selected from:

a) a digestive system tumor or a metastasis thereof, b) gastric cancer, pancreatic cancer, esophageal cancer, colon cancer, gallbladder cancer, liver cancer, or HER2 negative gastric cancer; and c) advanced or metastatic gastric cancer, or esophagogastric junction adenocarcinoma (EGJA).

23. A method for preventing or treating a CLAUDIN 18.2-positive tumor in a subject, comprising administering to the subject an effective amount of the antibody or the antigen-binding fragment thereof according to claim 15.

24. The antibody-drug conjugate or the pharmaceutically acceptable salt or solvate thereof according to claim 1, wherein D represents a topoisomerase I inhibitor or a camptothecin drug.

25. The antibody-drug conjugate or the pharmaceutically acceptable salt or solvate thereof according to claim 1, wherein Ab is an IgG1 antibody.

26. The antibody-drug conjugate or the pharmaceutically acceptable salt or solvate thereof according to claim 3, wherein $R_a$ is $-C_1$-$C_4$ alkyl-OH, $-C_1$-$C_4$ alkyl-O$-C_1$-$C_4$ alkyl-$NH_2$, or $-C_1$-$C_4$ alkyl-$NH_2$.

27. The antibody-drug conjugate or the pharmaceutically acceptable salt or solvate thereof according to claim 6, wherein $Xaa_3$ is lysine in which an ε-amino group is monosubstituted or disubstituted with $C_1$-$C_3$ alkyl.

28. The antibody-drug conjugate or the pharmaceutically acceptable salt or solvate thereof according to claim 5, wherein Z has the following structure:

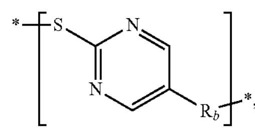

wherein $R_b$ is alkynylene-C(=O)— or alkenylene-C—(=O)—, wherein the left asterisk indicates the position where Z is linked to the antibody (Ab), and the right asterisk indicates the position where Z is linked to Y.

29. The antibody-drug conjugate or the pharmaceutically acceptable salt or solvate thereof according to claim 28, wherein Z has the following structure:

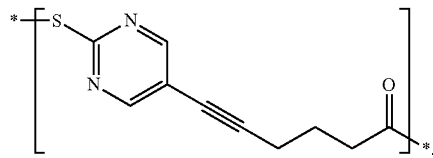

30. The antibody-drug conjugate or the pharmaceutically acceptable salt or solvate thereof according to claim 5, wherein M is:

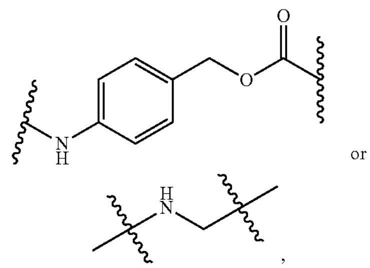

wherein the left wavy line indicates the linkage to Y and the right wavy line indicates the linkage to the drug D unit.

31. The antibody-drug conjugate or the pharmaceutically acceptable salt or solvate thereof according to claim 6, wherein Y is a peptide selected from: Phe-Lys-Gly, Leu-lys-Gly, Gly-Val-Lys-Gly (SEQ ID NO: 57), Val-Lys-Gly-Gly (SEQ ID NO: 58), Val-Lys-Gly, Val-Lys-Ala, and Val-Lys-Leu, wherein the Lys residue is unsubstituted lysine or lysine monosubstituted or disubstituted with $C_1$-$C_3$ alkyl.

32. The antibody-drug conjugate or the pharmaceutically acceptable salt or solvate thereof according to claim 13, wherein Ab is an IgG1 antibody comprising a heavy chain having the sequence of SEQ ID NO: 18 and a light chain having the sequence of SEQ ID NO: 20.

33. The antibody-drug conjugate or the pharmaceutically acceptable salt or solvate thereof according to claim 4, wherein the L-D unit in formula (I) comprises:

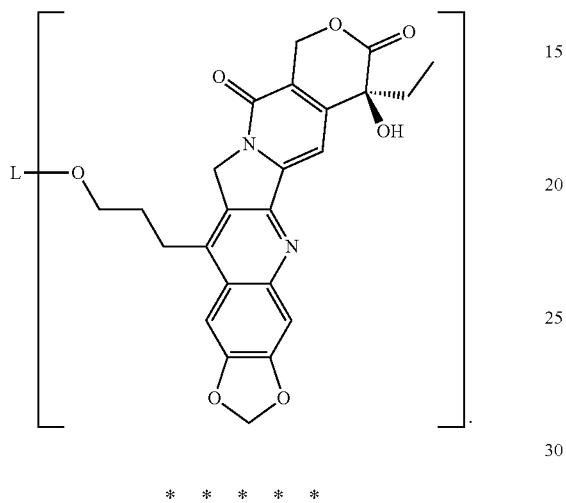

.

* * * * *